US010751412B2

(12) United States Patent
Yu et al.

(10) Patent No.: US 10,751,412 B2
(45) Date of Patent: Aug. 25, 2020

(54) COMBINATION OF A PD-1 ANTAGONIST AND CPG-C TYPE OLIGONUCLEOTIDE FOR TREATING CANCER

(71) Applicants: MERCK SHARP & DOHME CORP., Rahway, NJ (US); DYNAVAX TECHNOLOGIES CORPORATION, Emeryville, CA (US)

(72) Inventors: Ying Yu, Palo Alto, CA (US); Andrew Evan Denker, Wynnewood, PA (US); Svetlana Sadekova, Palo Alto, CA (US); Uyen Truong Phan, Palo Alto, CA (US); Robert A. Kastelein, Palo Alto, CA (US); David Ross Kaufman, North Wales, PA (US); Robert L. Coffman, Berkeley, CA (US); Cristiana Guiducci, Berkeley, CA (US); Robert S. Janssen, Berkeley, CA (US)

(73) Assignees: MERCK SHARP & DOHME CORP., Rahway, NJ (US); DYNAVAX TECHNOLOGIES CORPORATION, Emeryville, CA (US)

( * ) Notice: Subject to any disclaimer, the term of this patent is extended or adjusted under 35 U.S.C. 154(b) by 166 days.

(21) Appl. No.: 15/577,369

(22) PCT Filed: May 26, 2016

(86) PCT No.: PCT/US2016/034275
§ 371 (c)(1),
(2) Date: Nov. 28, 2017

(87) PCT Pub. No.: WO2016/196173
PCT Pub. Date: Dec. 8, 2016

(65) Prior Publication Data
US 2018/0169229 A1 Jun. 21, 2018

Related U.S. Application Data

(60) Provisional application No. 62/168,449, filed on May 29, 2015, provisional application No. 62/169,309, filed on Jun. 1, 2015.

(51) Int. Cl.
| A61K 39/395 | (2006.01) |
| A61K 45/06 | (2006.01) |
| A61K 31/7115 | (2006.01) |
| C07K 14/435 | (2006.01) |
| A61K 39/39 | (2006.01) |
| C07K 16/28 | (2006.01) |
| C07K 16/24 | (2006.01) |
| A61P 35/00 | (2006.01) |
| A61K 39/00 | (2006.01) |

(52) U.S. Cl.
CPC ........ *A61K 39/395* (2013.01); *A61K 31/7115* (2013.01); *A61K 39/39* (2013.01); *A61K 45/06* (2013.01); *A61P 35/00* (2018.01); *C07K 14/435* (2013.01); *C07K 16/244* (2013.01); *C07K 16/2818* (2013.01); *A61K 2039/505* (2013.01); *A61K 2039/55561* (2013.01); *A61K 2300/00* (2013.01); *C07K 2317/76* (2013.01)

(58) Field of Classification Search
CPC .................................................. A61K 39/395
USPC ....................................................... 424/133.1
See application file for complete search history.

(56) References Cited

U.S. PATENT DOCUMENTS

| 7,488,802 | B2 | 2/2009 | Collins et al. |
| 7,521,051 | B2 | 4/2009 | Collins et al. |
| 7,662,379 | B2 | 2/2010 | Presta |
| 7,745,606 | B2 | 6/2010 | Dina et al. |
| 8,008,449 | B2 | 8/2011 | Korman et al. |
| 8,158,768 | B2 | 4/2012 | Dina et al. |
| 8,168,757 | B2 | 5/2012 | Finnefrock et al. |
| 8,226,947 | B2 | 7/2012 | Presta |
| 8,354,509 | B2 | 1/2013 | Carven et al. |
| 8,372,413 | B2 | 2/2013 | Fearon et al. |
| 8,383,796 | B2 | 2/2013 | Korman et al. |
| 8,871,732 | B2 | 10/2014 | Dina et al. |
| 9,422,564 | B2 | 8/2016 | Dina et al. |
| 2006/0058254 | A1 | 3/2006 | Dina et al. |
| 2006/0140875 | A1 | 6/2006 | Krieg et al. |
| 2010/0086550 | A1 | 4/2010 | Kang et al. |
| 2010/0184834 | A1 | 7/2010 | Dina et al. |
| 2010/0203049 | A1 | 8/2010 | Presta |
| 2010/0266617 | A1 | 10/2010 | Carven et al. |
| 2011/0271358 | A1 | 11/2011 | Freeman et al. |

(Continued)

FOREIGN PATENT DOCUMENTS

| CN | 1745089 A | 3/2006 |
| CN | 1906213 A | 1/2007 |

(Continued)

OTHER PUBLICATIONS

Mamalis et al (Arch Dermatol Res, 2014, 306(6): 511-519).*
Hamid et al (NEJM, 2013, 369(2): 134-144).*
Lou et al (J Immunother, 2011, 34(3): 279-288).*
Intellectual Property Office of Singapore, Search Report and Written Opinion for Singaporean Patent Application No. 11201709542W, dated Jan. 29, 2019.
European Patent Office, Extended European Search Report for European Patent Application No. 16804054.1, dated Jan. 28, 2019.

(Continued)

Primary Examiner — Sean E Aeder
(74) Attorney, Agent, or Firm — Faegre Drinker Biddle & Reath LLP

(57) ABSTRACT

The present disclosure describes combination therapies comprising an antagonist of Programmed Death 1 receptor (PD-1) and a Toll-like receptor 9 (TLR9) agonist that is a CpG-C type oligonucleotide, and the use of the combination therapies for the treatment of cancer.

28 Claims, 35 Drawing Sheets
Specification includes a Sequence Listing.

(56) References Cited

U.S. PATENT DOCUMENTS

| | | | |
|---|---|---|---|
| 2013/0142814 A1* | 6/2013 | Dina | C07H 21/00 424/184.1 |
| 2016/0101128 A1 | 4/2016 | Wang et al. | |
| 2018/0000851 A1 | 1/2018 | Krieg | |
| 2018/0161427 A1 | 6/2018 | Yu et al. | |

FOREIGN PATENT DOCUMENTS

| | | |
|---|---|---|
| CN | 102131828 A | 7/2011 |
| CN | 103842030 A | 6/2014 |
| CN | 104271601 A | 1/2015 |
| WO | 9855495 A2 | 12/1998 |
| WO | 2004004771 A1 | 1/2004 |
| WO | 2004056875 A1 | 7/2004 |
| WO | 2004072286 A1 | 8/2004 |
| WO | 2008156712 A1 | 12/2008 |
| WO | 2010027827 A2 | 3/2010 |
| WO | 2010077634 A1 | 7/2010 |
| WO | 2011066342 A2 | 6/2011 |
| WO | WO-2012/006634 A2 | 1/2012 |
| WO | WO-2012/135408 A1 | 10/2012 |
| WO | WO-2013/019906 A1 | 2/2013 |
| WO | 2014100079 A1 | 6/2014 |
| WO | WO-2014/165422 A1 | 10/2014 |
| WO | WO-2015/016718 A1 | 2/2015 |
| WO | WO-2015/054642 A2 | 4/2015 |
| WO | 2015/167616 A1 | 11/2015 |
| WO | 2016/057898 A1 | 4/2016 |
| WO | 2016/109310 A1 | 7/2016 |

OTHER PUBLICATIONS

Lu et al., "TLR agonists for cancer immunotherapy: tipping the balance between the immune stimulatory and inhibitory effects", Frontiers in Immunology, vol. 5, Article 83 (Mar. 2014).
Wang et al., "Intratumoral injection of SD-101, a novel interferogenic TLR9 agonist, unlocks the full potential of PD-1 blockade," DynavaxTechnologies (2015).
Brody et al., "In Situ Vaccination With a TLR9 Agonist Induces Systemic Lymphoma Regression: A Phase I/II Study," Journal of Clinical Oncology, vol. 28, No. 28, pp. 4324-4332 (Oct. 1, 2010).
Mangsbo et al., "Enhanced Tumor Eradication by Combining CTLA-4 or PD-1 Blockade with CpG Therapy", J. Immunotherapy 33:3, pp. 225-235 (2010).
Sharma et al., "The Promise of PD-1 Signaling Pathway for Cancer Immunotherapy", J. Clin. Cell Immunol. vol. 3, Issue 4, 1000e110 (2012).
Ahmadzadeh et al., "Tumor antigen-specific CD8 T cells infiltrating the tumor express high levels of PD-1 and are functionally impaired", Blood (2009): 114: 1537-1544.
Chen et al., "PD-L1 Expressiion is characteristic of a subset of aggressive B-cell lymphomas and virus-associated malignancies", Clin. Cancer. Res. (2013): 19(13): 3462-3473.
Dong et al., "Tumor-associated B7-H1 promotes T-cell apoptosis: a potential mechanism of immune evasion", Nat. Med. Aug. 2002; 8(8):793-800.
Gadiot et al., "Overall survival and PD-L1 expression in metastasized malignant melanoma", Cancer (2011): 117:2192-2201.
Gao et al., "Overexpression of PD-L1 significantly associates with tumor aggressiveness and postoperative recurrence in human hepatocellular carcinoma", Clinical Cancer Research (2009): 15: 971-979.
Ghebeh et al., "FOXP3+ tregs and B7-H1+/PD-1+ T lymphocytes co-infiltrate the tumor tissues of high-risk breast cancer patients: implication for immunotherapy", BMC Cancer (Feb. 23, 2008): 8: 57.
Ghebeh et al., "The B7-H1 (PD-L1) T lymphocyte-inhibitory molecule is expressed in breast cancer patients with infiltrating ductal carcinoma: correlation with important high-risk prognostic factors", Neoplasia (2006): 8: 190-198.
Hamanishi et al., "Programmed cell death 1 ligand 1 and tumor-infiltrating CD8+ T lymphocytes are prognostic factors of human ovarian cancer", Proceeding of the National Academy of Sciences (2007): 104: 3360-3365.
Hind et al., "Tumor cell expression of programmed cell death-1 is a prognostic factor for malignant melanoma", Cancer (2010): 00: 1-9.
Inman et al., "PD-L1 (B7-H1) expression by urothelial carcinoma of the bladder and BCG-induced granulomata: associations with localized stage progression", Cancer (2007): 109: 1499-1505.
Nakanishi et al., "Overexpression of B7-H1 (PD-L1) significantly associates with tumor grade and postoperative prognosis in human urothelial cancers", Cancer Immunol. Immunother. (2007): 56:1173-1182.
Nomi et al., "Clinical significance and therapeutic potential of the programmed death- 1 ligand/programmed death- 1 pathway in human pancreatic cancer", Clinical Cancer Research (2007): 13: 2151-2157.
Ohigashi et al, "Clinical significance of programmed death- 1 ligand- 1 and programmed death- 1 ligand 2 expression in human esophageal cancer", Clinical Cancer Research (2005): 11: 2947-2953.
Raz et al.. "Preferential induction of a Th1 immune response and inhibition of specific IgE antibody formation by plasmid DNA immunization", Proc. Natl. Acad. Sci. USA (1996): 93: 5141-5145.
Sharpe et al. "The function of programmed cell death 1 and its ligands in regulating autoimmunity and infection", Nature Immunology (2007): 8(3): 239-245.
Shimauchi et al., "Augmented expression of programmed death-1 in both neoplasmatic and nonneoplastic CD4+ T cells in adult T-cell leukemia", Lymphoma. Int. J. Cancer (2007): 121: 2585-2590.
Taube et al., "Colocalization of inflammatory response with B7-H1 expressiion in human melanocytic lesions supports an adaptive resistance mechanism of immune escape", Sci .Transl. Med. (2012): 4(127): 127ra37.
Thompson et al., "Costimulatory B7-H1 in renal cell carcinoma patients: Indicator of tumor aggressiveness and potential therapeutic target", PNAS (2004): 101 (49): 17174-17179.
Thompson et al., "Significance of B7-H1 overexpression in kidney cancer", Clinical genitourin Cancer (2006): 5: 206-211.
Thompson et al., "Tumor B7-H1 is associated with poor prognosis in renal cell carcinoma pateitns with long-term follow-up", Cancer Res. (2006): 66:3381-3385.
Thompson et al., "PD-1 is expressed by tumor infiltrating cells and is associated with poor outcome for patients with renal carcinoma", Clinical Cancer Research (2007): 15: 1757-1761.
Toplian et al., Safety, activity, and immune correlates of anti—PD-1 antibody in cancer, New Eng. J Med. (2012): 366 (26): 2443-2454.
Who Drug Information, vol. 27, No. 1, pp. 68-69 (2013).
Yang et al. "PD-1 interaction contributes to the functional suppression of T-cell responses to human uveal melanoma cells in vitro.", Invest Ophthalmol Vis Sci. (Jun. 2008):49(6): 2518-2525.
Press Release (Jun. 1, 2015). "Merck and Dynavax Announce New Collaboration Investigating the Combination of Immuno-Oncology Therapies," Business Wire. 4 pages.
Wang et al., "Intratumoral injection of a CpG oligonucleotide reverts resistance to PD-1 blockade by expanding multifunctional CD8+ T cells," Proc Natl Acad Sci U S A. 113(46):E7240-E7249 (Epub Oct. 31, 2016).
Roman et al., "Immunostimulatory DNA sequences function T helper-I-promoting adjuvants ", Nature Med. (1997): 3:849-854.
"nivolumab" NCI Drug Dictionary, Jul. 7, 2015, pp. 1 of 1, Retrieved from the Internet <http:www.cancer.gov/publications/dictionaries/cancer-drug?cdrid=539733>.
Wang et al., "Intratumoral Administration of IMO-2125, a Novel TLR9 Agonist, Modulates Tumor Microenvironment and Potentiates Antitumor Activity of Anti-PD-1 mAb in Murine Colon Carcinoma and Melanoma Models," Idera Pharmaceuticals, Nov. 4, 2015, Retrieved from the Internet: <http://www.iderapharma.com/wp-content/uploads/2015/11/2125pd1-aacr_molecular_targets_mtg-final.pdf>.
International Search Report dated Sep. 22, 2016 for PCT/US2016/034275.

(56) References Cited

OTHER PUBLICATIONS

Written Opinion dated Sep. 22, 2016 for PCT/US2016/034275.
European Patent Office, Office Action for European Patent Application No. 16804054.1, dated Nov. 27, 2019.
National Intellectual Property Administration of the People'S Republic of China, First Office Action for Chinese Patent Application No. 201680043989.1, dated Nov. 28, 2019.
Japan Patent Office, Notice of Rejection for Japanese Patent Application No. 2017-561621, dated Jun. 2, 2020.

* cited by examiner hPD-1.08A light chain CDR1 (SEQ ID NO:1)

Arg Ala Ser Lys Ser Val Ser Thr Ser Gly Phe Ser Tyr Leu His hPD-1.08A light chain CDR2 (SEQ ID NO:2)

Leu Ala Ser Asn Leu Glu Ser hPD-1.08A light chain CDR3 (SEQ ID NO:3)

Gln His Ser Trp Glu Leu Pro Leu Thr hPD-1.08A heavy chain CDR1 (SEQ ID NO:4)

Ser Tyr Tyr Leu Tyr hPD-1.08A heavy chain CDR2 (SEQ ID NO:5)

Gly Val Asn Pro Ser Asn Gly Gly Thr Asn Phe Ser Glu Lys Phe Lys Ser hPD-1.08A heavy chain CDR3 (SEQ ID NO:6)

Arg Asp Ser Asn Tyr Asp Gly Gly Phe Asp Tyr

FIG. 1 hPD-1.09A light chain CDR1 (SEQ ID NO:7)

Arg Ala Ser Lys Gly Val Ser Thr Ser Gly Tyr Ser Tyr Leu His hPD-1.09A light chain CDR2 (SEQ ID NO:8)

Leu Ala Ser Tyr Leu Glu Ser hPD-1.09A light chain CDR3 (SEQ ID NO:9)

Gln His Ser Arg Asp Leu Pro Leu Thr hPD-1.09A heavy chain CDR1 (SEQ ID NO:10)

Asn Tyr Tyr Met Tyr hPD-1.09A heavy chain CDR2 (SEQ ID NO:11)

Gly Ile Asn Pro Ser Asn Gly Gly Thr Asn Phe Asn Glu Lys Phe Lys Asn hPD-1.09A heavy chain CDR3 (SEQ ID NO:12)

Arg Asp Tyr Arg Phe Asp Met Gly Phe Asp Tyr

FIG. 2

109A-H heavy chain variable region (SEQ ID NO:13)

Gln Val Gln Leu Val Gln Ser Gly Val Glu Val Lys Lys Pro Gly Ala Ser Val
Lys Val Ser Cys Lys Ala Ser Gly Tyr Thr Phe Thr Asn Tyr Tyr Met Tyr Trp
Val Arg Gln Ala Pro Gly Gln Gly Leu Glu Trp Met Gly Gly Ile Asn Pro Ser
Asn Gly Gly Thr Asn Phe Asn Glu Lys Phe Lys Asn Arg Val Thr Leu Thr Thr
Asp Ser Ser Thr Thr Thr Ala Tyr Met Glu Leu Lys Ser Leu Gln Phe Asp Asp
Thr Ala Val Tyr Tyr Cys Ala Arg Arg Asp Tyr Arg Phe Asp Met Gly Phe Asp
Tyr Trp Gly Gln Gly Thr Thr Val Thr Val Ser Ser

409A-H heavy chain full length (SEQ ID NO:14)

Gln Val Gln Leu Val Gln Ser Gly Val Glu Val Lys Lys Pro Gly Ala Ser Val
Lys Val Ser Cys Lys Ala Ser Gly Tyr Thr Phe Thr Asn Tyr Tyr Met Tyr Trp
Val Arg Gln Ala Pro Gly Gln Gly Leu Glu Trp Met Gly Gly Ile Asn Pro Ser
Asn Gly Gly Thr Asn Phe Asn Glu Lys Phe Lys Asn Arg Val Thr Leu Thr Thr
Asp Ser Ser Thr Thr Thr Ala Tyr Met Glu Leu Lys Ser Leu Gln Phe Asp Asp
Thr Ala Val Tyr Tyr Cys Ala Arg Arg Asp Tyr Arg Phe Asp Met Gly Phe Asp
Tyr Trp Gly Gln Gly Thr Thr Val Thr Val Ser Ser Ala Ser Thr Lys Gly Pro
Ser Val Phe Pro Leu Ala Pro Cys Ser Arg Ser Thr Ser Glu Ser Thr Ala Ala
Leu Gly Cys Leu Val Lys Asp Tyr Phe Pro Glu Pro Val Thr Val Ser Trp Asn
Ser Gly Ala Leu Thr Ser Gly Val His Thr Phe Pro Ala Val Leu Gln Ser Ser
Gly Leu Tyr Ser Leu Ser Ser Val Val Thr Val Pro Ser Ser Ser Leu Gly Thr
Lys Thr Tyr Thr Cys Asn Val Asp His Lys Pro Ser Asn Thr Lys Val Asp Lys
Arg Val Glu Ser Lys Tyr Gly Pro Pro Cys Pro Pro Cys Pro Ala Pro Glu Phe
Leu Gly Gly Pro Ser Val Phe Leu Phe Pro Pro Lys Pro Lys Asp Thr Leu Met
Ile Ser Arg Thr Pro Glu Val Thr Cys Val Val Val Asp Val Ser Gln Glu Asp
Pro Glu Val Gln Phe Asn Trp Tyr Val Asp Gly Val Glu Val His Asn Ala Lys
Thr Lys Pro Arg Glu Glu Gln Phe Asn Ser Thr Tyr Arg Val Val Ser Val Leu
Thr Val Leu His Gln Asp Trp Leu Asn Gly Lys Glu Tyr Lys Cys Lys Val Ser
Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys
Asn Gln Val Ser Leu Thr Cys Leu Val Lys Gly Phe Tyr Pro Ser Asp Ile Ala
Val Glu Trp Glu Ser Asn Gly Gln Pro Glu Asn Asn Tyr Lys Thr Thr Pro Pro
Val Leu Asp Ser Asp Gly Ser Phe Phe Leu Tyr Ser Arg Leu Thr Val Asp Lys
Ser Arg Trp Gln Glu Gly Asn Val Phe Ser Cys Ser Val Met His Glu Ala Leu
His Asn His Tyr Thr Gln Lys Ser Leu Ser Leu Ser Leu Gly Lys

FIG. 3

K09A-L-11 light chain variable region (SEQ ID NO:15)

Glu Ile Val Leu Thr Gln Ser Pro Ala Thr Leu Ser Leu Ser Pro Gly Glu
Arg Ala Thr Leu Ser Cys Arg Ala Ser Lys Gly Val Ser Thr Ser Gly Tyr
Ser Tyr Leu His Trp Tyr Gln Gln Lys Pro Gly Gln Ala Pro Arg Leu Leu
Ile Tyr Leu Ala Ser Tyr Leu Glu Ser Gly Val Pro Ala Arg Phe Ser Gly
Ser Gly Ser Gly Thr Asp Phe Thr Leu Thr Ile Ser Ser Leu Glu Pro Glu
Asp Phe Ala Val Tyr Tyr Cys Gln His Ser Arg Asp Leu Pro Leu Thr Phe
Gly Gly Gly Thr Lys Val Glu Ile Lys

K09A-L-16 light chain variable region (SEQ ID NO:16)

Glu Ile Val Leu Thr Gln Ser Pro Leu Ser Leu Pro Val Thr Pro Gly Glu
Pro Ala Ser Ile Ser Cys Arg Ala Ser Lys Gly Val Ser Thr Ser Gly Tyr
Ser Tyr Leu His Trp Tyr Leu Gln Lys Pro Gly Gln Ser Pro Gln Leu Leu
Ile Tyr Leu Ala Ser Tyr Leu Glu Ser Gly Val Pro Asp Arg Phe Ser Gly
Ser Gly Ser Gly Thr Asp Phe Thr Leu Lys Ile Ser Arg Val Glu Ala Glu
Asp Val Gly Val Tyr Tyr Cys Gln His Ser Arg Asp Leu Pro Leu Thr Phe
Gly Gln Gly Thr Lys Leu Glu Ile Lys

K09A-L-17 light chain variable region (SEQ ID NO:17)

Asp Ile Val Met Thr Gln Thr Pro Leu Ser Leu Pro Val Thr Pro Gly Glu
Pro Ala Ser Ile Ser Cys Arg Ala Ser Lys Gly Val Ser Thr Ser Gly Tyr
Ser Tyr Leu His Trp Tyr Leu Gln Lys Pro Gly Gln Ser Pro Gln Leu Leu
Ile Tyr Leu Ala Ser Tyr Leu Glu Ser Gly Val Pro Asp Arg Phe Ser Gly
Ser Gly Ser Gly Thr Ala Phe Thr Leu Lys Ile Ser Arg Val Glu Ala Glu
Asp Val Gly Leu Tyr Tyr Cys Gln His Ser Arg Asp Leu Pro Leu Thr Phe
Gly Gln Gly Thr Lys Leu Glu Ile Lys

FIG. 4

K09A-L-11 light chain full length (SEQ ID NO:18)

Glu Ile Val Leu Thr Gln Ser Pro Ala Thr Leu Ser Leu Ser Pro Gly Glu
Arg Ala Thr Leu Ser Cys Arg Ala Ser Lys Gly Val Ser Thr Ser Gly Tyr
Ser Tyr Leu His Trp Tyr Gln Gln Lys Pro Gly Gln Ala Pro Arg Leu Leu
Ile Tyr Leu Ala Ser Tyr Leu Glu Ser Gly Val Pro Ala Arg Phe Ser Gly
Ser Gly Ser Gly Thr Asp Phe Thr Leu Thr Ile Ser Ser Leu Glu Pro Glu
Asp Phe Ala Val Tyr Tyr Cys Gln His Ser Arg Asp Leu Pro Leu Thr Phe
Gly Gly Gly Thr Lys Val Glu Ile Lys Arg Thr Val Ala Ala Pro Ser Val
Phe Ile Phe Pro Pro Ser Asp Glu Gln Leu Lys Ser Gly Thr Ala Ser Val
Val Cys Leu Leu Asn Asn Phe Tyr Pro Arg Glu Ala Lys Val Gln Trp Lys
Val Asp Asn Ala Leu Gln Ser Gly Asn Ser Gln Glu Ser Val Thr Glu Gln
Asp Ser Lys Asp Ser Thr Tyr Ser Leu Ser Ser Thr Leu Thr Leu Ser Lys
Ala Asp Tyr Glu Lys His Lys Val Tyr Ala Cys Glu Val Thr His Gln Gly
Leu Ser Ser Pro Val Thr Lys Ser Phe Asn Arg Gly Glu Cys

K09A-L-16 light chain full length (SEQ ID NO:19)

Glu Ile Val Leu Thr Gln Ser Pro Leu Ser Leu Pro Val Thr Pro Gly Glu
Pro Ala Ser Ile Ser Cys Arg Ala Ser Lys Gly Val Ser Thr Ser Gly Tyr
Ser Tyr Leu His Trp Tyr Leu Gln Lys Pro Gly Gln Ser Pro Gln Leu Leu
Ile Tyr Leu Ala Ser Tyr Leu Glu Ser Gly Val Pro Asp Arg Phe Ser Gly
Ser Gly Ser Gly Thr Asp Phe Thr Leu Lys Ile Ser Arg Val Glu Ala Glu
Asp Val Gly Val Tyr Tyr Cys Gln His Ser Arg Asp Leu Pro Leu Thr Phe
Gly Gln Gly Thr Lys Leu Glu Ile Lys Arg Thr Val Ala Ala Pro Ser Val
Phe Ile Phe Pro Pro Ser Asp Glu Gln Leu Lys Ser Gly Thr Ala Ser Val
Val Cys Leu Leu Asn Asn Phe Tyr Pro Arg Glu Ala Lys Val Gln Trp Lys
Val Asp Asn Ala Leu Gln Ser Gly Asn Ser Gln Glu Ser Val Thr Glu Gln
Asp Ser Lys Asp Ser Thr Tyr Ser Leu Ser Ser Thr Leu Thr Leu Ser Lys
Ala Asp Tyr Glu Lys His Lys Val Tyr Ala Cys Glu Val Thr His Gln Gly
Leu Ser Ser Pro Val Thr Lys Ser Phe Asn Arg Gly Glu Cys

FIG. 5A

K09A-L-17 light chain full length (SEQ ID NO:20)

Asp Ile Val Met Thr Gln Thr Pro Leu Ser Leu Pro Val Thr Pro Gly Glu
Pro Ala Ser Ile Ser Cys Arg Ala Ser Lys Gly Val Ser Thr Ser Gly Tyr
Ser Tyr Leu His Trp Tyr Leu Gln Lys Pro Gly Gln Ser Pro Gln Leu Leu
Ile Tyr Leu Ala Ser Tyr Leu Glu Ser Gly Val Pro Asp Arg Phe Ser Gly
Ser Gly Ser Gly Thr Ala Phe Thr Leu Lys Ile Ser Arg Val Glu Ala Glu
Asp Val Gly Leu Tyr Tyr Cys Gln His Ser Arg Asp Leu Pro Leu Thr Phe
Gly Gln Gly Thr Lys Leu Glu Ile Lys Arg Thr Val Ala Ala Pro Ser Val
Phe Ile Phe Pro Pro Ser Asp Glu Gln Leu Lys Ser Gly Thr Ala Ser Val
Val Cys Leu Leu Asn Asn Phe Tyr Pro Arg Glu Ala Lys Val Gln Trp Lys
Val Asp Asn Ala Leu Gln Ser Gly Asn Ser Gln Glu Ser Val Thr Glu Gln
Asp Ser Lys Asp Ser Thr Tyr Ser Leu Ser Ser Thr Leu Thr Leu Ser Lys
Ala Asp Tyr Glu Lys His Lys Val Tyr Ala Cys Glu Val Thr His Gln Gly
Leu Ser Ser Pro Val Thr Lys Ser Phe Asn Arg Gly Glu Cys

FIG. 5B

Pembrolizumab

Heavy chain (SEQ ID NO: 21)

```
QVQLVQSGVE VKKPGASVKV SCKASGYTFT NYYMYWVRQA PGQGLEWMGG  50
INPSNGGTNF NEKFKNRVTL TTDSSTTTAY MELKSLQFDD TAVYYCARRD 100
YRFDMGFDYW GQGTTVTVSS ASTKGPSVFP LAPCSRSTSE STAALGCLVK 150
DYFPEPVTVS WNSGALTSGV HTFPAVLQSS GLYSLSSVVT VPSSSLGTKT 200
YTCNVDHKPS NTKVDKRVES KYGPPCPPCP APEFLGGPSV FLFPPKPKDT 250
LMISRTPEVT CVVVDVSQED PEVQFNWYVD GVEVHNAKTK PREEQFNSTY 300
RVVSVLTVLH QDWLNGKEYK CKVSNKGLPS SIEKTISKAK GQPREPQVYT 350
LPPSQEEMTK NQVSLTCLVK GFYPSDIAVE WESNGQPENN YKTTPPVLDS 400
DGSFFLYSRL TVDKSRWQEG NVFSCSVMHE ALHNHYTQKS LSLSLGK    447
```

Light chain (SEQ ID NO:22)

```
EIVLTQSPAT LSLSPGERAT LSCRASKGVS TSGYSYLHWY QQKPGQAPRL  50
LIYLASYLES GVPARFSGSG SGTDFTLTIS SLEPEDFAVY YCQHSRDLPL 100
TFGGGTKVEI KRTVAAPSVF IFPPSDEQLK SGTASVVCLL NNFYPREAKV 150
QWKVDNALQS GNSQESVTEQ DSKDSTYSLS STLTLSKADY EKHKVYACEV 200
THQGLSSPVT KSFNRGEC                                   219
```

FIG. 6

Nivolumab

Heavy chain (SEQ ID NO:23)

```
QVQLVESGGG VVQPGRSLRL DCKASGITFS NSGMHWVRQA PGKGLEWVAV  50
IWYDGSKRYY ADSVKGRFTI SRDNSKNTLF LQMNSLRAED TAVYYCATND 100
DYWGQGTLVT VSSASTKGPS VFPLAPCSRS TSESTAALGC LVKDYFPEPV 150
TVSWNSGALT SGVHTFPAVL QSSGLYSLSS VVTVPSSSLG TKTYTCNVDH 200
KPSNTKVDKR VESKYGPPCP PCPAPEFLGG PSVFLFPPKP KDTLMISRTP 250
EVTCVVVDVS QEDPEVQFNW YVDGVEVHNA KTKPREEQFN STYRVVSVLT 300
VLHQDWLNGK EYKCKVSNKG LPSSIEKTIS KAKGQPREPQ VYTLPPSQEE 350
MTKNQVSLTC LVKGFYPSDI AVEWESNGQP ENNYKTTPPV LDSDGSFFLY 400
SRLTVDKSRW QEGNVFSCSV MHEALHNHYT QKSLSLSLGK           440
```

Light chain (SEQ ID NO:24)

```
EIVLTQSPAT LSLSPGERAT LSCRASQSVS SYLAWYQQKP GQAPRLLIYD  50
ASNRATGIPA RFSGSGSGTD FTLTISSLEP EDFAVYYCQQ SSNWPRTFGQ 100
GTKVEIKRTV AAPSVFIFPP SDEQLKSGTA SVVCLLNNFY PREAKVQWKV 150
DNALQSGNSQ ESVTEQDSKD STYSLSSTLT LSKADYEKHK VYACEVTHQG 200
LSSPVTKSFN RGEC                                      214
```

FIG. 7

Humanized x [IL-10_H] mAb (JES3.12G8) IgG1 / Kappa (CK)

Amino acid sequence of hu12G8 light chain. CDRs are underlined.

```
  1 DIQMTQSPSS LSASVGDRVT ITCKTSQNIF ENLAWYQQKP GKAPKLLIYN
 51 ASPLQAGVPS RFSGSGSGTD FTLTISSLQP EDFATYYCHQ YYSGYTFGPG
101 TKLELKRTVA APSVFIFPPS DEQLKSGTAS VVCLLNNFYP REAKVQWKVD
151 NALQSGNSQE SVTEQDSKDS TYSLSSTLTL SKADYEKHKV YACEVTHQGL
201 SSPVTKSFNR GEC (SEQ ID NO: 35)
```

Amino acid sequence of hu12G8 heavy chain. CDRs are underlined.

```
  1 QVQLVESGGG VVQPGRSLRL SCAASGFTFS DYHMAWVRQA PGKGLEWVAS
 51 ITLDATYTYY RDSVRGRFTI SRDNSKNTLY LQMNSLRAED TAVYYCARHR
101 GFSVWLDYWG QGTLVTVSSA STKGPSVFPL APSSKSTSGG TAALGCLVKD
151 YFPEPVTVSW NSGALTSGVH TFPAVLQSSG LYSLSSVVTV PSSSLGTQTY
201 ICNVNHKPSN TKVDKKVEPK SCDKTHTCPP CPAPELLGGP SVFLFPPKPK
251 DTLMISRTPE VTCVVVDVSH EDPEVKFNWY VDGVEVHNAK TKPREEQYNS
301 TYRVVSVLTV LHQDWLNGKE YKCKVSNKAL PAPIEKTISK AKGQPREPQV
351 YTLPPSRDEL TKNQVSLTCL VKGFYPSDIA VEWESNGQPE NNYKTTPPVL
401 DSDGSFFLYS KLTVDKSRWQ QGNVFSCSVM HEALHNHYTQ KSLSLSPGK
                    (SEQ ID NO: 34)
```

FIG.8

Mouse x IL-10_M mAb (TC40.11D8) IgG1/ Kappa (HY)

Amino acid sequence of 11D8 variable region of light chain

```
  1 DIVLTQSPAS LAVSLGQRAT ISCRASESVD DYGHSFMHWY QQKPGQPPKL
 51 LIWRASTLES GIPARFSGSG SRTDFTLTIN PVEADDVATY YCQQGNEDPW
101 TFGGGTKLEI K (SEQ ID NO: 37)
```

Amino acid sequence of 11D8 variable region of heavy chain.

```
  1 QVQLKQSGPG LVQPSQSLSI TCTVSGFSLT NYGVHWVRQS PGKGLEWLGV
 51 IWSGGSTDYN AAFISRLSIN KDNSKSQVFF KMNSLQANDT AIYYCARNRG
101 YDVYFDYWGQ GTTLTVSS (SEQ ID NO: 36)
```

FIG.9

P-values for comparison of volumes of injected between treatments, by day in TC-1 bilateral tumor model

| | Comparison | Day 2 | Day 6 | Day 9 | Day 12 |
|---|---|---|---|---|---|
| Unadjusted p-value | mIgG1 ctrl + C59-08 vs mIgG1 ctrl + ctrl ODN | 0.43275 | 0.01470 | 0.00590 | 0.00300 |
| | anti-IL-10 + CpG 1826 vs mIgG1 ctrl + ctrl ODN | 0.00680 | 0.00005 | 0.00005 | 0.00005 |
| | anti-IL-10 + ctrl ODN vs mIgG1 ctrl + ctrl ODN | 0.43870 | 0.21605 | 0.60770 | 0.31680 |
| | anti-IL-10 + C59-08 vs mIgG1 ctrl + ctrl ODN | 0.16680 | 0.00005 | 0.00005 | 0.00010 |
| | anti-IL-10 + C59-08 vs mIgG1 ctrl + C59-08 | 0.68310 | 0.00085 | 0.00035 | 0.00075 |
| | anti-IL-10 + C59-08 vs anti-IL-10 + ctrl ODN | 0.68895 | 0.00005 | 0.00005 | 0.00005 |
| Multiplicity-adjusted p-value | mIgG1 ctrl + C59-08 vs mIgG1 ctrl + ctrl ODN | 0.75145 | 0.03890 | 0.01530 | 0.01110 |
| | anti-IL-10 + CpG 1826 vs mIgG1 ctrl + ctrl ODN | 0.01770 | 0.00005 | 0.00005 | 0.00005 |
| | anti-IL-10 + ctrl ODN vs mIgG1 ctrl + ctrl ODN | 0.73685 | 0.43530 | 0.90605 | 0.57020 |
| | anti-IL-10 + C59-08 vs mIgG1 ctrl + ctrl ODN | 0.36930 | 0.00005 | 0.00010 | 0.00030 |
| | anti-IL-10 + C59-08 vs mIgG1 ctrl + C59-08 | 0.96850 | 0.00320 | 0.00095 | 0.00325 |
| | anti-IL-10 + C59-08 vs anti-IL-10 + ctrl ODN | 0.96100 | 0.00005 | 0.00005 | 0.00010 |

FIG. 10D

P-values for comparison of volumes of non-injected between treatments, by day in TC-1 bilateral tumor model

| | Comparison | Day 2 | Day 6 | Day 9 | Day 12 |
|---|---|---|---|---|---|
| Unadjusted p-value | mIgG1 ctrl + C59-08 vs mIgG1 ctrl + ctrl ODN | 0.24825 | 0.05340 | 0.00415 | 0.00980 |
| | anti-IL-10 + CpG 1826 vs mIgG1 ctrl + ctrl ODN | 0.39125 | 0.00525 | 0.00020 | 0.00035 |
| | anti-IL-10 + ctrl ODN vs mIgG1 ctrl + ctrl ODN | 0.98835 | 0.98865 | 0.60180 | 0.31865 |
| | anti-IL-10 + C59-08 vs mIgG1 ctrl + ctrl ODN | 0.22955 | 0.00300 | 0.00015 | 0.00010 |
| | anti-IL-10 + C59-08 vs mIgG1 ctrl + C59-08 | 0.98865 | 0.31145 | 0.13025 | 0.02500 |
| | anti-IL-10 + C59-08 vs anti-IL-10 + ctrl ODN | 0.29085 | 0.00840 | 0.00350 | 0.00090 |
| Multiplicity-adjusted p-value | mIgG1 ctrl + C59-08 vs mIgG1 ctrl + ctrl ODN | 0.44670 | 0.10775 | 0.01075 | 0.02525 |
| | anti-IL-10 + CpG 1826 vs mIgG1 ctrl + ctrl ODN | 0.66245 | 0.01250 | 0.00065 | 0.00085 |
| | anti-IL-10 + ctrl ODN vs mIgG1 ctrl + ctrl ODN | 1.00000 | 1.00000 | 0.87455 | 0.53805 |
| | anti-IL-10 + C59-08 vs mIgG1 ctrl + ctrl ODN | 0.42555 | 0.00750 | 0.00080 | 0.00040 |
| | anti-IL-10 + C59-08 vs mIgG1 ctrl + C59-08 | 1.00000 | 0.58620 | 0.26395 | 0.06245 |
| | anti-IL-10 + C59-08 vs anti-IL-10 + ctrl ODN | 0.47835 | 0.01915 | 0.00700 | 0.00250 |

FIG.11D

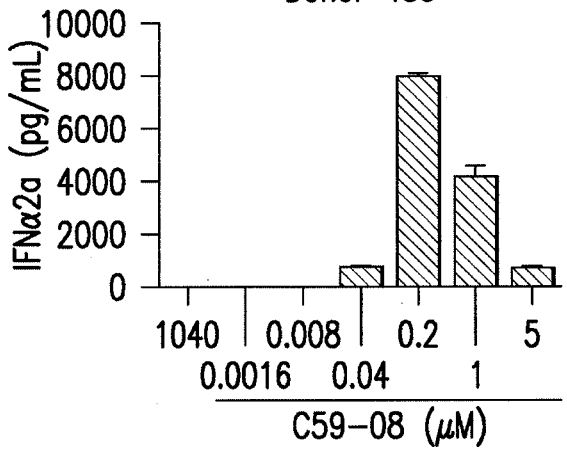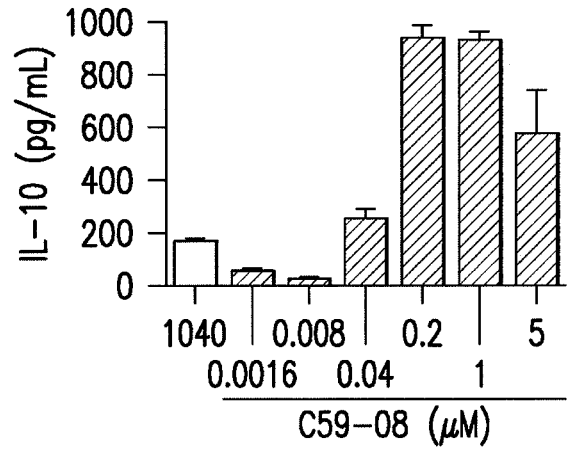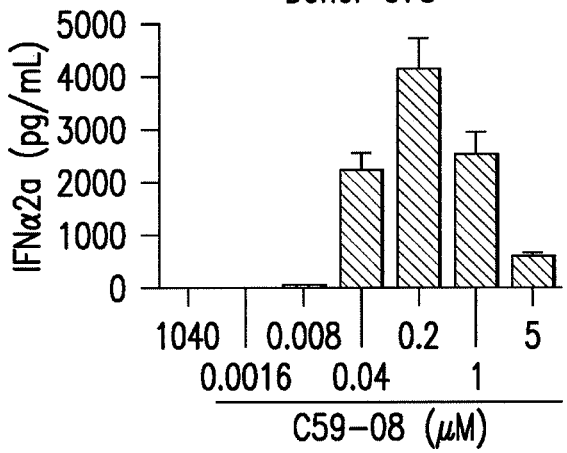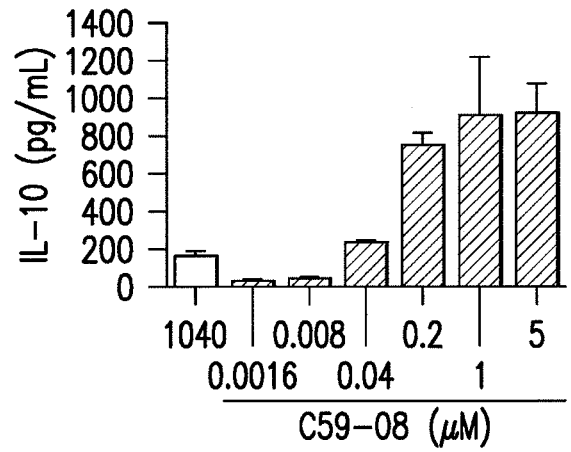
FIG.12

SEQUENCE LISTING

<160> NUMBER OF SEQ ID NOS: 65

<210> SEQ ID NO 1

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.08A light chain CDR1

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.08A light chain CDR2

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.08A light chain CDR3

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.08A heavy chain CDR1

<400> SEQUENCE: 4

Ser Tyr Tyr Leu Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.08A heavy chain CDR2

<400> SEQUENCE: 5

Gly Val Asn Pro Ser Asn Gly Gly Thr Asn Phe Ser Glu Lys Phe Lys
1               5                   10                  15

Ser
```

```
<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.08A heavy chain CDR3

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.09A light chain CDR1

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.09A light chain CDR2

<400> SEQUENCE: 8

Leu Ala Ser Tyr Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.09A light chain CDR3

<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.09A heavy chain CDR1

<400> SEQUENCE: 10

Asn Tyr Tyr Met Tyr
```

```
<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.09A heavy chain CDR2

<400> SEQUENCE: 11

Gly Ile Asn Pro Ser Asn Gly Gly Thr Asn Phe Asn Glu Lys Phe Lys
1               5                   10                  15

Asn

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hPD-1.09A heavy chain CDR3

<400> SEQUENCE: 12

Arg Asp Tyr Arg Phe Asp Met Gly Phe Asp Tyr
1               5                   10

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 109A-H heavy chain variable region

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 14
<211> LENGTH: 447
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: 409A-H heavy chain full length

<400> SEQUENCE: 14

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380
```

```
Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445
```

```
<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: K09A-L-11 light chain variable region

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110
```

```
<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: K09A-L-16 light chain variable region

<400> SEQUENCE: 16

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: K09A-L-17 light chain variable region

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 18
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: K09A-L-11 light chain full length

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr

```
                    165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: K09A-L-16 light chain full length

<400> SEQUENCE: 19

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: K09A-L-17 light chain full length

<400> SEQUENCE: 20
```

-continued

```
Asp Ile Val Met Thr Gln Thr Pro Leu Ser Leu Pro Val Thr Pro Gly
  1               5                  10                  15

Glu Pro Ala Ser Ile Ser Cys Arg Ala Ser Lys Gly Val Ser Thr Ser
             20                  25                  30

Gly Tyr Ser Tyr Leu His Trp Tyr Leu Gln Lys Pro Gly Gln Ser Pro
         35                  40                  45

Gln Leu Leu Ile Tyr Leu Ala Ser Tyr Leu Glu Ser Gly Val Pro Asp
     50                  55                  60

Arg Phe Ser Gly Ser Gly Ser Gly Thr Ala Phe Thr Leu Lys Ile Ser
 65                  70                  75                  80

Arg Val Glu Ala Glu Asp Val Gly Leu Tyr Tyr Cys Gln His Ser Arg
                 85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Pembrolizumab Heavy chain

<400> SEQUENCE: 21

Gln Val Gln Leu Val Gln Ser Gly Val Glu Val Lys Lys Pro Gly Ala
  1               5                  10                  15

Ser Val Lys Val Ser Cys Lys Ala Ser Gly Tyr Thr Phe Thr Asn Tyr
             20                  25                  30

Tyr Met Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
     50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                    165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                    245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                    325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                    405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
                435                 440                 445

<210> SEQ ID NO 22
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Pembrolizumab Light Chain

<400> SEQUENCE: 22

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
```

-continued

```
Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 23
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Nivolumab Heavy chain

<400> SEQUENCE: 23

```
Gln Val Gln Leu Val Glu Ser Gly Gly Val Val Gln Pro Gly Arg
 1               5                  10                  15

Ser Leu Arg Leu Asp Cys Lys Ala Ser Gly Ile Thr Phe Ser Asn Ser
             20                  25                  30

Gly Met His Trp Val Arg Gln Ala Pro Gly Lys Gly Leu Glu Trp Val
         35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160
```

```
Ser Gly Val His Thr Phe Pro Ala Val Leu Gln Ser Gly Leu Tyr
            165                 170                 175

Ser Leu Ser Ser Val Val Thr Val Pro Ser Ser Ser Leu Gly Thr Lys
        180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 24
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Nivolumab Light Chain

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 290
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 25

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205
```

```
Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
        275                 280                 285

Glu Thr
    290

<210> SEQ ID NO 26
<211> LENGTH: 11
<212> TYPE: PRT
<213> ORGANISM: Rattus norvegicus

<400> SEQUENCE: 26

Lys Thr Ser Gln Asn Ile Phe Glu Asn Leu Ala
1               5                   10

<210> SEQ ID NO 27
<211> LENGTH: 8
<212> TYPE: PRT
<213> ORGANISM: Rattus norvegicus

<400> SEQUENCE: 27

Tyr Asn Ala Ser Pro Leu Gln Ala
1               5

<210> SEQ ID NO 28
<211> LENGTH: 8
<212> TYPE: PRT
<213> ORGANISM: Rattus norvegicus

<400> SEQUENCE: 28

His Gln Tyr Tyr Ser Gly Tyr Thr
1               5

<210> SEQ ID NO 29
<211> LENGTH: 10
<212> TYPE: PRT
<213> ORGANISM: Rattus norvegicus

<400> SEQUENCE: 29

Gly Phe Thr Phe Ser Asp Tyr His Met Ala
1               5                   10

<210> SEQ ID NO 30
<211> LENGTH: 17
<212> TYPE: PRT
<213> ORGANISM: Rattus norvegicus

<400> SEQUENCE: 30

Ser Ile Thr Leu Asp Ala Thr Tyr Thr Tyr Tyr Arg Asp Ser Val Arg
1               5                   10                  15

Gly

<210> SEQ ID NO 31
<211> LENGTH: 10
```

```
<212> TYPE: PRT
<213> ORGANISM: Rattus norvegicus

<400> SEQUENCE: 31

His Arg Gly Phe Ser Val Trp Leu Asp Tyr
1               5                   10

<210> SEQ ID NO 32
<211> LENGTH: 120
<212> TYPE: PRT
<213> ORGANISM: Homo sapiens

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

His Met Ala Trp Val Arg Gln Ala Pro Gly Lys Gly Leu Glu Trp Val
            35                  40                  45

Ala Ser Ile Thr Leu Asp Ala Thr Tyr Thr Tyr Tyr Arg Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Ser Val Trp Leu Asp Tyr Trp Gly Gln Gly
            100                 105                 110

Thr Leu Val Thr Val Ser Ser Ala
        115                 120

<210> SEQ ID NO 33
<211> LENGTH: 111
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Phe Glu Asn
                20                  25                  30

Leu Ala Trp Tyr Gln Gln Lys Pro Gly Lys Ala Pro Lys Leu Leu Ile
            35                  40                  45

Tyr Asn Ala Ser Pro Leu Gln Ala Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Ser Gly Tyr Thr
                85                  90                  95

Phe Gly Pro Gly Thr Lys Leu Glu Leu Lys Arg Thr Val Ala Ala
            100                 105                 110

<210> SEQ ID NO 34
<211> LENGTH: 449
<212> TYPE: PRT
<213> ORGANISM: Homo sapiens

<400> SEQUENCE: 34

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Asp Tyr
         20                  25                  30

His Met Ala Trp Val Arg Gln Ala Pro Gly Lys Gly Leu Glu Trp Val
         35                  40                  45

Ala Ser Ile Thr Leu Asp Ala Thr Tyr Thr Tyr Tyr Arg Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg His Arg Gly Phe Ser Val Trp Leu Asp Tyr Trp Gly Gln Gly
         100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Asp Glu Leu Thr Lys Asn Gln Val Ser Leu Thr
         355                 360                 365

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430
```

Ala Leu His Asn His Tyr Thr Gln Lys Ser Leu Ser Leu Ser Pro Gly
            435                 440                 445

Lys

<210> SEQ ID NO 35
<211> LENGTH: 213
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Phe Glu Asn
            20                  25                  30

Leu Ala Trp Tyr Gln Gln Lys Pro Gly Lys Ala Pro Lys Leu Leu Ile
        35                  40                  45

Tyr Asn Ala Ser Pro Leu Gln Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Ser Gly Tyr Thr
                85                  90                  95

Phe Gly Pro Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 36
<211> LENGTH: 118
<212> TYPE: PRT
<213> ORGANISM: Mus sp.

<400> SEQUENCE: 36

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Asn Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala 85                  90                  95
Arg Asn Arg Gly Tyr Asp Val Tyr Phe Asp Tyr Trp Gly Gln Gly Thr
                100                 105                 110
Thr Leu Thr Val Ser Ser
        115

<210> SEQ ID NO 37
<211> LENGTH: 111
<212> TYPE: PRT
<213> ORGANISM: Mus sp.

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly His Ser Phe Met His Trp Tyr Gln Gln Lys Pro Gly Gln Pro Pro
        35                  40                  45

Lys Leu Leu Ile Trp Arg Ala Ser Thr Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Gly Asn
                85                  90                  95

Glu Asp Pro Trp Thr Phe Gly Gly Gly Thr Lys Leu Glu Ile Lys
                100                 105                 110

<210> SEQ ID NO 38
<211> LENGTH: 274
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (1)..(3)
<223> OTHER INFORMATION: a, c, t or g
<220> FEATURE:
<221> NAME/KEY: misc_feature
<222> LOCATION: (1)..(3)
<223> OTHER INFORMATION: This region may encompass 0-3 nucleotides
      wherein some positions may be absent
<220> FEATURE:
<221> NAME/KEY: misc_feature
<222> LOCATION: (4)..(23)
<223> OTHER INFORMATION: This region may encompass 1-4 'tcgnn' repeats
      wherein some positions may be absent
<220> FEATURE:
<221> NAME/KEY: modified_base
<222> LOCATION: (7)..(8)
<223> OTHER INFORMATION: a, c, t or g
<220> FEATURE:
<221> NAME/KEY: misc_feature
<222> LOCATION: (7)..(8)
<223> OTHER INFORMATION: This region may encompass 0-2 nucleotides
      wherein some positions may be absent
<220> FEATURE:
<221> NAME/KEY: modified_base
<222> LOCATION: (12)..(13)
<223> OTHER INFORMATION: a, c, t or g
<220> FEATURE:
<221> NAME/KEY: misc_feature
<222> LOCATION: (12)..(13)
<223> OTHER INFORMATION: This region may encompass 0-2 nucleotides
      wherein some positions may be absent
<220> FEATURE:
<221> NAME/KEY: modified_base

```
<222> LOCATION: (17)..(18)
<223> OTHER INFORMATION: a, c, t or g
<220> FEATURE:
<221> NAME/KEY: misc_feature
<222> LOCATION: (17)..(18)
<223> OTHER INFORMATION: This region may encompass 0-2 nucleotides
      wherein some positions may be absent
<220> FEATURE:
<221> NAME/KEY: modified_base
<222> LOCATION: (22)..(23)
<223> OTHER INFORMATION: a, c, t or g
<220> FEATURE:
<221> NAME/KEY: misc_feature
<222> LOCATION: (22)..(23)
<223> OTHER INFORMATION: This region may encompass 0-2 nucleotides
      wherein some positions may be absent
<220> FEATURE:
<221> NAME/KEY: modified_base
<222> LOCATION: (24)..(25)
<223> OTHER INFORMATION: a, c, t or g
<220> FEATURE:
<221> NAME/KEY: misc_feature
<222> LOCATION: (24)..(25)
<223> OTHER INFORMATION: This region may encompass 0-2 nucleotides
      wherein some positions may be absent
<220> FEATURE:
<221> NAME/KEY: modified_base
<222> LOCATION: (26)..(27)
<223> OTHER INFORMATION: a, c, t or g
<220> FEATURE:
<221> NAME/KEY: misc_feature
<222> LOCATION: (26)..(185)
<223> OTHER INFORMATION: This region may encompass 1-20 'nncgnncg'
      repeats wherein some positions may be absent
<220> FEATURE:
<221> NAME/KEY: modified_base
<222> LOCATION: (30)..(31)
<223> OTHER INFORMATION: a, c, t or g
<220> FEATURE:
<221> NAME/KEY: misc_feature
<222> LOCATION: (32)..(33)
<223> OTHER INFORMATION: May or may not be present
<220> FEATURE:
<221> NAME/KEY: modified_base
<222> LOCATION: (34)..(35)
<223> OTHER INFORMATION: a, c, t or g
<220> FEATURE:
<221> NAME/KEY: modified_base
<222> LOCATION: (38)..(39)
<223> OTHER INFORMATION: a, c, t or g
<220> FEATURE:
<221> NAME/KEY: misc_feature
<222> LOCATION: (40)..(41)
<223> OTHER INFORMATION: May or may not be present
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: misc_feature
<222> LOCATION: (48)..(49)
<223> OTHER INFORMATION: May or may not be present
<220> FEATURE:
<221> NAME/KEY: modified_base
<222> LOCATION: (50)..(51)
<223> OTHER INFORMATION: a, c, t or g
<220> FEATURE:
<221> NAME/KEY: modified_base
<222> LOCATION: (54)..(55)
<223> OTHER INFORMATION: a, c, t or g
<220> FEATURE:
<221> NAME/KEY: misc_feature
<222> LOCATION: (56)..(57)
<223> OTHER INFORMATION: May or may not be present
<220> FEATURE:
```

```
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (62)..(63)
<223> OTHER INFORMATION: a, c, t or g
<220> FEATURE:
<221> NAME/KEY: misc_feature
<222> LOCATION: (64)..(65)
<223> OTHER INFORMATION: May or may not be present
<220> FEATURE:
<221> NAME/KEY: modified_base
<222> LOCATION: (66)..(67)
<223> OTHER INFORMATION: a, c, t or g
<220> FEATURE:
<221> NAME/KEY: modified_base
<222> LOCATION: (70)..(71)
<223> OTHER INFORMATION: a, c, t or g
<220> FEATURE:
<221> NAME/KEY: misc_feature
<222> LOCATION: (72)..(73)
<223> OTHER INFORMATION: May or may not be present
<220> FEATURE:
<221> NAME/KEY: modified_base
<222> LOCATION: (74)..(75)
<223> OTHER INFORMATION: a, c, t or g
<220> FEATURE:
<221> NAME/KEY: modified_base
<222> LOCATION: (78)..(79)
<223> OTHER INFORMATION: a, c, t or g
<220> FEATURE:
<221> NAME/KEY: misc_feature
<222> LOCATION: (80)..(81)
<223> OTHER INFORMATION: May or may not be present
<220> FEATURE:
<221> NAME/KEY: modified_base
<222> LOCATION: (82)..(83)
<223> OTHER INFORMATION: a, c, t or g
<220> FEATURE:
<221> NAME/KEY: modified_base
<222> LOCATION: (86)..(87)
<223> OTHER INFORMATION: a, c, t or g
<220> FEATURE:
<221> NAME/KEY: misc_feature
<222> LOCATION: (88)..(89)
<223> OTHER INFORMATION: May or may not be present
<220> FEATURE:
<221> NAME/KEY: modified_base
<222> LOCATION: (90)..(91)
<223> OTHER INFORMATION: a, c, t or g
<220> FEATURE:
<221> NAME/KEY: modified_base
<222> LOCATION: (94)..(95)
<223> OTHER INFORMATION: a, c, t or g
<220> FEATURE:
<221> NAME/KEY: misc_feature
<222> LOCATION: (96)..(97)
<223> OTHER INFORMATION: May or may not be present
<220> FEATURE:
<221> NAME/KEY: modified_base
<222> LOCATION: (98)..(99)
<223> OTHER INFORMATION: a, c, t or g
<220> FEATURE:
<221> NAME/KEY: modified_base
<222> LOCATION: (102)..(103)
<223> OTHER INFORMATION: a, c, t or g
<220> FEATURE:
<221> NAME/KEY: misc_feature
<222> LOCATION: (104)..(105)
<223> OTHER INFORMATION: May or may not be present
<220> FEATURE:
<221> NAME/KEY: modified_base
<222> LOCATION: (106)..(107)
<223> OTHER INFORMATION: a, c, t or g
<220> FEATURE:
<221> NAME/KEY: modified_base
<222> LOCATION: (110)..(111)
<223> OTHER INFORMATION: a, c, t or g
```

```
<220> FEATURE:
<221> NAME/KEY: misc_feature
<222> LOCATION: (112)..(113)
<223> OTHER INFORMATION: May or may not be present
<220> FEATURE:
<221> NAME/KEY: modified_base
<222> LOCATION: (114)..(115)
<223> OTHER INFORMATION: a, c, t or g
<220> FEATURE:
<221> NAME/KEY: modified_base
<222> LOCATION: (118)..(119)
<223> OTHER INFORMATION: a, c, t or g
<220> FEATURE:
<221> NAME/KEY: misc_feature
<222> LOCATION: (120)..(121)
<223> OTHER INFORMATION: May or may not be present
<220> FEATURE:
<221> NAME/KEY: modified_base
<222> LOCATION: (122)..(123)
<223> OTHER INFORMATION: a, c, t or g
<220> FEATURE:
<221> NAME/KEY: modified_base
<222> LOCATION: (126)..(127)
<223> OTHER INFORMATION: a, c, t or g
<220> FEATURE:
<221> NAME/KEY: misc_feature
<222> LOCATION: (128)..(129)
<223> OTHER INFORMATION: May or may not be present
<220> FEATURE:
<221> NAME/KEY: modified_base
<222> LOCATION: (130)..(131)
<223> OTHER INFORMATION: a, c, t or g
<220> FEATURE:
<221> NAME/KEY: modified_base
<222> LOCATION: (134)..(135)
<223> OTHER INFORMATION: a, c, t or g
<220> FEATURE:
<221> NAME/KEY: misc_feature
<222> LOCATION: (136)..(137)
<223> OTHER INFORMATION: May or may not be present
<220> FEATURE:
<221> NAME/KEY: modified_base
<222> LOCATION: (138)..(139)
<223> OTHER INFORMATION: a, c, t or g
<220> FEATURE:
<221> NAME/KEY: modified_base
<222> LOCATION: (142)..(143)
<223> OTHER INFORMATION: a, c, t or g
<220> FEATURE:
<221> NAME/KEY: misc_feature
<222> LOCATION: (144)..(145)
<223> OTHER INFORMATION: May or may not be present
<220> FEATURE:
<221> NAME/KEY: modified_base
<222> LOCATION: (146)..(147)
<223> OTHER INFORMATION: a, c, t or g
<220> FEATURE:
<221> NAME/KEY: modified_base
<222> LOCATION: (150)..(151)
<223> OTHER INFORMATION: a, c, t or g
<220> FEATURE:
<221> NAME/KEY: misc_feature
<222> LOCATION: (152)..(153)
<223> OTHER INFORMATION: May or may not be present
<220> FEATURE:
<221> NAME/KEY: modified_base
<222> LOCATION: (154)..(155)
<223> OTHER INFORMATION: a, c, t or g
<220> FEATURE:
<221> NAME/KEY: modified_base
<222> LOCATION: (158)..(159)
<223> OTHER INFORMATION: a, c, t or g
<220> FEATURE:
<221> NAME/KEY: misc_feature
<222> LOCATION: (160)..(161)
<223> OTHER INFORMATION: May or may not be present
<220> FEATURE:
<221> NAME/KEY: modified_base
<222> LOCATION: (162)..(163)
```

```
<223> OTHER INFORMATION: a, c, t or g
<220> FEATURE:
<221> NAME/KEY: modified_base
<222> LOCATION: (166)..(167)
<223> OTHER INFORMATION: a, c, t or g
<220> FEATURE:
<221> NAME/KEY: misc_feature
<222> LOCATION: (168)..(169)
<223> OTHER INFORMATION: May or may not be present
<220> FEATURE:
<221> NAME/KEY: modified_base
<222> LOCATION: (170)..(171)
<223> OTHER INFORMATION: a, c, t or g
<220> FEATURE:
<221> NAME/KEY: modified_base
<222> LOCATION: (174)..(175)
<223> OTHER INFORMATION: a, c, t or g
<220> FEATURE:
<221> NAME/KEY: misc_feature
<222> LOCATION: (176)..(177)
<223> OTHER INFORMATION: May or may not be present
<220> FEATURE:
<221> NAME/KEY: modified_base
<222> LOCATION: (178)..(179)
<223> OTHER INFORMATION: a, c, t or g
<220> FEATURE:
<221> NAME/KEY: modified_base
<222> LOCATION: (182)..(183)
<223> OTHER INFORMATION: a, c, t or g
<220> FEATURE:
<221> NAME/KEY: misc_feature
<222> LOCATION: (184)..(185)
<223> OTHER INFORMATION: May or may not be present
<220> FEATURE:
<221> NAME/KEY: modified_base
<222> LOCATION: (186)..(274)
<223> OTHER INFORMATION: a, c, t or g
<220> FEATURE:
<221> NAME/KEY: misc_feature
<222> LOCATION: (186)..(274)
<223> OTHER INFORMATION: This region may encompass 0-89 nucleotides
      wherein some positions may be absent
<220> FEATURE:
<223> OTHER INFORMATION: See specification as filed for detailed
      description of substitutions and preferred embodiments

<400> SEQUENCE: 38
nnntcgnntc gnntcgnntc gnnnnnncgn ncgnncgnnc gnncgnncgn ncgnncgnnc      60
gnncgnncgn ncgnncgnnc gnncgnncgn ncgnncgnnc gnncgnncgn ncgnncgnnc     120
gnncgnncgn ncgnncgnnc gnncgnncgn ncgnncgnnc gnncgnncgn ncgnncgnnc     180
gnncgnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnn                                 274

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t or g
<220> FEATURE:
<221> NAME/KEY: misc_feature
<222> LOCATION: (4)..(8)
<223> OTHER INFORMATION: This region may encompass 0-5 nucleotides
      wherein some positions may be absent
<220> FEATURE:
<221> NAME/KEY: misc_feature
<222> LOCATION: (9)..(40)
<223> OTHER INFORMATION: This region may encompass 1-4 'nncgnncg'
```

```
         repeats wherein some positions may be absent
<220> FEATURE:
<221> NAME/KEY: modified_base
<222> LOCATION: (9)..(10)
<223> OTHER INFORMATION: a, c, t or g
<220> FEATURE:
<221> NAME/KEY: modified_base
<222> LOCATION: (13)..(14)
<223> OTHER INFORMATION: a, c, t or g
<220> FEATURE:
<221> NAME/KEY: modified_base
<222> LOCATION: (17)..(18)
<223> OTHER INFORMATION: a, c, t or g
<220> FEATURE:
<221> NAME/KEY: modified_base
<222> LOCATION: (21)..(22)
<223> OTHER INFORMATION: a, c, t or g
<220> FEATURE:
<221> NAME/KEY: modified_base
<222> LOCATION: (25)..(26)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: modified_base
<222> LOCATION: (33)..(34)
<223> OTHER INFORMATION: a, c, t or g
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (41)..(60)
<223> OTHER INFORMATION: a, c, t or g
<220> FEATURE:
<221> NAME/KEY: misc_feature
<222> LOCATION: (41)..(60)
<223> OTHER INFORMATION: This region may encompass 0-20 nucleotides
      wherein some positions may be absent
<220> FEATURE:
<223> OTHER INFORMATION: See specification as filed for detailed
      description of substitutions and preferred embodiments

<400> SEQUENCE: 39
tcgnnnnnnn cgnncgnncg nncgnncgnn cgnncgnncg nnnnnnnnnn nnnnnnnnnn      60

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (4)..(8)
<223> OTHER INFORMATION: a, c, t or g
<220> FEATURE:
<221> NAME/KEY: misc_feature
<222> LOCATION: (4)..(8)
<223> OTHER INFORMATION: This region may encompass 0-5 nucleotides
      wherein some positions may be absent
<220> FEATURE:
<221> NAME/KEY: modified_base
<222> LOCATION: (27)..(46)
<223> OTHER INFORMATION: a, c, t or g
<220> FEATURE:
<221> NAME/KEY: misc_feature
<222> LOCATION: (27)..(46)
<223> OTHER INFORMATION: This region may encompass 0-20 nucleotides
      wherein some positions may be absent
<220> FEATURE:
<223> OTHER INFORMATION: See specification as filed for detailed
      description of substitutions and preferred embodiments
```

```
<400> SEQUENCE: 40
tcgnnnnntt cgaacgttcg aacgttnnnn nnnnnnnnnn nnnnnn                   46

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 41
tcgtcgaacg ttcgagatga t                                             21

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 42
tcgttcgaac gttcgaacgt tcgaa                                         25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 43
tcgaacgttc gaacgttcga acgtt                                         25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 44
tcgaacgttc gaacgttcga atttt                                         25

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 45
tcgaacgttc gaacgttcga acgttcgaat                                    30

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      construct
```

```
<400> SEQUENCE: 46
tcgtaacgtt cgaacgttcg aacgtta                                     27

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 47
tcgtaacgtt cgaacgttcg aacgtt                                      26

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 48
tcgtaacgtt cgaacgttcg aacgt                                       25

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 49
tcgtaacgtt cgaacgttcg aacg                                        24

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 50
tcgtaacgtt cgaacgttcg aac                                         23

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 51
tcgtaacgtt cgaacgttcg aa                                          22

<210> SEQ ID NO 52
<211> LENGTH: 160
<212> TYPE: PRT
<213> ORGANISM: Homo sapiens

<400> SEQUENCE: 52

Ser Pro Gly Gln Gly Thr Gln Ser Glu Asn Ser Cys Thr His Phe Pro
1               5                   10                  15
```

```
Gly Asn Leu Pro Asn Met Leu Arg Asp Leu Arg Asp Ala Phe Ser Arg
         20                  25                  30

Val Lys Thr Phe Phe Gln Met Lys Asp Gln Leu Asp Asn Leu Leu Leu
 35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
             100                 105                 110

Pro Cys Glu Asn Lys Ser Lys Ala Val Glu Gln Val Lys Asn Ala Phe
         115                 120                 125

Asn Lys Leu Gln Glu Lys Gly Ile Tyr Lys Ala Met Ser Glu Phe Asp
     130                 135                 140

Ile Phe Ile Asn Tyr Ile Glu Ala Tyr Met Thr Met Lys Ile Arg Asn
145                 150                 155                 160

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 53
tccatgacgt tcctgacgtt                                            20

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 54
tgactgtgaa ccttagagat ga                                         22

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody MEB037.22C3 CDRL1

<400> SEQUENCE: 55

Lys Ser Ser Gln Ser Leu Leu His Thr Ser Thr Arg Lys Asn Tyr Leu
 1               5                  10                  15

Ala

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: Antibody MEB037.22C3 CDRL2

<400> SEQUENCE: 56

Trp Ala Ser Thr Arg Glu Ser
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody MEB037.22C3 CDRL3

<400> SEQUENCE: 57

Lys Gln Ser Tyr Asp Val Val Thr
1               5

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody MEB037.22C3; Mature Variable Region

<400> SEQUENCE: 58

Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Leu His Thr
            20                  25                  30

Ser Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asp Val Val Thr Phe Gly Ala Gly Thr Lys Leu Glu Leu Lys
            100                 105                 110

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody MEB037.22C3 CDRH1

<400> SEQUENCE: 59

Ser Tyr Trp Ile His
1               5

<210> SEQ ID NO 60
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody MEB037.22C3 CDRH1

<400> SEQUENCE: 60

Gly Thr Thr Phe Thr Ser Tyr Trp Ile His
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody MEB037.22C3 CDRH2

<400> SEQUENCE: 61

Tyr Ile Asn Pro Ser Ser Gly Tyr His Glu Tyr Asn Gln Lys Phe Ile
1               5                   10                  15

Asp

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody MEB037.22C3 CDRH3

<400> SEQUENCE: 62

Ser Gly Trp Leu Ile His Gly Asp Tyr Tyr Phe Asp Phe
1               5                   10

<210> SEQ ID NO 63
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody MEB037.22C3; Mature Variable Region
<220> FEATURE:
<221> NAME/KEY: MOD_RES
<222> LOCATION: (1)..(1)
<223> OTHER INFORMATION: Gln or pGlu

<400> SEQUENCE: 63

Xaa Val His Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Ile Lys Gln Arg Pro Gly Gln Gly Leu Glu Trp Ile
        35                  40                  45

Gly Tyr Ile Asn Pro Ser Ser Gly Tyr His Glu Tyr Asn Gln Lys Phe
    50                  55                  60

Ile Asp Lys Ala Thr Leu Thr Ala Asp Arg Ser Ser Ser Thr Ala Tyr
65                  70                  75                  80

Met His Leu Thr Ser Leu Thr Ser Glu Asp Ser Ala Val Tyr Tyr Cys
```

```
                    85                  90                  95
Ala Arg Ser Gly Trp Leu Ile His Gly Asp Tyr Tyr Phe Asp Phe Trp
                100                 105                 110

Gly Gln Gly Thr Thr Leu Thr Val Ser Ser
        115                 120

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(32)
<223> OTHER INFORMATION: This sequence may encompass 1-4 'nncgnncg'
      repeats wherein some positions may be absent
<220> FEATURE:
<221> NAME/KEY: modified_base
<222> LOCATION: (1)..(2)
<223> OTHER INFORMATION: a, c, t or g
<220> FEATURE:
<221> NAME/KEY: modified_base
<222> LOCATION: (5)..(6)
<223> OTHER INFORMATION: a, c, t or g
<220> FEATURE:
<221> NAME/KEY: misc_feature
<222> LOCATION: (7)..(8)
<223> OTHER INFORMATION: May or may not be present
<220> FEATURE:
<221> NAME/KEY: modified_base
<222> LOCATION: (9)..(10)
<223> OTHER INFORMATION: a, c, t or g
<220> FEATURE:
<221> NAME/KEY: modified_base
<222> LOCATION: (13)..(14)
<223> OTHER INFORMATION: a, c, t or g
<220> FEATURE:
<221> NAME/KEY: misc_feature
<222> LOCATION: (15)..(16)
<223> OTHER INFORMATION: May or may not be present
<220> FEATURE:
<221> NAME/KEY: modified_base
<222> LOCATION: (17)..(18)
<223> OTHER INFORMATION: a, c, t or g
<220> FEATURE:
<221> NAME/KEY: modified_base
<222> LOCATION: (21)..(22)
<223> OTHER INFORMATION: a, c, t or g
<220> FEATURE:
<221> NAME/KEY: misc_feature
<222> LOCATION: (23)..(24)
<223> OTHER INFORMATION: May or may not be present
<220> FEATURE:
<221> NAME/KEY: modified_base
<222> LOCATION: (25)..(26)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: misc_feature
<222> LOCATION: (31)..(32)
<223> OTHER INFORMATION: May or may not be present
<220> FEATURE:
<223> OTHER INFORMATION: See specification as filed for detailed
      description of substitutions and preferred embodiments

<400> SEQUENCE: 64
nncgnncgnn cgnncgnncg nncgnncgnn cg                                   32

<210> SEQ ID NO 65
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: This sequence may encompass 1-4 'tcgnn' repeats
      wherein some positions may be absent
<220> FEATURE:
<221> NAME/KEY: modified_base
<222> LOCATION: (4)..(5)
<223> OTHER INFORMATION: a, c, t or g
<220> FEATURE:
<221> NAME/KEY: misc_feature
<222> LOCATION: (4)..(5)
<223> OTHER INFORMATION: This region may encompass 0-2 nucleotides
      wherein some positions may be absent
<220> FEATURE:
<221> NAME/KEY: modified_base
<222> LOCATION: (9)..(10)
<223> OTHER INFORMATION: a, c, t or g
<220> FEATURE:
<221> NAME/KEY: misc_feature
<222> LOCATION: (9)..(10)
<223> OTHER INFORMATION: This region may encompass 0-2 nucleotides
      wherein some positions may be absent
<220> FEATURE:
<221> NAME/KEY: modified_base
<222> LOCATION: (14)..(15)
<223> OTHER INFORMATION: a, c, t or g
<220> FEATURE:
<221> NAME/KEY: misc_feature
<222> LOCATION: (14)..(15)
<223> OTHER INFORMATION: This region may encompass 0-2 nucleotides
      wherein some positions may be absent
<220> FEATURE:
<221> NAME/KEY: modified_base
<222> LOCATION: (19)..(20)
<223> OTHER INFORMATION: a, c, t or g
<220> FEATURE:
<221> NAME/KEY: misc_feature
<222> LOCATION: (19)..(20)
<223> OTHER INFORMATION: This region may encompass 0-2 nucleotides
      wherein some positions may be absent
<220> FEATURE:
<223> OTHER INFORMATION: See specification as filed for detailed
      description of substitutions and preferred embodiments

<400> SEQUENCE: 65
tcgnntcgnn tcgnntcgnn                                              20
```

COMBINATION OF A PD-1 ANTAGONIST AND CPG-C TYPE OLIGONUCLEOTIDE FOR TREATING CANCER

CROSS REFERENCES TO RELATED APPLICATIONS

This application is the National Stage of International Application No. PCT/JP2016/034275, filed May 26, 2016, and claims benefit of U.S. Provisional Application Nos. 62/168,449, filed on May 29, 2015 and 62/169,309, filed Jun. 1, 2015.

REFERENCE TO A SEQUENCE LISTING

The instant application contains a sequence listing which has been submitted in ASCII format via EFS-Web and is hereby incorporated by reference in its entirety. Said ASCII copy, created on May 26, 2016, is named 24127_SL.txt and is 65,000 bytes in size.

FIELD OF THE INVENTION

The present invention relates to combination therapies useful for the treatment of cancer. In particular, the invention relates to a combination therapy which comprises an antagonist of a Programmed Death 1 protein (PD-1) and a CpG-C type oligonucleotide, which is a Toll-like receptor 9 (TLR9) agonist.

BACKGROUND OF THE INVENTION

PD-1 is recognized as an important molecule in immune regulation and the maintenance of peripheral tolerance. PD-1 is moderately expressed on naive T, B and NKT cells and up-regulated by TB cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

Administration of certain DNA sequences, generally known as immunostimulatory sequences, induces an immune response with a Th1-type bias as indicated by secretion of Th1-associated cytokines. Administration of an immunostimulatory polynucleotide with an antigen results in a Th1-type immune response to the administered antigen. Roman et al. (1997) Nature Med. 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding 13-Gal and containing an immunostimulatory sequence responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) Proc. Natl. Acad. Sci. USA 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

There is a need in the art to improve the efficacy of cancer immunotherapy. Therefore, it is desirable to explore combination therapy for PD-1 antagonists and immunostimulatory oligonucleotide sequences.

SUMMARY OF THE INVENTION

In one embodiment, the invention provides a method for treating cancer in an individual comprising administering to the individual a combination therapy which comprises a PD-1 antagonist and a TLR9 agonist, wherein the TLR9 agonist is a CpG-C type oligonucleotide.

In another embodiment, the invention provides a medicament comprising a PD-1 antagonist for use in combination with a TLR9 agonist for treating cancer, wherein the TLR9 agonist is a CpG-C type oligonucleotide. In yet another embodiment, the invention provides a medicament comprising a TLR9 agonist for use in combination with a PD-1 antagonist for treating cancer, wherein the TLR9 agonist is a CpG-C type oligonucleotide.

Other embodiments provide use of a PD-1 antagonist in the manufacture of a medicament for treating cancer in an individual when administered in combination with a TLR9 agonist and use of a TLR9 agonist in the manufacture of a medicament for treating cancer in an individual when administered in combination with a PD-1 antagonist. In such embodiments, the TLR9 agonist is a CpG-C type oligonucleotide.

In a still further embodiment, the invention provides use of a PD-1 antagonist and a TLR9 agonist in the manufacture of medicaments for treating cancer in an individual, wherein the TLR9 agonist is a CpG-C type oligonucleotide. In some embodiments, the medicaments comprise a kit, and the kit also comprises a package insert comprising instructions for using the PD-1 antagonist in combination with the TLR9 agonist to treat cancer in an individual.

In a further embodiment, the combination therapy of the methods, medicaments or kits discussed above further comprises an anti-IL-10 antibody.

BRIEF DESCRIPTION OF THE DRAWINGS

FIG. 1 shows amino acid sequences of the light chain and heavy chain CDRs for an exemplary anti-PD-1 monoclonal antibody useful in the present invention (SEQ ID NOs:1-6).

FIG. 2 shows amino acid sequences of the light chain and heavy chain CDRs for another exemplary anti-PD-1 monoclonal antibody useful in the present invention (SEQ ID NOs:7-12).

FIG. 3 shows amino acid sequences of the heavy chain variable region and full length heavy chain for an exemplary anti-PD-1 monoclonal antibody useful in the present invention (SEQ ID NO:13 and SEQ ID NO:14).

FIG. 4 shows amino acid sequences of alternative light chain variable regions for an exemplary anti-PD-1 monoclonal antibody useful in the present invention (SEQ ID NOs:15-17).

FIG. 5 shows amino acid sequences of alternative light chains for an exemplary anti-PD-1 monoclonal antibody useful in the present invention, with FIG. 5A showing the amino acid sequences for the K09A-L-11 and K09A-L-16 light chains (SEQ ID NOs:18 and 19, respectively) and FIG. 5B showing the amino acid sequence for the K09A-L-17 light chain (SEQ ID NO:20).

FIG. 6 shows amino acid sequences of the heavy and light chains for pembrolizumab (SEQ ID NOs. 21 and 22, respectively).

FIG. 7 shows amino acid sequences of the heavy and light chains for nivolumab (SEQ ID NOs. 23 and 24, respectively).

FIG. 8 shows amino acid sequences of anti-IL-10 hum12G8, with light chain sequence of SEQ ID NO: 35 and heavy chain sequence of SEQ ID NO: 34.

FIG. 9 shows amino acid sequences of anti-IL-10 TC40.11D8, with light chain sequence of SEQ ID NO: 37 and heavy chain sequence of SEQ ID NO: 36.

FIG. 12 shows the induction of IFNα2a and IL-10 in human PBMCs (2 donors) with treatment of C59-08 for 24 hours.

FIG. 14C shows the levels of gene expression of various markers of T cell infiltration and activation, while

DETAILED DESCRIPTION

Abbreviations

Figure 10A:
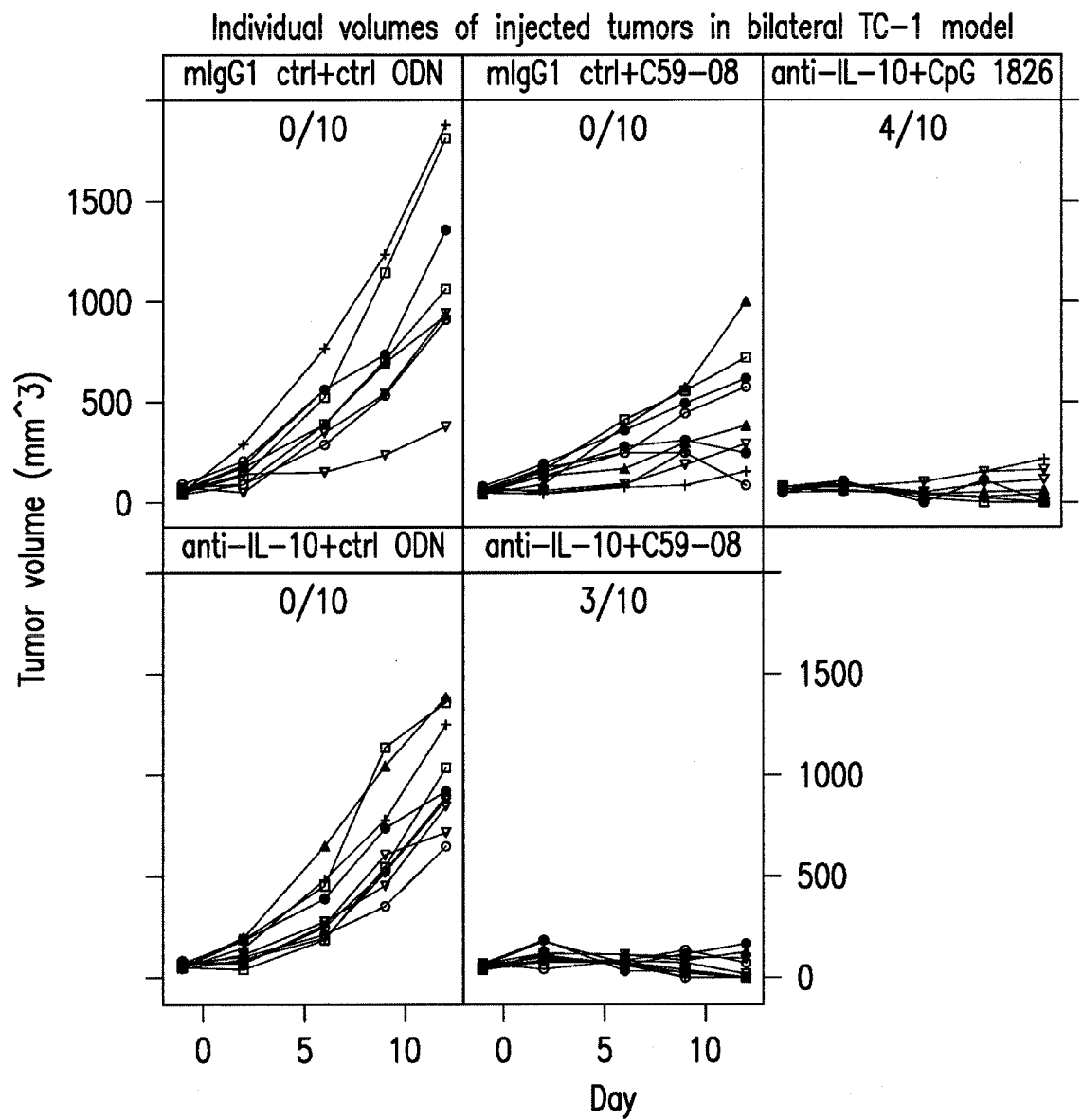
FIG. 10 shows tumor growth of injected tumors in mouse TC-1 bilateral tumor model. Panel A shows volume of injected tumors for individual animals and number of complete regressions (CRs) per group. Panel B shows median volume of injected tumors with error bar indicating 68% confidence interval. Panel C compares volumes of injected tumors between treatment groups by day. Panel D shows unadjusted and multiplicity-adjusted P-values for comparison of volumes of injected tumors between treatments. Unadjusted p value refers to two-sided p-values based on the Peto & Peto version of the Gehan-Breslow nonparametric test statistic for right-censored data. P-values were estimated from 20,000 random reassignments of animals between the two treatments being compared. Multiplicity adjusted p-values refers to p-values adjusted to control the familywise error rate across all time points for a given pair of treatments. Adjustment was by applying the maxT procedure of Westfall and Young to the permutation distributions.

Throughout the detailed description and examples of the invention the following abbreviations will be used:
BOR Best overall response
BID One dose twice daily CBR Clinical Benefit Rate
CDR Complementarity determining region
CHO Chinese hamster ovary
CR Complete Response
DCR Disease Control Rate
DFS Disease free survival
DLT Dose limiting toxicity
DOR Duration of Response
DSDR Durable Stable Disease Rate
FFPE Formalin-fixed, paraffin-embedded
FR Framework region
IgG Immunoglobulin G
IHC Immunohistochemistry or immunohistochemical
irRC Immune related response criteria
IV Intravenous
MTD Maximum tolerated dose
NCBI National Center for Biotechnology Information
NCI National Cancer Institute
ORR Objective response rate
OS Overall survival
PD Progressive disease
PD-1 Programmed Death 1
PD-L1 Programmed Cell Death 1 Ligand 1
PD-L2 Programmed Cell Death 1 Ligand 2
PFS Progression free survival
PR Partial response
Q2W One dose every two weeks
Q3W One dose every three weeks
QD One dose per day
RECIST Response Evaluation Criteria in Solid Tumors
SD Stable disease
VH Immunoglobulin heavy chain variable region
VK Immunoglobulin kappa light chain variable region I. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab)$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Anti-tumor response" when referring to a cancer patient treated with a therapeutic regimen, such as a combination therapy described herein, means at least one positive therapeutic effect, such as for example, reduced number of cancer cells, reduced tumor size, reduced rate of cancer cell infiltration into peripheral organs, reduced rate of tumor metastasis or tumor growth, or progression free survival. Positive therapeutic effects in cancer can be measured in a number of ways (See, W. A. Weber, J. Null. Med. 50:1S-10S (2009); Eisenhauer et al., supra). In some embodiments, an anti-tumor response to a combination therapy described herein is assessed using RECIST 1.1 criteria, bidimentional irRC or unidimensional irRC. In some embodiments, an anti-tumor response is any of SD, PR, CR, PFS, or DFS.

"Bidimensional irRC" refers to the set of criteria described in Wolchok J D, et al. Guidelines for the evaluation of immune therapy activity in solid tumors: immune-related response criteria. *Clin Cancer Res.* 2009; 15(23): 7412-7420. These criteria utilize bidimensional tumor measurements of target lesions, which are obtained by multiplying the longest diameter and the longest perpendicular diameter ($cm^2$) of each lesion.

"Biotherapeutic agent" means a biological molecule, such as an antibody or fusion protein, that blocks ligand/receptor signaling in any biological pathway that supports tumor maintenance and/or growth or suppresses the anti-tumor immune response. Classes of biotherapeutic agents include, but are not limited to, antibodies to VEGF, EGFR, Her2/neu, other growth factor receptors, CD20, CD40, CD-40L, CTLA-4, OX-40, 4-1BB, and ICOS.

The terms "cancer", "cancerous", or "malignant" refer to or describe the physiological condition in mammals that is typically characterized by unregulated cell growth. Examples of cancer include but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. In another embodiment, the cancer is carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Another particular example of cancer includes renal cell carcinoma. Yet another particular example of cancer is non-hodgkin's lymphoma or cutaneous T-cell lymphoma. Yet another particular example of cancer is acute myeloid leukemia (AML) or myelodysplastic syndrome. Cancers that may be treated in accordance with the present invention include those characterized by elevated expression of one or both of PD-L1 and PD-L2 in tested tissue samples.

"CpG-C ONs" or "CpG-C type oligonucleotides" are oligonucleotides from 12 to 100 bases in length, which have one or more 5'-TCG trinucleotides wherein the 5'-T is positioned 0, 1, 2, or 3 bases from the 5'-end of the oligonucleotide, and at least one palindromic sequence of at least 8 bases in length comprising one or more unmethylated CG dinucleotides. The one or more 5'-TCG trinucleotide sequence may be separated from the 5'-end of the palindromic sequence by 0, 1, or 2 bases or the palindromic sequence may contain all or part of the one or more 5'-TCG trinucleotide sequence. In one embodiment, the oligonucleotide is an oligodeoxynucleotide (ODN). In one embodiment, the oligonucleotide is a 2'-oligodeoxynucleotide. CpG-C ODNs have the ability to stimulate B cells, induce plasmacytoid dendritic cell (PDC) maturation and cause secretion of high levels of type I interferons (e.g., IFN-α, IFN-γ, etc.). In some embodiments, the CpG-C ODNs are 12 to 100 bases in length, preferably 12 to 50 bases in length, preferably 12 to 40 bases in length, or preferably 12-30 bases in length. In some embodiments, the ODN is at least (lower limit) 12, 13, 14, 15, 16, 17, 18, 19, 20, 21, 22, 23, 24, 25, 26, 27, 28, 29, 30, 32, 34, 36, 38, 40, 50, 60, 70, 80, or 90 bases in length. In some embodiments, the ODN is at most (upper limit) 100, 90, 80, 70, 60, 50, 49, 48, 47, 46, 45, 44, 43, 42, 41, 40, 39, 38, 37, 36, 35, 34, 33, 32, 31, or 30 bases in length. In some embodiments, the at least one palindromic sequence is 8 to 97 bases in length, preferably 8 to 50 bases in length, or preferably 8 to 32 bases in length. In some embodiments, the at least one palindromic sequence is at least (lower limit) 8, 10, 12, 14, 16, 18, 20, 22, 24, 26, 28, or 30 bases in length. In some embodiments, the at least one palindromic sequence is at most (upper limit) 50, 48, 46, 44, 42, 40, 38, 36, 34, 32, 30, 28, 26, 24, 22, 20, 18, 16, 14, 12 or 10 bases in length. In one embodiment, the oligonucleotide is an oligodeoxynucleotide. In one embodiment, one or more of the internucleotide linkages of the CpG-C ODN are modified linkages. In one embodiment, one or more of the internucleotide linkages of CpG-C ODN are phosphorothioate (PS) linkages. In one embodiment, all of the internucleotide linkages of CpG-C ODN are phosphorothioate (PS) linkages. A phosphorothioate backbone refers to all of the internucleotide linkages of CpG-C ODN being phosphorothioate (PS) linkages.

The CpG-C type ODNs and SEQ ID NO: 38-51 discussed herein are in their pharmaceutically acceptable salt form unless otherwise indicated. Exemplary basic salts include ammonium salts, alkali metal salts such as sodium, lithium, and potassium salts, alkaline earth metal salts such as calcium and magnesium salts, zinc salts, salts with organic bases (for example, organic amines) such as N-Me-D-glucamine, N-[1-(2,3-dioleoyloxy)propyl]-N,N,N-trimethylammonium chloride, choline, tromethamine, dicyclohexylamines, t-butyl amines, and salts with amino acids such as arginine, lysine and the like. In one embodiment, the CpG-C type ODNs are in the ammonium, sodium, lithium, or potassium salt form. In one preferred embodiment, the CpG-C type ODNs are in the sodium salt form. The CpG-C ODN may be provided in a pharmaceutical solution comprising a pharmaceutically acceptable excipient. Alternatively, the CpG-C ODN may provided as a lyophilized solid, which is subsequently reconstituted in sterile water, saline or a pharmaceutically acceptable buffer before administration.

Pharmaceutically acceptable excipients of the present disclosure include for instance, solvents, bulking agents, buffering agents, tonicity adjusting agents, and preservatives (see, e.g., Pramanick et al., Pharma Times, 45:65-77, 2013). In some embodiments the pharmaceutical compositions may comprise an excipient that functions as one or more of a solvent, a bulking agent, a buffering agent, and a tonicity adjusting agent (e.g., sodium chloride in saline may serve as both an aqueous vehicle and a tonicity adjusting agent). The pharmaceutical compositions of the present disclosure are suitable for parenteral administration.

In some embodiments, the pharmaceutical compositions comprise an aqueous vehicle as a solvent. Suitable vehicles include for instance sterile water, saline solution, phosphate buffered saline, and Ringer's solution. In some embodiments, the composition is isotonic.

The pharmaceutical compositions may comprise a bulking agent. Bulking agents are particularly useful when the pharmaceutical composition is to be lyophilized before administration. In some embodiments, the bulking agent is a protectant that aids in the stabilization and prevention of degradation of the active agents during freeze or spray drying and/or during storage. Suitable bulking agents are sugars (mono-, di- and polysaccharides) such as sucrose, lactose, trehalose, mannitol, sorbital, glucose and raffinose.

The pharmaceutical compositions may comprise a buffering agent. Buffering agents control pH to inhibit degradation of the active agent during processing, storage and optionally reconstitution. Suitable buffers include for instance salts comprising acetate, citrate, phosphate or sulfate. Other suitable buffers include for instance amino acids such as arginine, glycine, histidine, and lysine. The buffering agent may further comprise hydrochloric acid or sodium hydroxide. In some embodiments, the buffering agent maintains the pH of the composition within a range of 4 to 9. In some embodiments, the pH is greater than (lower limit) 4, 5, 6, 7 or 8. In some embodiments, the pH is less than (upper limit) 9, 8, 7, 6 or 5. That is, the pH is in the range of from about 4 to 9 in which the lower limit is less than the upper limit.

The pharmaceutical compositions may comprise a tonicity adjusting agent. Suitable tonicity adjusting agents include for instance dextrose, glycerol, sodium chloride, glycerin and mannitol.

The pharmaceutical compositions may comprise a preservative. Suitable preservatives include for instance antioxidants and antimicrobial agents. However, in preferred embodiments, the pharmaceutical composition is prepared under sterile conditions and is in a single use container, and thus does not necessitate inclusion of a preservative.

The term "palindromic sequence" or "palindrome" refers to a nucleic acid sequence that is an inverted repeat, e.g., ABCDD'C'B'A', where the bases, e.g., A, and A', B and B', C and C', D and D', are capable of forming Watson-Crick base pairs. Such sequences may be single-stranded or may form double-stranded structures or may form hairpin loop structures under some conditions. For example, as used herein, "an 8 base palindrome" refers to a nucleic acid sequence in which the palindromic sequence is 8 bases in length, such as ABCDD'C'B'A'. A palindromic sequence may be part of an oligonucleotide that also contains non-palindromic sequences. An oligonucleotide may contain one or more palindromic sequence portions and one or more non-palindromic sequence portions. Alternatively, an oligonucleotide sequence may be entirely palindromic. In an oligonucleotide with more than one palindromic sequence portion, the palindromic sequence portions may or may not overlap with each other.

In one embodiment, the CpG-C ODNs of the present disclosure comprise:

(a) 5'-$N_x$(TCG($N_q$))$_y$$N_w$($X_1X_2$CG$X_2$'$X_1$'(CG)$_p$)$_z$$N_v$ (SEQ ID NO:38) wherein N are nucleosides, x=0, 1, 2 or 3, y=1, 2, 3 or 4, w=0, 1 or 2, p=0 or 1, q=0, 1 or 2, v=0 to 89 and z=1 to 20, $X_1$ and $X_1$' are self-complementary nucleosides, $X_2$ and $X_2$' are self-complementary nucleosides, and wherein the 5'-T of the (TCG($N_q$))$_y$ sequence is 0-3 bases from the 5' end of the oligonucleotide; and (b) a palindromic sequence at least 8 bases in length wherein the palindromic sequence comprises the first ($X_1X_2$CG$X_2$'$X_1$') (SEQ ID NO:55) of the ($X_1X_2$CG$X_2$'$X_1$'(CG)$_p$)$_z$ (SEQ ID NO: 56) sequences, wherein the ODN is from 12 to 100 bases in length. In some embodiments, x=0, y=1, w=0, p=0 or 1, q=0, 1 or 2, v=0 to 20 and z=1, 2, 3 or 4. In some embodiments, $X_1$ and $X_2$ are each either A or T. In some embodiments, the palindromic sequence has a base composition of more than one-third As and Ts. In some embodiments, the CpG-C ODN comprises a sequence selected from the group consisting of SEQ ID NOs:38-51.

In some embodiments, the CpG-C ODNs of the present disclosure consist of TCG$N_q$($X_1X_2$CG$X_2$'$X_1$'CG)$_z$$N_v$ (SEQ ID NO:39), wherein N are nucleosides, q=0, 1, 2, 3, 4, or 5, v=0 to 20, z=1 to 4, $X_1$ and $X_1$' are self-complementary nucleosides, $X_2$ and $X_2$' are self-complementary nucleosides, and wherein the ODN is at least 12 bases in length. In some embodiments, the CpG-C ODN consists of a sequence selected from the group consisting of SEQ ID NOs:38-51.

In some embodiments, the CpG-C ODNs of the present disclosure consist of 5'-TCG$N_q$TTCGAACGTTCGAACGTT$N_s$-3' (SEQ ID NO:40), wherein N are nucleosides, q=0, 1, 2, 3, 4, or 5, s=0 to 20, and wherein the ODN is at least 12 bases in length. In one embodiment, s=0, 1, 2, 3, 4, or 5. In some embodiments, the CpG-C ODN consists of a sequence selected from the group consisting of

```
                                       (SEQ ID NO: 42)
5'-TCGTTCGAACGTTCGAACGTTCGAA-3'
q = 0 and s = 4, (SEQ ID NO: 43)
5'-TCGAACGTTCGAACGTTCGAACGTT-3'
q = 4 and s = 0, (SEQ ID NO: 45)
5'-TCGAACGTTCGAACGTTCGAACGTTCGAAT-3'
q = 4 and s = 5, (SEQ ID NO: 46)
5'-TCGTAACGTTCGAACGTTCGAACGTTA-3'
q = 5 and s = 1,
and
```

```
                                       (SEQ ID NO: 47)
5'-TCGTAACGTTCGAACGTTCGAACGTT-3'
q = 5 and s = 0.
```

In one embodiment, the TLR9 agonist is a CpG-C ODN consisting of the sequence 5'-TCGAACGTTCGAACGTTCGAACGTTCGAAT-3' (SEQ ID NO:45). In another embodiment, the CpG-C ODN is the sodium salt of 5'-TCGAACGTTCGAACGTTCGAACGTTCGAAT-3' (SEQ ID NO:45). In a further embodiment, the CpG-C type oligonucleotide has a sequence that consists of 5'-TCGTTCGAACGTTCGAACGTTCGAA-3' (SEQ ID NO:42). In a further embodiment, the CpG-C type oligonucleotide is a sodium salt of 5'-TCGTTCGAACGTTCGAACGTTCGAA-3' (SEQ ID NO:42).

In another embodiment, the TLR9 agonist CpG-C type oligonucleotide is selected from the group consisting of:

```
                                       (SEQ ID NO: 41)
5'-TCGTCGAACGTTCGAGATGAT-3';

(SEQ ID NO: 42)
5'-TCGTTCGAACGTTCGAACGTTCGAA-3';

(SEQ ID NO: 43)
5'-TCGAACGTTCGAACGTTCGAACGTT-3';

(SEQ ID NO: 44)
5'-TCGAACGTTCGAACGTTCGAATTTT-3';

(SEQ ID NO: 45)
5'-TCGAACGTTCGAACGTTCGAACGTTCGAAT-3';

(SEQ ID NO: 46)
5'-TCGTAACGTTCGAACGTTCGAACGTTA-3';

(SEQ ID NO: 47)
5'-TCGTAACGTTCGAACGTTCGAACGTT-3';

(SEQ ID NO: 48)
5'-TCGTAACGTTCGAACGTTCGAACGT-3';

(SEQ ID NO: 49)
5'-TCGTAACGTTCGAACGTTCGAACG-3';

(SEQ ID NO: 50)
5'-TCGTAACGTTCGAACGTTCGAAC-3';
and (SEQ ID NO: 51)
5'-TCGTAACGTTCGAACGTTCGAA-3'.
```

TABLE 1

Motif and Sequences of CpG-C type oligonucleotides

| Compound # | SEQ ID NO: | Sequence |
|---|---|---|
| C59-01 | 38 | 5'-$N_x$(TCG($N_q$))$_y$$N_w$($X_1X_2$CG$X_2$'$X_1$' (CG)$_p$)$_z$$N_v$-3' |
| C59-02 | 39 | 5'-TCG$N_q$($X_1X_2$CG$X_2$'$X_1$'CG)$_z$$N_v$-3' |
| C59-03 | 40 | 5'-TCG$N_q$TTCGAACGTTCGAACGTT$N_s$-3' |
| C59-04 | 41 | 5'-TCGTCGAACGTTCGAGATGAT-3' |
| C59-05 | 42 | 5'-TCGTTCGAACGTTCGAACGTTCGAA-3' |
| C59-06 | 43 | 5'-TCGAACGTTCGAACGTTCGAACGTT-3' |
| C59-07 | 44 | 5'-TCGAACGTTCGAACGTTCGAATTTT-3' |

TABLE 1-continued

Motif and Sequences of CpG-C type oligonucleotides

| Compound # | SEQ ID NO: | Sequence |
|---|---|---|
| C59-08 | 45 | 5'-TCGAACGTTCGAACGTTCGAACGTTCGAAT-3' |
| C59-09 | 46 | 5'-TCGTAACGTTCGAACGTTCGAACGTTA-3' |
| C59-10 | 47 | 5'-TCGTAACGTTCGAACGTTCGAACGTT-3' |
| C59-11 | 48 | 5'-TCGTAACGTTCGAACGTTCGAACGT-3' |
| C59-12 | 49 | 5'-TCGTAACGTTCGAACGTTCGAACG-3' |
| C59-13 | 50 | 5'-TCGTAACGTTCGAACGTTCGAAC-3' |
| C59-14 | 51 | 5'-TCGTAACGTTCGAACGTTCGAA-3' |

It is understood that, with respect to formulae or sequence motifs described herein, any and all parameters are independently selected. For example, if x=0-2, y may be independently selected regardless of the value of x (or any other selectable parameter in a formula), as long as the total oligonucleotide length limitation is met.

Additional CpG-C oligonucleotides having sequences encompassed by the motifs of the present disclosure are suitable for use in the methods and medicaments disclosed herein. A plurality of additional CpG-C oligonucleotides having sequences encompassed by the motifs of the present disclosure are described in U.S. Pat. Nos. 7,745,606, 8,158,768, and 8,871,732 to Dynavax Technologies Corporation. These sequences are hereby incorporated by reference.

CpG oligonucleotides have been described in the art and their activity may be readily determined using standard assays, which measure various aspects of immune responses (e.g., cytokine secretion, antibody production, NK cell activation, B cell proliferation, T cell proliferation, etc.). Exemplary methods are described in WO 97/28259; WO 98/16247; WO 99/11275, WO 98/55495 and WO 00/61151, as well as U.S. Pat. Nos. 7,745,606, 8,158,768, and 8,871,732 to Dynavax Technologies Corporation. Accordingly, these and other methods can be used to detect and quantify immunomodulatory activity of CpG oligonucleotides.

CpG-C oligonucleotides may contain modifications. Suitable modifications include but are not limited to, modifications of the 3'OH or 5'OH group, modifications of the nucleotide base, modifications of the sugar component, and modifications of the phosphate group. Modified bases may be included in the palindromic sequence as long as the modified base(s) maintains the same specificity for its natural complement through Watson-Crick base pairing (e.g., the palindromic portion of the CpG-C oligonucleotide remains self-complementary).

CpG-C oligonucleotides may be linear, may be circular or include circular portions and/or a hairpin loop. CpG-C oligonucleotides may be single stranded or double stranded. CpG-C oligonucleotides may be DNA, RNA or a DNA/RNA hybrid.

CpG-C oligonucleotides may contain naturally-occurring or modified, non-naturally occurring bases, and may contain modified sugar, phosphate, and/or termini. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. In some embodiments, CpG-C oligonucleotides have only phosphorothioate linkages, only phosphodiester linkages, or a combination of phosphodiester and phosphorothioate linkages.

Sugar modifications known in the field, such as 2'-alkoxy-RNA analogs, 2'-amino-RNA analogs, 2'-fluoro-DNA, and 2'-alkoxy- or amino-RNA/DNA chimeras and others described herein, may also be made and combined with any phosphate modification. Examples of base modifications include but are not limited to addition of an electron-withdrawing moiety to C-5 and/or C-6 of a cytosine of the CpG-C oligonucleotide (e.g., 5-bromocytosine, 5-chlorocytosine, 5-fluorocytosine, 5-iodocytosine) and C-5 and/or C-6 of a uracil of the CpG-C oligonucleotide (e.g., 5-bromouracil, 5-chlorouracil, 5-fluorouracil, 5-iodouracil). As noted above, use of a base modification in a palidromic sequence of a CpG-C oligonucleotide should not interfere with the self-complementarity of the bases involved for Watson-Crick base pairing. However, outside of a palindromic sequence, modified bases may be used without this restriction. For instance, 2'-O-methyl-uridine and 2'-O-methyl-cytidine may be used outside of the palindromic sequence, whereas, 5-bromo-2'-deoxycytidine may be used both inside and outside the palindromic sequence. Other modified nucleotides, which may be employed both inside and outside of the palindromic sequence include 7-deaza-8-aza-dG, 2-amino-dA, and 2-thio-dT.

Duplex (i.e., double stranded) and hairpin forms of most oligonucleotides are in dynamic equilibrium, with the hairpin form generally favored at low oligonucleotide concentration and higher temperatures. Covalent interstrand or intrastrand cross-links increase duplex or hairpin stability, respectively, towards thermal-, ionic-, pH-, and concentration-induced conformational changes. Chemical cross-links can be used to lock the polynucleotide into either the duplex or the hairpin form for physicochemical and biological characterization. Cross-linked oligonucleotides that are conformationally homogeneous and are "locked" in their most active form (either duplex or hairpin form) could potentially be more active than their uncross-linked counterparts. Accordingly, some CpG-C oligonucleotides of the present disclosure contain covalent interstrand and/or intrastrand cross-links.

A variety of ways to chemically cross-link duplex DNA are known in the art. Any cross-linking method may be used as long as the cross-linked polynucleotide product possesses the desired immunomodulatory activity. One method, for example, results in a disulfide bridge between two opposing thymidines at the terminus of the duplex or hairpin. For this cross-linking method, the oligonucleotide(s) of interest is synthesized with a 5'-DMT-N3-(tBu-SS-ethyl)thymidine-3'-phosphoramidite ("T*"). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods and others are described in the art (see, e.g., Glick et al., J Org Chem, 56:6746-6747, 1991, Glick et al., J Am Chem Soc, 114:5447-5448, 1992, Goodwin et al., Tetrahedron Letters 35:1647-1650, 1994, Wang et al., J Am Chem Soc, 117:2981-2991, 1995, Osborne et al., Bioorganic & Medicinal Chemistry Letters, 6:2339-2342, 1996 and Osborne et al., J Am Chem Soc, 118:11993-12003, 1996).

Another cross-linking method forms a disulfide bridge between offset residues in the duplex or hairpin structure. For this cross-linking method, the oligonucleotide(s) of interest is synthesized with convertible nucleosides (commercially available, for example, from Glen Research). This method utilizes, for example, an A-A disulfide or a C-A disulfide bridge and linkages through other bases are also possible. To form the disulfide-modified polynucleotide, the polynucleotide containing the convertible nucleoside is reacted with cystamine (or other disulfide-containing amine). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods are described in the art (see, e.g., Ferentz et al., J Am Chem Soc, 113:4000-4002, 1991, and Ferentz et al., J Am Chem Soc, 115:9006-9014, 1993).

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases (see, e.g., Beaucage "Oligodeoxyribonucleotide Synthesis" in Protocols for Oligonucleotides and Analogs, Synthesis and Properties (Agrawal, ed.) Humana Press, Totowa, N.J., 1993; Warner et al., DNA 3:401, 1984 and U.S. Pat. No. 4,458,066).

The CpG-C oligonucleotide may contain phosphate-modified oligonucleotides, some of which are known to stabilize the oligonucleotide. Accordingly, some embodiments include stabilized CpG-C oligonucleotides. Synthesis of oligonucleotides containing modified phosphate linkages or non-phosphate linkages is also known in the art (see, e.g., Matteucci "Oligonucleotide Analogs: an Overview" in Oligonucleotides as Therapeutic Agents, (D. J. Chadwick and G. Cardew, ed.) John Wiley and Sons, New York, N.Y., 1997). The phosphorous derivative (or modified phosphate group), which can be attached to the sugar or sugar analog moiety in the oligonucleotide, can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, has already been well described (see, e.g., Peyrottes et al., Nucleic Acids Res, 24:1841-1848, 1996; Chaturvedi et al., Nucleic Acids Res, 24:2318-2323, 1996; and Schultz et al., Nucleic Acids Res, 24:2966-2973, 1996). For example, synthesis of phosphorothioate oligonucleotides is similar to that described above for naturally occurring oligonucleotides except that the oxidation step is replaced by a sulfurization step (Zon "Oligonucleoside Phosphorothioates" in Protocols for Oligonucleotides and Analogs, Synthesis and Properties (Agrawal, ed.) Humana Press, pp. 165-190, 1993).

CpG-C oligonucleotides can comprise one or more ribonucleotides (containing ribose as the only or principal sugar component), deoxyribonucleotides (containing deoxyribose as the principal sugar component), modified sugars or sugar analogs. Thus, in addition to ribose and deoxyribose, the sugar moiety can be pentose, deoxypentose, hexose, deoxyhexose, glucose, arabinose, xylose, lyxose, and a sugar analog cyclopentyl group. The sugar can be in pyranosyl or in a furanosyl form. In the CpG-C oligonucleotide, the sugar moiety is preferably the furanoside of ribose, deoxyribose, arabinose or 2'-0-alkylribose, and the sugar can be attached to the respective heterocyclic bases either in anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification in the CpG-C oligonucleotide includes, but is not limited to, 2'-O-methyluridine and 2'-O-methyl-cytidine. The preparation of these sugars or sugar analogs and the respective nucleosides wherein such sugars or analogs are attached to a heterocyclic base (nucleic acid base) per se is known, and therefore need not be described here. Sugar modifications may also be made and combined with any phosphate modification in the preparation of a CpG-C oligonucleotide.

The heterocyclic bases, or nucleic acid bases, which are incorporated in the CpG-C oligonucleotide can be the naturally-occurring principal purine and pyrimidine bases, (namely uracil, thymine, cytosine, adenine and guanine, as mentioned above), as well as naturally-occurring and synthetic modifications of said principal bases. Thus, a CpG-C oligonucleotide may include one or more of inosine, 2'-deoxyuridine, and 2-amino-2'-deoxyadenosine.

"CBR" or "Clinical Benefit Rate" means CR+PR+durable SD.

"CDR" or "CDRs" as used herein means complementarity determining region(s) in a immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, and anti-sense oligonucleotides that inhibit expression of genes implicated in abnormal cell proliferation or tumor growth. Chemotherapeutic agents useful in the treatment methods of the present invention include cytostatic and/or cytotoxic agents.

"Chothia" as used herein means an antibody numbering system described in Al-Lazikani et al., *JMB* 273:927-948 (1997).

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 2 below.

TABLE 2

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antagonist that consists essentially of a recited amino acid sequence may also include one or more amino acids, including substitutions of one or more amino acid residues, which do not materially affect the properties of the binding compound.

"DCR" or "Disease Control Rate" means CR+PR+SD.

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide The terms "PD-L" and "mature PD-L" are used interchangeably herein, and shall be understood to mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 of the following sequence:

```
                                        (SEQ ID NO: 25)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

-continued
HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.
```

Specific examples of diagnostic anti-human PD-L1 mAbs useful as diagnostic mAbs for immunohistochemistry (IHC) detection of PD-L1 expression in formalin-fixed, paraffin-embedded (FFPE) tumor tissue sections are antibody 20C3 and antibody 22C3, which are described in the copending international patent application PCT/US13/075932, filed 18 Dec. 2013 and published as WO2014/100079 on 26 Jun. 2014. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P.R. China; Catalog number 10084-R015).

"Anti-IL-10 antibody" means an antagonist antibody that binds IL-10 to inhibit the activity of IL-10. Alternative names or synonyms for IL-10 include: Interleukin-10, cytokine synthesis inhibitor factor or CSIF. Human IL-10 amino acid sequences can be found in U.S. Pat. No. 6,217,857. The amino acid sequence of the mature human IL-10 protein is

```
                                        (SEQ ID NO: 52)
SPGQGTQSENSCTHFPGNLPNMLRDLRDAFSRVKTFFQMKDQLDNLLLK

ESLLEDFKGYLGCQALSEMIQFYLEEVMPQAENQDPDIKAHVNSLGENL

KTLRLRLRRCHRFLPCENKSKAVEQVKNAFNKLQEKGIYKAMSEFDIFI

NYIEAYMTMKIRN
```

Anti-IL-10 antibodies useful in any of the treatment method, medicaments and uses of the present invention include a monoclonal antibody (mAb), or antigen binding fragment thereof, which specifically binds to IL-10, and preferably specifically binds to human IL-10. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

In some preferred embodiments of the treatment method, medicaments and uses of the present invention, the anti-IL-10 antibody is a monoclonal antibody, or antigen binding fragment thereof, which comprises: (a) light chain CDRs of SEQ ID NOs: 26, 27 and 28 and heavy chain CDRs SEQ ID NOs: 29, 30 and 31 of anti-IL-10 hum12G8.

In other preferred embodiments of the treatment method, medicaments and uses of the present invention, the anti-IL-10 antibody is a monoclonal antibody, or antigen binding fragment thereof, which specifically binds to human IL-10 and comprises (a) a heavy chain variable region comprising SEQ ID NO:32 or a variant thereof, and (b) a light chain variable region comprising an amino acid sequence selected from the group consisting of SEQ ID NO:33 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

Table 3 below provides a list of the amino acid sequences of exemplary anti-IL-10 mAbs for use in the treatment method, medicaments and uses of the present invention, and the sequences are shown in FIGS. 8-9.

TABLE 3

EXEMPLARY ANTI-HUMAN IL-10 MONOCLONAL ANTIBODIES

A. Comprises light and heavy chain CDRs of hum12G8 in U.S. Pat. No. 7662379

| | | |
|---|---|---|
| CDRL1 | SEQ ID NO: 26 | KTSQNIFENLA |
| CDRL2 | SEQ ID NO: 27 | YNASPLQA |
| CDRL3 | SEQ ID NO: 28 | HQYYSGYT |
| CDRH1 | SEQ ID NO: 29 | GFTFSDYHMA |
| CDRH2 | SEQ ID NO: 30 | SITLDATYTYYRDSVRG |
| CDRH3 | SEQ ID NO: 31 | HRGFSVWLDY |

B. Comprises the heavy chain variable region and light chain variable regions of hum12G8 in U.S. Pat. No. 7662379

| | | |
|---|---|---|
| Heavy chain VR | SEQ ID NO: 32 | QVQLVESGGGVVQPGRSLRLSCAASGFTFSDYHMAWVRQAPGKGLEWVAS ITLDATYTYYRDSVRGRFTISRDNSKNTLYLQMNSLRAEDTAVYYCARHR GFSVWLDYWGQGTLVTVSSA |
| Light chain VR | SEQ ID NO: 33 | DIQMTQSPSSLSASVGDRVTITCKTSQNIFENLAWYQQKPGKAPKLLIYN ASPLQAGVPSRFSGSGSGTDFTLTISSLQPEDFATYYCHQYYSGYTFGPG TKLELKRTVAA |

C. Comprises the heavy chain and light chain of hum12G8 in U.S. Pat. No. 7662379

| | |
|---|---|
| Heavy chain | SEQ ID NO: 34 |
| Light chain | SEQ ID NO: 35 |

D. Comprises the heavy chain and light chain of TC40.11D8 in U.S. Pat. No. 8226947

| | |
|---|---|
| Heavy chain | SEQ ID NO: 36 |
| Light chain | SEQ ID NO: 37 |

As used herein, an "anti-IL-10 hum 12G8 variant" means a monoclonal antibody which comprises heavy chain and light chain sequences that are identical to those in anti-IL-10 hum 12G8, except for having three, two or one conservative amino acid substitutions at positions that are located outside of the light chain CDRs and six, five, four, three, two or one conservative amino acid substitutions that are located outside of the heavy chain CDRs, e.g., the variant positions are located in the FR regions or the constant region. In other words, anti-IL-10 hum 12G8 and an anti-IL-10 hum 12G8 variant comprise identical CDR sequences, but differ from each other due to having a conservative amino acid substitution at no more than three or six other positions in their full length light and heavy chain sequences, respectively. An anti-IL-10 hum 12G8 variant is substantially the same as anti-IL-10 hum 12G8 with respect to the following properties: binding affinity to IL-10 and neutralizing effect in vivo.

"DSDR" or "Durable Stable Disease Rate" means SD for ≥23 weeks.

"Framework region" or "FR" as used herein means the immunoglobulin variable regions excluding the CDR regions.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Non-responder patient", when referring to a specific anti-tumor response to treatment with a combination therapy described herein, means the patient did not exhibit the anti-tumor response.

"ORR" or "objective response rate" refers in some embodiments to CR+PR, and $ORR_{(week\ 24)}$ refers to CR and PR measured using irRECIST in each patient in a cohort after 24 weeks of treatment with CpG-C type oligonucleotide in combination with pembrolizumab.

"Patient" or "subject" refers to any single subject for which therapy is desired or that is participating in a clinical trial, epidemiological study or used as a control, including humans and mammalian veterinary patients such as cattle, horses, dogs, and cats.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in the treatment method, medicaments and uses of the present invention include: pembrolizumab (also known as MK-3475), a humanized IgG4 mAb with the structure described in WHO Drug Information, Vol. 27, No. 2, pages 161-162 (2013) and which comprises the heavy and light chain amino acid sequences shown in FIG. 6; nivolumab (BMS-936558), a human IgG4 mAb with the structure described in WHO Drug Information, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by MedImmune.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

In some preferred embodiments of the treatment method, medicaments and uses of the present invention, the PD-1 antagonist is a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In other preferred embodiments of the treatment method, medicaments and uses of the present invention, the PD-1 antagonist is a monoclonal antibody, or antigen binding fragment thereof, which specifically binds to human PD-1 and comprises (a) a heavy chain variable region comprising SEQ ID NO:13 or a variant thereof, and (b) a light chain variable region comprising an amino acid sequence selected from the group consisting of SEQ ID NO:15 or a variant thereof; SEQ ID NO:16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

In another preferred embodiment of the treatment method, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO:18, SEQ ID NO:19 or SEQ ID NO:20.

In yet another preferred embodiment of the treatment method, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO:18.

In all of the above treatment method, medicaments and uses, the PD-1 antagonist inhibits the binding of PD-L1 to PD-1, and preferably also inhibits the binding of PD-L2 to PD-1. In some embodiments of the above treatment method, medicaments and uses, the PD-1 antagonist is a monoclonal antibody, or an antigen binding fragment thereof, which specifically binds to PD-1 or to PD-L1 and blocks the binding of PD-L1 to PD-1. In one embodiment, the PD-1 antagonist is an anti-PD-1 antibody which comprises a heavy chain and a light chain, and wherein the heavy and light chains comprise the amino acid sequences shown in FIG. 6 (SEQ ID NO:21 and SEQ ID NO:22).

Table 4 below provides a list of the amino acid sequences of exemplary anti-PD-1 mAbs for use in the treatment method, medicaments and uses of the present invention, and the sequences are shown in FIGS. 1-5.

TABLE 4

EXEMPLARY ANTI-HUMAN PD-1 MONOCLONAL ANTIBODIES

A. Comprises light and heavy chain CDRs of hPD-1.08A in WO2008/156712

| | |
|---|---|
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |

B. Comprises light and heavy chain CDRs of hPD-1.09A in WO2008/156712

| | |
|---|---|
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |

C. Comprises the mature h109A heavy chain variable region and one of the mature K09A light chain variable regions in WO2008/156712

| | |
|---|---|
| Heavy chain VR | SEQ ID NO: 13 |
| Light chain VR | SEQ ID NO: 15 or SEQ ID NO: 16 or |

| SEQ ID NO: | Description |
|---|---|
| 1 | hPD-1.08A light chain CDR1 |
| 2 | hPD-1.08A light chain CDR2 |
| 3 | hPD-1-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | Pembrolizumab Heavy chain |
| 22 | Pembrolizamub Light chain |
| 23 | Nivolumab Heavy chain |
| 24 | Nivolumab light chain |

TABLE 6

Characteristics of Monoclonal Antibody MEB037.22C3

| Antibody Feature | Amino Acid Sequence | SEQ ID NO |
|---|---|---|
| Light Chain | | |
| CDRL1 | KSSQSLLHTSTRKNYLA | 55 |
| CDRL2 | WASTRES | 56 |
| CDRL3 | KQSYDVVT | 57 |
| Mature Variable Region | DIVMSQSPSSLAVSAGEKVTMTCKSSQSLLHTSTRKNYLAWYQ QKPGQSPKLLIYWASTRESGVPDRFTGSGSGTDFTLTISSVQAE DLAVYYCKQSYDVVTFGAGTKLELK | 58 |
| Heavy Chain | | |
| CDRH1 Kabat Defn | SYWIH | 59 |
| CDRH1 Chothia Defn | GTTFTSYWIH | 60 |
| CDRH2 | YINPSSGYHEYNQKFID | 61 |
| CDRH3 | SGWLIHGDYYFDF | 62 |
| Mature Variable Region | XVHLQQSGAELAKPGASVKMSCKASGYTFTSYWIHWIKQRPG QGLEWIGYINPSSGYHEYNQKFIDKATLTADRSSSTAYMHLTSL TSEDSAVYYCARSGWLIHGDYYFDFWGQGTTLTVSS, wherein X = Q or pE | 63 |

TABLE 4-continued

EXEMPLARY ANTI-HUMAN PD-1 MONOCLONAL ANTIBODIES

SEQ ID NO: 17

D. Comprises the mature 409 heavy chain and one of the mature K09A light chains in WO2008/156712

| | |
|---|---|
| Heavy chain | SEQ ID NO: 14 |
| Light chain | SEQ ID NO: 18 or SEQ ID NO: 19 or SEQ ID NO: 20 |

Table 5 provides a brief description of the PD-1 antagonist sequences in the sequence listing.

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, or 30% greater than in the control.

As used herein, a "pembrolizumab variant" means a monoclonal antibody which comprises heavy chain and light chain sequences that are identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g., the variant positions are located in the FR regions or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

"RECIST 1.1 Response Criteria" as used herein means the definitions set forth in Eisenhauer et al., E. A. et al., *Eur. J Cancer* 45:228-247 (2009) for target lesions or nontarget lesions, as appropriate based on the context in which response is being measured.

"Responder patient" when referring to a specific anti-tumor response to treatment with a combination therapy described herein, means the patient exhibited the anti-tumor response.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" cancer as used herein means to administer a combination therapy of a PD-1 antagonist and CpG-C type oligonucleotide to a subject having cancer, or diagnosed with cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, response to a combination therapy described herein is assessed using RECIST 1.1 criteria or irRC (bidimensional or unidimensional) and the treatment achieved by a combination of the invention is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some embodiments, response to a combination of the invention is any of PR, CR, PFS, DFS, OR and OS that is assessed using RECIST 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

The terms "treatment regimen", "dosing protocol" and "dosing regimen" are used interchangeably to refer to the dose and timing of administration of each therapeutic agent in a combination of the invention.

"Tumor" as it applies to a subject diagnosed with, or suspected of having, cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone marrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MM) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Unidimensional irRC refers to the set of criteria described in Nishino M, Giobbie-Hurder A, Gargano M, Suda M, Ramaiya N H, Hodi F S. Developing a Common Language for Tumor Response to Immunotherapy: Immune-related Response Criteria using Unidimensional measurements. *Clin Cancer Res.* 2013; 19(14):3936-3943). These criteria utilize the longest diameter (cm) of each lesion.

"Variable regions" or "V region" as used herein means the segment of IgG chains which is variable in sequence between different antibodies. It extends to Kabat residue 109 in the light chain and 113 in the heavy chain.

In some embodiments of the above treatment method, medicaments and uses of the invention, the individual is a human and the cancer is a solid tumor and in some embodiments, the solid tumor is bladder cancer, breast cancer, clear cell kidney cancer, squamous cell carcinoma of head and neck, lung squamous cell carcinoma, malignant melanoma, non-small-cell lung cancer (NSCLC), ovarian cancer, pancreatic cancer, prostate cancer, renal cell cancer (RCC), small-cell lung cancer (SCLC) or triple negative breast cancer. In some embodiments, the cancer is NSCLC, endometrial cancer, urothelial cancer, squamous cell carcinoma of head and neck or melanoma.

In other embodiments of the above treatment method, medicaments and uses of the invention, the individual is a human and the cancer is a heme malignancy and in some embodiments, the heme malignancy is acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), cutaneous T-cell lymphoma, non-Hodgkin's lymphoma (NHL), or small lymphocytic lymphoma (SLL).

Also, in some embodiments of any of the above treatment method, medicaments and uses, the cancer tests positive for the expression of one or both of PD-L1 and PD-L2. In still other embodiments, the cancer has elevated PD-L1 expression.

In one embodiment of the above treatment method, medicaments and uses, the individual is a human, the cancer tests positive for human PD-L1 and is selected from the group consisting of NSCLC, endometrial cancer, urothelial cancer, squamous cell carcinoma of head and neck or melanoma. In one embodiment of the above treatment method, medicaments and uses, the individual is a human, the cancer tests positive for human PD-L1 and is advanced or metastatic melanoma.

II. Methods, Uses and Medicaments

In one aspect of the invention, the invention provides a method for treating cancer in an individual comprising administering to the individual a combination therapy which comprises a PD-1 antagonist and CpG-C type oligonucleotide.

The combination therapy may also comprise one or more additional therapeutic agents. The additional therapeutic agent may be, e.g., a chemotherapeutic other than CpG-C type oligonucleotide, a biotherapeutic agent, an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF). The specific dosage and dosage schedule of the additional therapeutic agent can further vary, and the optimal dose, dosing schedule and route of administration will be determined based upon the specific therapeutic agent that is being used. In one embodiment, the biotherapeutic agent is anti-IL-10 antibody or antigen-binding fragment thereof.

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, the CpG-C type oligonucleotide is administered before administration of the PD-1 antagonist, while in other embodiments, the CpG-C type oligonucleotide is administered after administration of the PD-1 antagonist. In another embodiment, the CpG-C type oligonucleotide is administered concurrently with the PD-1 antagonist.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each small molecule therapeutic agent in a combination therapy of the invention can be administered orally or parenterally, including the intravenous, intramuscular, intraperitoneal, subcutaneous, rectal, topical, and transdermal routes of administration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced.

A combination therapy of the invention is typically used to treat a tumor that is large enough to be found by palpation or by imaging techniques well known in the art, such as Mill, ultrasound, or CAT scan.

A combination therapy of the invention is preferably administered to a human patient who has a cancer that tests positive for PD-L1 expression. In some preferred embodiments, PD-L1 expression is detected using a diagnostic anti-human PD-L1 antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-1 antagonist and the CpG-C type oligonucleotide, but it is envisioned that the physician could order the first or subsequent diagnostic tests at any time after initiation of treatment, such as for example after completion of a treatment cycle.

Selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human PD-1 mAb as the PD-1 antagonist in the combination therapy, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist in the combination therapy, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein.

In one preferred embodiment of the invention, the PD-1 antagonist in the combination therapy is nivolumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another preferred embodiment of the invention, the PD-1 antagonist in the combination therapy is pembrolizumab, or a pembrolizumab variant, which is administered in a liquid medicament at a dose selected from the group consisting of 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, 10 mg Q3W and flat-dose equivalents of any of these doses, i.e., such as 200 mg Q3W. In some embodiments, pembrolizumab is provided as a liquid medicament which comprises 25 mg/ml pembrolizumab, 7% (w/v) sucrose, 0.02% (w/v) polysorbate 80 in 10 mM histidine buffer pH 5.5.

In some embodiments, the selected dose of pembrolizumab is administered by IV infusion. In one embodiment, the selected dose of pembrolizumab is administered by IV infusion over a time period of between 25 and 40 minutes, or about 30 minutes.

In one embodiment of the invention, the CpG-C type oligonucleotide in the combination therapy has the sequence of SEQ ID NO: 45. However, other CpG-C type oligonucleotides having the motifs and sequences described herein are also suitable for use in the combination therapies of the present invention. Therefore it should be understood, that any description pertaining to the methods or medicaments comprising the CpG-C type oligonucleotide of SEQ ID NO:45 is also applicable to other CpG-C type oligonucleotides, particularly C59-01-C59-14 (SEQ ID NOs: 38-51). For the sake of brevity, this understanding will not be repeated throughout. In one embodiment of the invention, the CpG-C type oligonucleotide in the combination therapy has the sequence of SEQ ID NO: 45, and is administered intratumorally at a dose of from 0.1 to 16.0 mg once a week, preferably 0.1, 0.5, 1.0, 2.0, 3.0, 4.0, 5.0, 6.0, 7.0 or 8.0 mg once a week. In another embodiment of the invention, the oligonucleotide of SEQ ID NO: 45 is administered intratumorally at a dose of from 0.1 to 16.0 mg once a week for four weeks, preferably 0.1, 0.5, 1.0, 2.0, 3.0, 4.0, 6.0, 7.0, or 8.0 mg once a week for four weeks. In a further embodiment of the invention, the oligonucleotide of SEQ ID NO: 45 is administered intratumorally at a dose from 0.1 to 16.0 mg once every three weeks, preferably 0.1, 0.5, 1.0, 2.0, 3.0, 4.0, 6.0, 7.0, or 8.0 mg once every three weeks. In another embodiment of the invention, the oligonucleotide of SEQ ID NO: 45 is administered intratumorally at a dose of 2.0, 4.0 or 8.0 mg once a week for four weeks. In yet another embodiment of the invention, the oligonucleotide of SEQ ID NO: 45 is administered intratumorally at a dose of 2.0, 4.0 or 8.0 mg once a week for four weeks, followed by once every three weeks. In one embodiment, the oligonucleotide of SEQ ID NO: 45 is administered until progression or for up to 12-24 weeks after the first dose. In another embodiment, the oligonucleotide of SEQ ID NO: 45 is administered for a total of 4, 5, 6, 7 or 8 doses. In some embodiments, the CpG-C type oligonucleotide of SEQ ID NO:45 is administered twice weekly, once weekly, biweekly, once every three weeks, once a month, or bimonthly.

The optimal dose for pembrolizumab in combination with CpG-C type oligonucleotide may be identified by dose escalation or dose de-escalation of one or both of these agents. In an embodiment, pembrolizumab is administered at 200 mg Q3W and the oligonucleotide of SEQ ID NO: 45 is intratumorally administered at a dose of from 1 to 16 mg once a week, preferably 1.0, 2.0, 4.0, 8.0 or 16.0 mg once a week. In one embodiment, a patient is treated with 200 mg of pembrolizumab Q3W on Day 1 and treated with the oligonucleotide of SEQ ID NO: 45 administered intratumorally at a dose from 1 to 16 mg on Day 1, preferably 1.0, 2.0, 4.0, 8.0 or 16.0 mg on Day 1, once a week for four weeks, followed by a dose of from 1 to 16 mg, preferably 1.0, 2.0, 4.0, 8.0 or 16.0 mg once every three weeks. In one embodiment, the oligonucleotide of SEQ ID NO: 45 is administered until progression or for up to 24 weeks after the first dose. In a further embodiment, the oligonucleotide of SEQ ID NO: 45 is administered intratumorally at a dose of from 1 to 16 mg, preferably 1.0, 2.0, 4.0, 8.0 or 16.0 mg on Day 1, once a week for four weeks, followed by a dose of from 1 to 16 mg, preferably 1.0, 2.0, 4.0, 8.0 or 16.0 mg once every three weeks for nine weeks. In another embodiment, the oligonucleotide of SEQ ID NO: 45 is administered until progression or for up to 24 weeks after the first dose. In an embodiment, the patient is confirmed to have progressive disease while receiving prior anti-PD-1 therapy. In another embodiment, pembrolizumab is administered intravenously and administered until progression or up to 45 weeks.

In another embodiment, a patient is treated with 200 mg of pembrolizumab Q3W on Day 1 and treated with the oligonucleotide of SEQ ID NO: 45 intratumorally at a dose of from 1 to 16 mg, preferably 1.0, 2.0, 4.0, 8.0 or 16.0 mg on Day 22 once a week for four weeks, followed by a dose of from 1 to 16 mg, preferably 1.0, 2.0, 4.0, 8.0 or 16.0 mg once every three weeks. In a further embodiment, the oligonucleotide of SEQ ID NO: 45 is administered intratumorally at a dose of from 1 to 16 mg, preferably 1.0, 2.0, 4.0, 8.0 or 16.0 mg on Day 1 once a week for four weeks, followed by a dose of from 1 to 16 mg, preferably 1.0, 2.0, 4.0, 8.0 or 16.0 mg once every three weeks for nine weeks. In an embodiment, the patient is anti-PD-1/L1 treatment naive. In another embodiment, pembrolizumab is administered intravenously. In another embodiment, pembrolizumab is administered intravenously and administered until progression or for up to 45 weeks.

In some embodiments, the patient is treated with the combination therapy for at least 24 weeks, e.g., eight 3-week cycles. In some embodiments, treatment with the combination therapy continues until the patient exhibits evidence of PD or a CR.

In a further aspect of the invention, the combination therapy which comprises a PD-1 antagonist and a CpG-C type oligonucleotide further comprises an anti-IL-10 antibody. In one embodiment of the invention, the anti-IL-10 antibody in the combination therapy is anti-IL 10 hum 12G8, which is administered intravenously at a dose selected from the group consisting of: 1 mg/kg Q3W, 2 mg/kg Q3W, 3 mg/kg Q3W, 4 mg/kg Q3W, 5 mg/kg Q3W, 6 mg/kg Q3W, 7 mg/kg Q3W, 8 mg/kg Q3W, 9 mg/kg Q3W, 10 mg/kg Q3W, 11 mg/kg Q3W, 12 mg/kg Q3W, 13 mg/kg Q3W, 14 mg/kg Q3W and 15 mg/kg Q3W. In another embodiment of the invention, the anti-IL-10 antibody in the combination therapy is anti-IL-10 hum 12G8, which is administered intravenously at a dose of 1 mg/kg Q3W. In a further embodiment of the invention, the anti-IL-10 antibody in the combination therapy is anti-IL 10 hum 12G8, which is administered intravenously at a dose of 3 mg/kg Q3W. In yet another embodiment of the invention, the anti-IL-10 antibody in the combination therapy is anti-IL 10 hum 12G8, which is administered intravenously at a dose of 10 mg/kg Q3W.

In a preferred embodiment of the invention, the anti-IL-10 antibody in the combination therapy is anti-IL-10 hum 12G8, or an anti-IL-10 hum 12G8 variant, which is administered in a liquid medicament at a dose selected from the group consisting of 1 mg/kg Q3W, 2 mg/kg Q3W, 3 mg/kg Q3W, 4 mg/kg Q3W, 5 mg/kg Q3W, 6 mg/kg Q3W, 7 mg/kg Q3W, 8 mg/kg Q3W, 9 mg/kg Q3W, 10 mg/kg Q3W, 11 mg/kg Q3W, 12 mg/kg Q3W, 13 mg/kg Q3W, 14 mg/kg Q3W and 15 mg/kg Q3W.

In some embodiments, the patient is selected for treatment with the combination therapy of the invention if the patient has been diagnosed with NSCLC, RCC, endometrial cancer, urothelial cancer, squamous cell carcinoma of head and neck or melanoma.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising pembrolizumab that are suitable for use in the present invention. In some embodiments, a medicament comprising pembrolizumab is provided in a glass vial which contains about 100 mg of pembrolizumab in 4 ml of solution. Each 1 mL of solution contains 25 mg of pembrolizumab and is formulated in: L-histidine (1.55 mg), polysorbate 80 (0.2 mg), sucrose (70 mg), and Water for Injection, USP. The solution requires dilution for IV infusion.

The present invention also provides a medicament which comprises a TLR9 agonist and a pharmaceutically acceptable excipient, wherein the TLR9 agonist is a CpG-C type oligonucleotide. The CpG-C type oligonucleotide may be reconstituted in a physiological buffer for intratumoral injection.

The medicaments described herein may be provided as a kit which comprises a first container and a second container and a package insert. The first container contains at least one dose of a medicament comprising a PD-1 antagonist, the second container contains at least one dose of a medicament comprising CpG-C type oligonucleotide, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some preferred embodiments of the kit, the PD-1 antagonist is an anti-PD-1 antibody and the instructions state that the medicaments are intended for use in treating a patient having a cancer that tests positive for PD-L1 expression by an IHC assay.

These and other aspects of the invention, including the exemplary specific embodiments listed below, will be apparent from the teachings contained herein.

Exemplary Specific Embodiments of the Invention

1. A method for treating cancer in an individual comprising administering to the individual a combination therapy which comprises a PD-1 antagonist and a TLR9 agonist, wherein the TLR9 agonist is a CpG-C type oligonucleotide.

2. A method for treating cancer in an individual comprising administering to the individual a combination therapy which comprises a PD-1 antagonist, an anti-IL-10 antibody or antigen binding fragment thereof and a TLR9 agonist, wherein the TLR9 agonist is a CpG-C type oligonucleotide.

3. The method of embodiment 1 or 2, wherein the PD-1 antagonist is a monoclonal antibody, or an antigen binding fragment thereof.

4. A medicament comprising a PD-1 antagonist for use in combination with a TLR9 agonist for treating cancer in an individual, wherein the PD-1 antagonist is a monoclonal antibody, or an antigen binding fragment thereof and the TLR9 agonist is a CpG-C type oligonucleotide, and preferably, the PD-1 antagonist is administered before the TLR9 agonist.

5. A medicament comprising a PD-1 antagonist for use in combination with a TLR9 agonist and an anti-IL-10 antibody or antigen binding fragment thereof for treating cancer in an individual, wherein the PD-1 antagonist is a monoclonal antibody, or an antigen binding fragment thereof and the TLR9 agonist is a CpG-C type oligonucleotide.

6. A medicament comprising a TLR9 agonist for use in combination with a PD-1 antagonist for treating cancer in an individual, wherein the TLR9 agonist is a CpG-C type oligonucleotide.

7. Use of a PD-1 antagonist in the manufacture of medicament for treating cancer in an individual when administered in combination with a TLR9 agonist, wherein the TLR9 agonist is a CpG-C type oligonucleotide.

8. Use of a PD-1 antagonist in the manufacture of medicament for treating cancer in an individual when administered in combination with a TLR9 agonist and an anti-IL-10 antibody or antigen binding fragment thereof, wherein the TLR9 agonist is a CpG-C type oligonucleotide.

9. Use of a TLR9 agonist in the manufacture of a medicament for treating cancer in an individual when administered in combination with a PD-1 antagonist, wherein the TLR9 agonist is a CpG-C type oligonucleotide.

10. Use of a PD-1 antagonist and a TLR9 agonist in the manufacture of medicaments for treating cancer in an individual, wherein the TLR9 agonist is a CpG-C type oligonucleotide.

11. A kit which comprises a first container, a second container and a package insert, wherein the first container comprises at least one dose of a medicament comprising an anti-PD-1 antagonist, the second container comprises at least one dose of a medicament comprising a TLR9 agonist, and the package insert comprises instructions for treating an individual for cancer using the medicaments, wherein the TLR9 agonist is a CpG-C type oligonucleotide.

12. The kit of embodiment 11, wherein the instructions state that the medicaments are intended for use in treating an individual having a cancer that tests positive for PD-L1 expression by an immunohistochemical (IHC) assay.

13. The method, medicament, use or kit of any of embodiments 1 to 12, wherein the individual is a human and the PD-1 antagonist is a monoclonal antibody, or an antigen binding fragment thereof, which specifically binds to human PD-L1 and blocks the binding of human PD-L1 to human PD-1.

14. The method, medicament, use or kit of any one of embodiments 1-12, wherein the PD-1 antagonist is MPDL3280A, BMS-936559, MEDI4736, MSB0010718C or a monoclonal antibody which comprises the heavy chain and light chain variable regions of SEQ ID NO:24 and SEQ ID NO:21, respectively, of WO2013/019906.

15. The method, medicament, use or kit of any of embodiments 1 to 12, wherein the individual is a human, and the PD-1 antagonist is a monoclonal antibody, or an antigen binding fragment thereof, which specifically binds to human PD-1 and blocks the binding of human PD-L1 to human PD-1.

16. The method, medicament, use or kit of embodiment 15, wherein the PD-1 antagonist also blocks binding of human PD-L2 to human PD-1.

17. The method, medicament, use or kit of embodiment 15, wherein the monoclonal antibody, or antigen binding fragment thereof, comprises: (a) light chain CDRs of SEQ ID NOs: 1, 2 and 3 and heavy chain CDRs of SEQ ID NOs: 4, 5 and 6; or (b) light chain CDRs of SEQ ID NOs: 7, 8 and 9 and heavy chain CDRs of SEQ ID NOs: 10, 11 and 12.

18. The method, medicament, use or kit of embodiment 15, wherein the monoclonal antibody, or antigen binding fragment thereof, comprises light chain CDRs of SEQ ID NOs: 7, 8 and 9 and heavy chain CDRs of SEQ ID NOs: 10, 11 and 12.

19. The method, medicament, use or kit of embodiment 15, wherein the PD-1 antagonist is an anti-PD-1 monoclonal antibody which comprises a heavy chain and a light chain, and wherein the heavy chain comprises SEQ ID NO:21 and the light chain comprises SEQ ID NO:22.

20. The method, medicament, use or kit of embodiment 15, wherein the PD-1 antagonist is an anti-PD-1 monoclonal antibody which comprises a heavy chain and a light chain, and wherein the heavy chain comprises SEQ ID NO:23 and the light chain comprises SEQ ID NO:24.

21. The method, medicament, use or kit of any one of embodiments 1-20, wherein the anti-IL-10 antibody or antigen-binding fragment thereof comprises the heavy chain and light chain variable regions of SEQ ID NO:32 and SEQ ID NO:33.

22. The method, medicament, use or kit of any one of embodiments 1-20, wherein the anti-IL-10 antibody, or antigen binding fragment thereof, comprises: (a) light chain CDRs of SEQ ID NOs: 26, 27 and 28 and heavy chain CDRs of SEQ ID NOs: 29, 30 and 31.

23. The method, medicament, use or kit of any one of embodiments 1-20, wherein the anti-IL-10 antibody is an anti-IL-10 monoclonal antibody which comprises a heavy chain and a light chain, and wherein the heavy chain comprises SEQ ID NO:34 and the light chain comprises SEQ ID NO:35.

24. The method, medicament, use or kit of any one of embodiments 1-20, wherein the anti-IL-10 antibody is anti-IL-10 hum 12G8, or an anti-IL-10 hum 12G8 variant.

25. The method, medicament, use or kit of any one of embodiments 1-24, wherein the CpG-C type oligonucleotide consists of:
(a) 5'-$N_x$(TCG(N))$_y$$N_w$($X_1X_2$CG$X_2$'$X_1$'(CG)$_p$)$_z$$N_v$ (SEQ ID NO:38) wherein N are nucleosides, x=0, 1, 2 or 3, y=1, 2, 3 or 4, w=0, 1 or 2, p=0 or 1, q=0, 1 or 2, v=0 to 89 and z=1 to 20, $X_1$ and $X_1$' are self-complementary nucleosides, and $X_2$ and $X_2$' are self-complementary nucleosides; and
(b) a palindromic sequence at least 8 bases in length wherein the palindromic sequence comprises the first ($X_1X_2$CG$X_2$'$X_1$') of the ($X_1X_2$CG$X_2$'$X_1$'(CG)$_p$)$_z$ sequences, wherein the oligonucleotide is from 12 to 100 bases in length.

26. The method, medicament, use or kit of embodiment 25, wherein x=0, y=1, w=0, p=0 or 1, q=0, 1 or 2, v=0 to 20 and z=1, 2, 3 or 4.

27. The method, medicament, use or kit of any one of claims 1-24, wherein the CpG-C type oligonucleotide consist of TCGN$_q$($X_1X_2$CG$X_2$'$X_1$'CG)$_z$$N_v$ (SEQ ID NO:39), wherein N are nucleosides, q=0, 1, 2, 3, 4, or 5, v=0 to 20, z=1 to 4, $X_1$ and $X_1$' are self-complementary nucleosides, $X_2$ and $X_2$' are self-complementary nucleosides, and wherein the oligonucleotide is at least 12 bases in length.

28. The method, medicament, use or kit of any one of embodiments 1-24, wherein the CpG-C type oligonucleotide consist of 5'-TCGN$_q$TTCGAACGTTCGAACGTTN$_s$-3' (SEQ ID NO:40), wherein N are nucleosides, q=0, 1, 2, 3, 4, or 5, s=0 to 20, and wherein the oligonucleotide is at least 12 bases in length.

29. The method, medicament, use or kit of any one of embodiments 1-24, wherein the CpG-C type oligonucleotide is selected from the group consisting of:

```
5'-TCGTCGAACGTTCGAGATGAT-3';        (SEQ ID NO: 41)

5'-TCGTTCGAACGTTCGAACGTTCGAA-3';    (SEQ ID NO: 42)

5'-TCGAACGTTCGAACGTTCGAACGTT-3';    (SEQ ID NO: 43)

5'-TCGAACGTTCGAACGTTCGAATTTT-3';    (SEQ ID NO: 44)

5'-TCGAACGTTCGAACGTTCGAACGTTCGAAT-3'; (SEQ ID NO: 45)

5'-TCGTAACGTTCGAACGTTCGAACGTTA-3';  (SEQ ID NO: 46)

5'-TCGTAACGTTCGAACGTTCGAACGTT-3';   (SEQ ID NO: 47)

5'-TCGTAACGTTCGAACGTTCGAACGT-3';    (SEQ ID NO: 48)

5'-TCGTAACGTTCGAACGTTCGAACG-3';     (SEQ ID NO: 49)

5'-TCGTAACGTTCGAACGTTCGAAC-3';      (SEQ ID NO: 50)
and

5'-TCGTAACGTTCGAACGTTCGAA-3'.       (SEQ ID NO: 51)
```

30. The method, medicament, use or kit of any one of embodiments 1-24, wherein the CpG-C type oligonucleotide has the sequence consisting of 5'-TCGAACGTTCGAACGTTCGAACGTTCGAAT-3' (SEQ ID NO:45).

31. The method, medicament, use or kit of any of embodiments 1-30, wherein the cancer is a solid tumor.

32. The method, medicament, use or kit of any of embodiments 1-30, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer.

33. The method, medicament, use or kit of any of embodiments 1-30, wherein the cancer is NSCLC, RCC, endometrial cancer, urothelial cancer, squamous cell carcinoma of head and neck or melanoma.

34. The method, medicament, use or kit of any of embodiments 1-30, wherein the individual has not been previously treated for NSCLC, RCC, endometrial cancer, urothelial cancer, squamous cell carcinoma of head and neck or melanoma.

35. The method, medicament, use or kit of any of embodiments 1-30, wherein the cancer is advanced or metastatic melanoma.

36. The method, medicament, use or kit of any of embodiments 1-30, wherein the cancer is acute lymphoblastic leukemia (ALL), acute myeloid leukemia (AML), chronic lymphocytic leukemia (CLL), chronic myeloid leukemia (CIVIL), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), cutaneous T-cell lymphoma, or small lymphocytic lymphoma (SLL).

37. The method or medicament of any one of claims 1-30, wherein the cancer is selected from the group consisting of renal cell carcinoma, non-small cell lung cancer, bladder cancer and colorectal cancer.

38. The method, medicament, use or kit of any of embodiments 1-37, wherein the cancer tests positive for human PD-L1.

39. The method, medicament, use or kit of embodiment 38, wherein the human PD-L1 expression is elevated.

40. The method, medicament, use or kit of embodiment 38, wherein the PD-1 antagonist is pembrolizumab, a pembrolizumab variant or nivolumab.

41. The method, medicament, use or kit of embodiment 40, wherein pembrolizumab is formulated as a liquid medicament which comprises 25 mg/ml pembrolizumab, 7% (w/v) sucrose, 0.02% (w/v) polysorbate 80 in 10 mM histidine buffer pH 5.5.

42. A medicament comprising pembrolizumab for use in combination with a CpG-C type oligonucleotide of SEQ ID NO: 45 for treating cancer in a human individual by a method comprising first administering to the individual pembrolizumab, followed by intratumorally administering the oligonucleotide of SEQ ID NO: 45 from one to four weeks later, preferably one, two or three weeks later.

43. A method for treating a human individual diagnosed with cancer, comprising administering to the individual a combination therapy which comprises pembrolizumab and a CpG-C type oligonucleotide of SEQ ID NO: 45, and wherein pembrolizumab is administered at 200 mg Q3W and the oligonucleotide of SEQ ID NO: 45 is intratumorally administered at a dose of from 1 to 16 mg once a week, preferably at a dose of 1.0, 2.0, 4.0, 8.0 or 16.0 mg once a week.

44. A medicament comprising pembrolizumab for use in combination with a CpG-C type oligonucleotide of SEQ ID NO: 45 for treating cancer in a human individual by a method comprising administering to the individual 200 mg of pembrolizumab Q3W starting on Day 1 and intratumorally administering the oligonucleotide of SEQ ID NO: 45 at a dose of from 1 to 16 mg starting on Day 22, and then once a week for four weeks, followed by a dose of from 1 to 16 mg once every three weeks, preferably wherein the oligonucleotide of SEQ ID NO: 45 is intratumorally administered at a dose of 1.0, 2.0, 4.0, 8.0 or 16.0 mg.

45. A medicament comprising pembrolizumab for use in combination with a CpG-C type oligonucleotide of SEQ ID NO: 45 for treating cancer in a human individual by a method comprising administering to the individual 200 mg of pembrolizumab Q3W starting on Day 1 and intratumorally administering the oligonucleotide of SEQ ID NO: 45 at a dose of from 1 to 16 mg starting on Day 1 once a week for four weeks, followed by a dose of from 1 to 16 mg once every three weeks, preferably wherein the oligonucleotide of SEQ ID NO: 45 is intratumorally administered at a dose of 1.0, 2.0, 4.0, 8.0 or 16.0 mg.

46. A medicament comprising pembrolizumab for use in combination with a CpG-C type oligonucleotide of SEQ ID NO: 45 for treating cancer in a human individual by a method comprising administering to the individual 200 mg of pembrolizumab Q3W starting on Day 1 and intratumorally administering the oligonucleotide of SEQ ID NO: 45 at a dose of from 1 to 16 mg starting on Day 22 once a week for four weeks, followed by a dose of from 1 to 16 mg once every three weeks preferably wherein the oligonucleotide of SEQ ID NO: 45 is intratumorally administered at a dose of 1.0, 2.0, 4.0, 8.0 or 16.0 mg.

47. The method or medicament of embodiment 42-44, or 46, wherein the individual has not been previously treated with anti-PD-1 or anti-PD-L1 therapy.

48. The method or medicament of embodiment 43 or 45, wherein the individual is confirmed progressive while receiving prior anti-PD-1 therapy.

49. The method or medicament of any of embodiments 42-48, wherein pembrolizumab is administered by IV infusion for 25 to 40 minutes or about 30 minutes.

50. The method or medicament of any of embodiments 42-49, wherein a tissue section of the cancer is removed from the individual prior to administration of the combination therapy tested positive for PD-L1 expression.

51. The method or medicament of embodiment 50, wherein at least 50% of the tumor cells in the tissue section tested positive for PD-L1 expression by an immunohistochemical (IHC) assay.

52. The method or medicament of embodiment 51, wherein the IHC assay employed the antibody 22C3 to detect PD-L1 expression.

53. The method or medicament of any one of embodiments 1-52, wherein the CpG-C type oligonucleotide is a sodium salt with the sequence of 5'-TCGAACGTTCGAACGTTC-GAACGTTCGAAT-3' (SEQ ID NO: 45), and the oligonucleotide is an oligodeoxynucleotide with a phosphorothioate backbone.

54 The method, medicament, use or kit of any one of embodiments 1-53, wherein the CpG-C type oligonucleotide has a sequence that consists of 5'-TCGTTCGAACGTTC-GAACGTTCGAA-3' (SEQ ID NO:42).

55. The method, medicament, use or kit of any one of embodiments 1-53, wherein the CpG-C type oligonucleotide is a sodium salt of 5'-TCGTTCGAACGTTCGAACGTTC-GAA-3' (SEQ ID NO:42).

56. The method, medicament, use or kit of any of embodiments 42-55, wherein the cancer is advanced or metastatic melanoma.

57. The method of embodiment 1, wherein the PD-1 antagonist is pembrolizumab and the CpG-C type oligonucleotide has a sequence consisting of 5'-TCGAACGTTCGAACGT-TCGAACGTTCGAAT-3'(SEQ ID NO:45).

58. The method of embodiment 1, wherein the PD-1 antagonist is pembrolizumab and the CpG-C type oligonucleotide has a sequence consisting of 5'-TCGAACGTTCGAACGT-TCGAACGTTCGAAT-3'(SEQ ID NO:45), and the oligonucleotide is an oligodeoxynucleotide with a phosphorothioate backbone.

59. The method of embodiment 57 or 58 wherein the cancer is advanced or metastatic melanoma.

60. The method of embodiment 1, wherein the PD-1 antagonist is pembrolizumab and the CpG-C type oligonucleotide has a sequence consisting of 5'-TCGTTCGAACGTTC-GAACGTTCGAA-3' (SEQ ID NO:42).

61. The method of embodiment 1, wherein the PD-1 antagonist is a monoclonal antibody, or antigen binding fragment thereof, which comprises light chain CDRs of SEQ ID NOs: 7, 8 and 9 and heavy chain CDRs of SEQ ID NOs: 10, 11 and 12, and the CpG-C type oligonucleotide consists of:
(a) 5'-$N_x(TCG(N_q))_yN_w(X_1X_2CGX_2'X_1'(CG)_p)_zN_v$ (SEQ ID NO:38) wherein N are nucleosides, x=0, 1, 2 or 3, y=1, 2, 3 or 4, w=0, 1 or 2, p=0 or 1, q=0, 1 or 2, v=0 to 89 and z=1 to 20, $X_1$ and $X_1'$ are self-complementary nucleosides, and $X_2$ and $X_2'$ are self-complementary nucleosides; and
(b) a palindromic sequence at least 8 bases in length wherein the palindromic sequence comprises the first $(X_1X_2CGX_2'X_1')$ (SEQ ID NO:55) of the $(X_1X_2CGX_2'X_1'(CG)_p)_z$ (SEQ ID NO:56) sequences, wherein the oligonucleotide is from 12 to 100 bases in length.

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fuse with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Example 1: Immunomodulation of Human Cells by C59-08

C59-08 is a sodium salt of oligodeoxynucleotide 5'-TC-GAACGTTCGAACGTTCGAACGTTCGAAT-3' (SEQ ID NO: 45) with a phosphorothioate backbone.

Human peripheral blood mononuclear cells (PBMCs) were isolated from buffy coats from two donors with Ficoll-Paque™ PLUS (GE Healthcare Bio-Sciences, Pittsburgh, Pa.) using standard separation methods. Isolated PBMCs were washed twice in phosphate buffered saline (PBS) containing 2% fetal bovine serum (FBS), and 2 mM ethylenediaminetetraacetic acid (EDTA). The cells were resuspended and cultured in 96-well U-bottom plates at $1 \times 10^6$ cells per well in RPMI 1640 containing 10% FBS, 2 mM L-glutamine, 100 U/mL penicillin and 100 μg/mL streptomycin. The cells were cultured in the presence of C59-08 at doses ranging from 0.016 μM to 5 μM or 7 μM control ODN 1040 in a humidified incubator at 37° C., 5% $CO_2$ in final volume of 0.2 mL for 48 hours. Supernatants were harvested and assayed for IFNα2a and IL-10 using Meso Scale Discovery human IFNα2a and human IL-10 tissue culture kits (Rockville, Md.).

The results are shown in FIG. 12. C59-08 induces both IFNα2a and IL-10 production in human PBMCs with an optimal concentration of 0.2 μM.

Example 2: Immunomodulation of Human Tumor Specimens by C59-08

Human Tumor Histocultures

Human tumor specimens from patients were obtained from commercial sources (Bio-Options, Folio, Coversant Bio, and Boston BioSource) and University of Rochester. Fresh tumor tissues were collected within 1 hour following surgery and placed into AQIX transportation media (AQIX, UK). Tissues were transported overnight at 4° C. to Merck Research Laboratories, Palo Alto, Calif.

The tumors were embedded in UltraPure™ low melting point agarose (Invitrogen, Carlsbad, Calif.) and were cut 400 μm with McIlwain™ Tissue Chopper (Stoelting Co., Wood Dale, Ill.). The tumor slices were first set on the Millicell-CM cell culture insert (Millipore, Billerica, Calif.) and cultured at the interface between air and medium of 1 ml DMEM supplemented with 4.5 g/L glucose, L-glutamine, sodium pyruvate (Mediatech, Inc., Manassas, Va.), 10% FBS (SAFC Biosciences, Lenexa, Kans.), 100 U/ml penicillin, and 100 ug/ml streptomycin in humidified incubator at 37° C., 5% $CO_2$.

The tumor slices were cultured in the presence of 0.1, 0.5, and 1 μM C59-08 or 1 μM control ODN 1040 for 24 hours. The tumor samples were snap frozen in dry ice and stored at 37° C. prior to processing.

RNA Isolation and Real-Time Quantitative PCR

Total RNA was isolated by homogenization into RNA STAT-60 (Tel-Test, Friendswood, Tex.) using a polytron homogenizer. The total RNA was extracted according to the manufacturer's protocol. After precipitation with isopropanol, total RNA was re-extracted with phenol:chloroform:isoamyl alcohol (25:24:1) (Sigma-Aldrich, St. Louis, Mo.) using phase-lock light tubes.

DNase-treated total RNA was reverse-transcribed using QuantiTect Reverse Transcription (Qiagen, Valencia, Calif.) according to manufacturer's protocol. Primers were obtained commercially from Life Technologies (Foster City, Calif.). Real-time quantitative PCR on 10 ng of cDNA from each sample was performed using unlabeled primers at 900 nM each with 250 nM of FAM-labeled probe in a TAQ-MAN™ RTqPCR reaction on the Fluidigm Biomark sequence detection system (Fluidigm, Foster City, Calif.). Levels of ubiquitin were measured in a separate reaction and were used to normalize the data by the Δ-Δ Ct method. Using the mean cycle threshold (Ct) value for ubiquitin and the gene of interest for each sample, the following equation was used to obtain the normalized values: $1.8^{(Ct\ ubiquitin - Ct\ gene\ of\ interest)} \times 10^4$.

Treatment Results

Figure 13A:
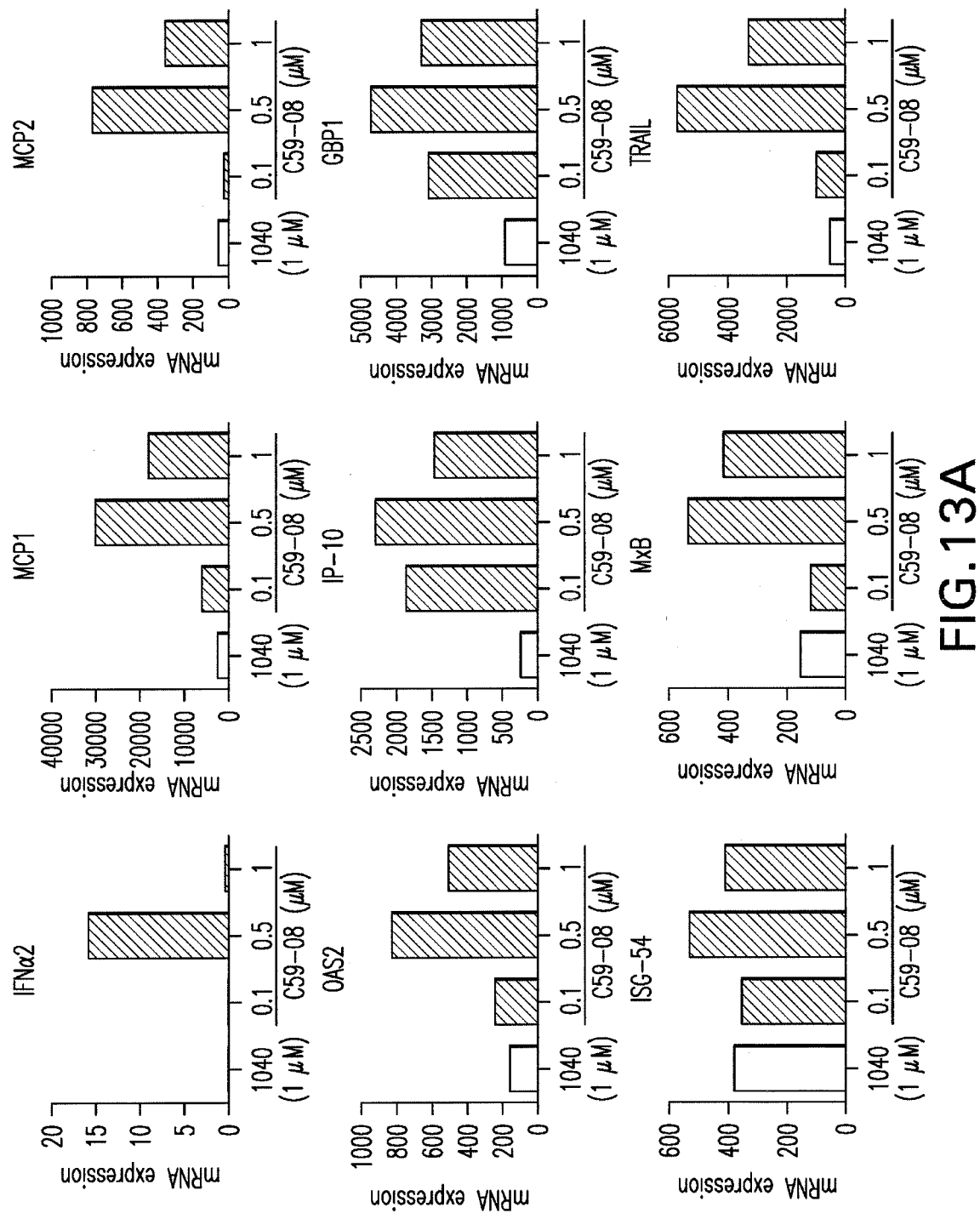
FIG. 13 shows induction of mRNA expression of IFNα-inducible genes (Panel A), cytokines (Panel B), and immune activation markers (Panel C) in a human renal cell carcinoma histoculture following treatment with C59-08 for 24 hours.
Figure 13B:
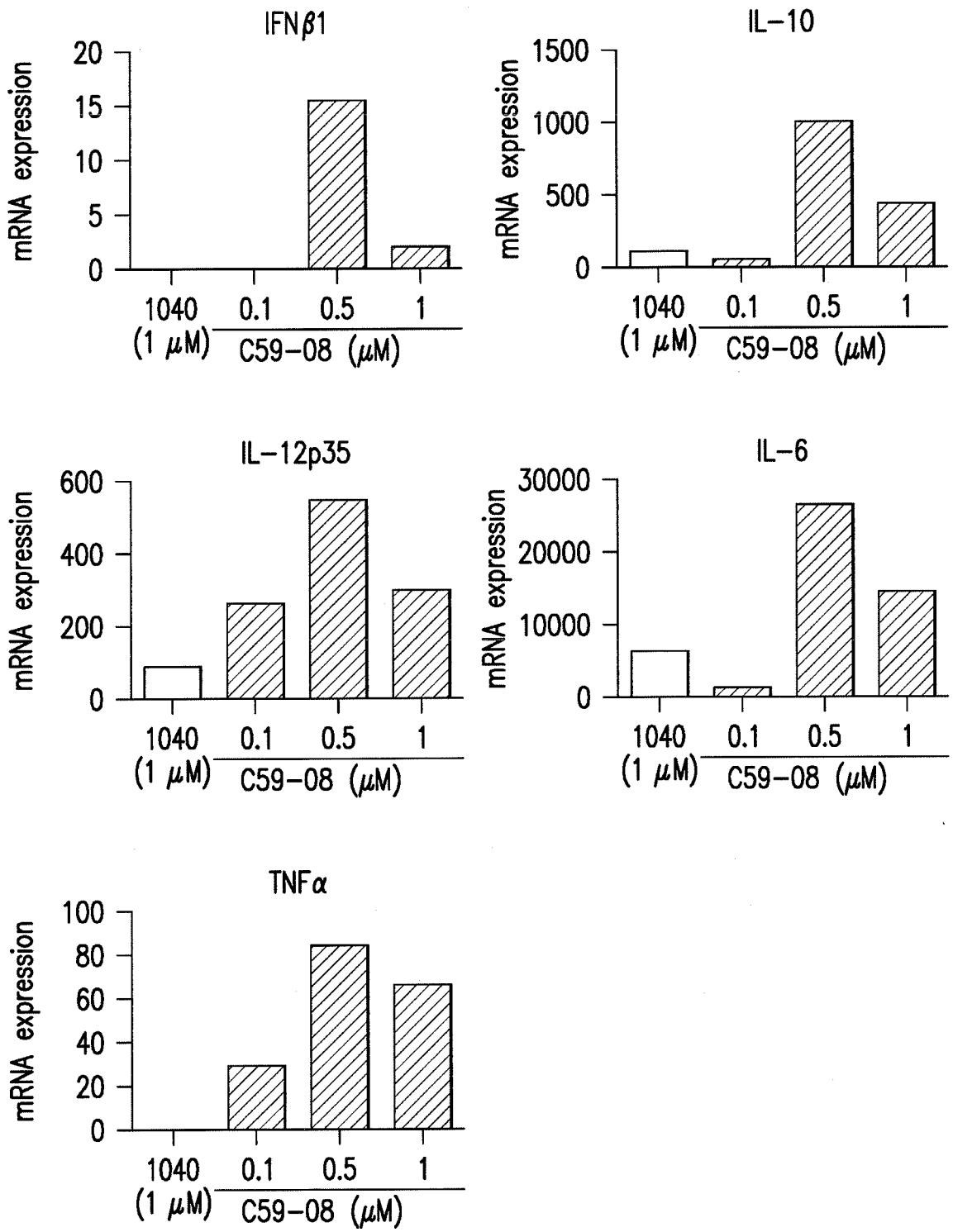
Figure 13C:
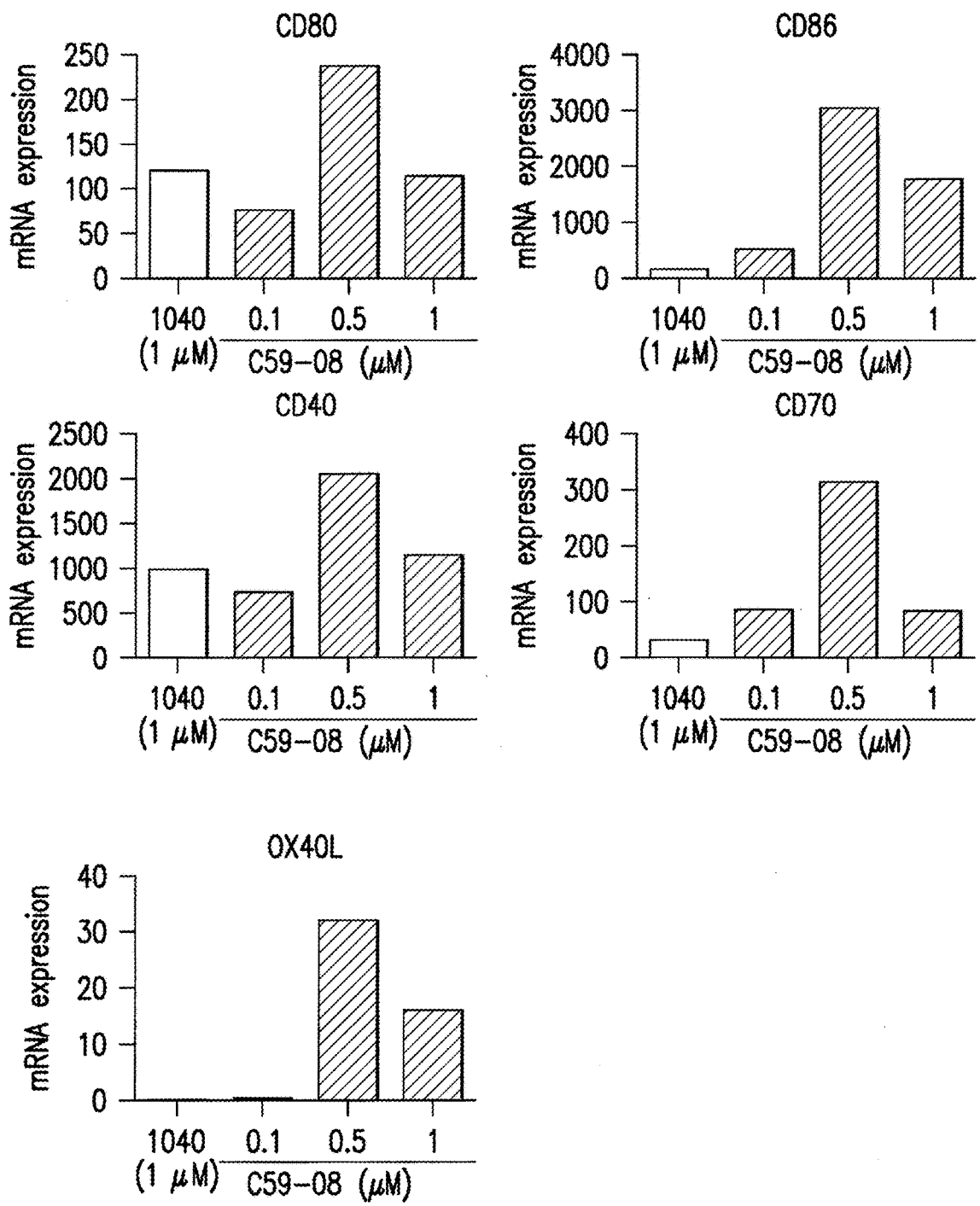

Ex vivo treatment of human tumors with C59-08 induced IFNα-inducible genes (IFNα2, MCP1, MCP2, OAS2, IP-10, GBP1, ISG-54, MxB, and TRAIL), cytokines (IFNβ, IL-10, IL-12, IL-6, and TNFα), and immune activation markers (CD80, CD86, CD40, CD70 and OX40L) in renal cell carcinoma (RC) (n=5), non-small cell lung cancer (NSCLC) (n=3), and bladder (n=1) and colorectal (n=1) cancer histocultures. Data with a specimen from a RCC donor are shown in FIG. 13: (A) IFNα-inducible genes; (B) cytokines; and (C) immune activation markers.

Example 3: Anti-Tumor Activity of Combination of Anti-IL-10 and Intratumoral C59-08 in Animal Model TC40.11D8 is a mouse IgG1/kappa monoclonal antibody targeted against mouse IL-10. The mouse IgG1 isotype control is a mouse monoclonal antibody specific for adenoviral hexon 25. Both antibodies were obtained from internal sources as frozen (−80° C.) stocks.

Formulations of Antibodies

The formulation buffer is specific for each antibody to stabilize proteins and prevent precipitation. The formulations for both TC40.11D8 and the mouse IgG1 isotype control were 75 mM sodium chloride, 10 mM sodium phosphate, 3% sucrose, pH7.3.

Oligodeoxynucleotides

Cytidine phospho-guanosine (CpG)-based phosphorothioate oligodeoxynucleotide (ODN) CpG 1826 5'-tccatgacgttcctgacgtt-3' (SEQ ID NO: 53) (InvivoGen, San Diego, Calif.) is a mouse TLR9 specific agonist. CpG 1826 has a CpG-B type sequence. CpG-based phosphorothioate ODN C59-08 (Dynavax, Berkeley, Calif.) is an agonist that activates both human and mouse TLR9. C59-08 has a CpG-C type sequence: 5'-TCGAACGTTCGAACGTTCGAACGTTCGAAT-3' (SEQ ID NO:45), wherein the 5' and 3' is an OH group.

Control ODN (Dynavax, Berkeley, Calif.) has a non-CpG sequence with a phosphorothioate backbone 5'-TGA CTG TGA ACC TTA GAG ATG A-3' (SEQ ID NO:54).

Formulations of Oligodeoxynucleotides

CpG 1826 was reconstituted in 0.9% sodium chloride at a concentration of 2 mg/mL, aliquoted, and stored at −20° C. C59-08 was reconstituted in phosphate buffered saline (PBS) at a concentration of 4.53 mg/mL, aliquoted, and stored at −20° C. Control ODN was reconstituted in PBS at a concentration of 4.47 mg/mL, aliquoted, and stored at −20° C.

Animals

Approximately seven to eight week old female C57BL/6J mice were obtained from Jackson Laboratory (Sacramento, Calif.). Conventional animal chow and water were provided ad libitum. Animals were housed for one week prior to the start of the study. The average weight of the animals at the start of the study (i.e. tumor implantation) was 19 grams.

Procedures involving the care and use of animals in the study were reviewed and approved by the Institutional Animal Care and Use Committee at Merck Research Laboratories. During the study, the care and use of animals were conducted in accordance with the principles outlined in the guidance of the Association for Assessment and Accreditation of Laboratory Animal Care (AAALAC), the Animal Welfare Act, the American Veterinary Medical Association (AVMA) Euthanasia Panel on Euthanasia, and the Institute for Laboratory Animal Research (ILAR) Guide to the Care and Use of Laboratory Animals.

Tumor Cell Line Preparation and Implantation

The TC-1 cell line, provided by Johns Hopkins University (Baltimore, Md.) is derived from mouse primary lung epithelial cells that were cotransformed with human papilloma virus (HPV-16) E6 and E7 and c-Ha.ras oncogene (Lin et al., Cancer Res., 56:21-6, 1996). TC-1 cells are syngeneic to the C57BL6/J mouse strain.

The TC-1 cells were cultured in DMEM supplemented with 10% fetal bovine serum and 0.4 mg/mL Geneticin. Sub-confluent TC-1 cells were injected subcutaneously (SC) in 0.1 mL of serum-free DMEM in both lower dorsal flanks ($1 \times 10^5$ in right flank and $0.5 \times 10^5$ in left flank) of each animal. Animals were first shaved with electric clippers in the areas that were used for the implantation.

Tumor Measurements and Body Weights

Tumors were measured the day before the first dose and twice a week thereafter. Tumor length and width were measured using electronic calipers and tumor volume determined using the formula Volume (mm$^3$)=0.5×Length×Width where length is the longer dimension. Animals were weighed the day before the first dose and twice a week thereafter. To prevent bias, any outliers by weight or tumor volume were removed and the remaining mice were grouped into various treatment groups based on the tumor volume in the right flank (referred to as the injected tumor).

Dosing Solution Preparation

Frozen stocks of the antibodies were thawed and transferred to wet ice. To avoid repeated freeze thaw, each vial of stock was thawed once and aliquots made in volumes sufficient for one time use. Polypropylene, low adhesion tubes were used for this purpose. The aliquots were stored at −80° C. Before each dosing, one aliquot was thawed and diluted to nominal concentration in the appropriate diluent.

Before each dosing, aliquots of the ODNs (control ODN, CpG 1826, and C59-08) were thawed and diluted to nominal concentration in 0.9% sodium chloride.

Administration of Antibodies and Oligodeoxynucleotides

Isotype control mIgG1 and anti-IL-10 mIgG1 were administered intraperitoneally (IP) at 10 mg/kg on Days 0, 4, 8, and 12. Control ODN (2.5 mg/kg), CpG 1826 (1 mg/kg), and C59-08 (2.5 mg/kg) were administered intratumorally (IT) only in right tumors on Days 0, 4, 8, and 12.

Statistical Methods

Tumor volumes were compared between treatments at each day of follow-up. Follow-up of individual animals could be terminated early because of excessive tumor burden or other reasons. Depending on the reason and tumor size at the last measurement, the last observed tumor volume was treated as a lower bound on volume at all later days for that animal (right-censored data).

To compare two treatment groups on a given day, a generalization of the nonparametric Mann-Whitney (or Wilcoxon rank sum) test that allows for right-censored data was used: the Peto and Peto version of the Gehan-Breslow test. Two-sided p-values were estimated from 20,000 random reassignments of animals between the two treatments being compared. To control the familywise error rate across all time points for a given pair of treatments, p-values were multiplicity adjusted by applying the maxT procedure of Westfall and Young to the permutation distributions. A p-value of less than 0.05 was used to define statistical significance.

For descriptive purposes, volumes for each day and treatment group were summarized by their median. To allow for censoring, a distribution function for each day and treatment group was estimated by the Kaplan-Meier method, with confidence band using Greenwood's formula on a log scale. The median was estimated as the 50th percentile of the distribution function, with confidence interval obtained by inverting the confidence band. A 68% confidence level was used, to be comparable to the common "mean±SE" format for summarizing data, since the latter is approximately a 68% confidence interval for the mean.

When follow-up of an animal was terminated early, the reason was categorized and the animal's data were handled as follows: (1) tumor burden: right-censor at last measured value; (2) tumor ulceration: right-censor at last measured value, provided this exceeded a threshold (1000 mm$^3$); otherwise omit animal at later times; (3) weight loss/ill (including found dead with evidence of illness): omit animal at later times; and (4) unrelated to treatment (e.g., accident found dead with no evidence of illness, administrative termination): right-censor at last measured value, provided this exceeded a threshold (1000 mm$^3$); otherwise omit animal at later times.

Treatment Results

Figure 10B:
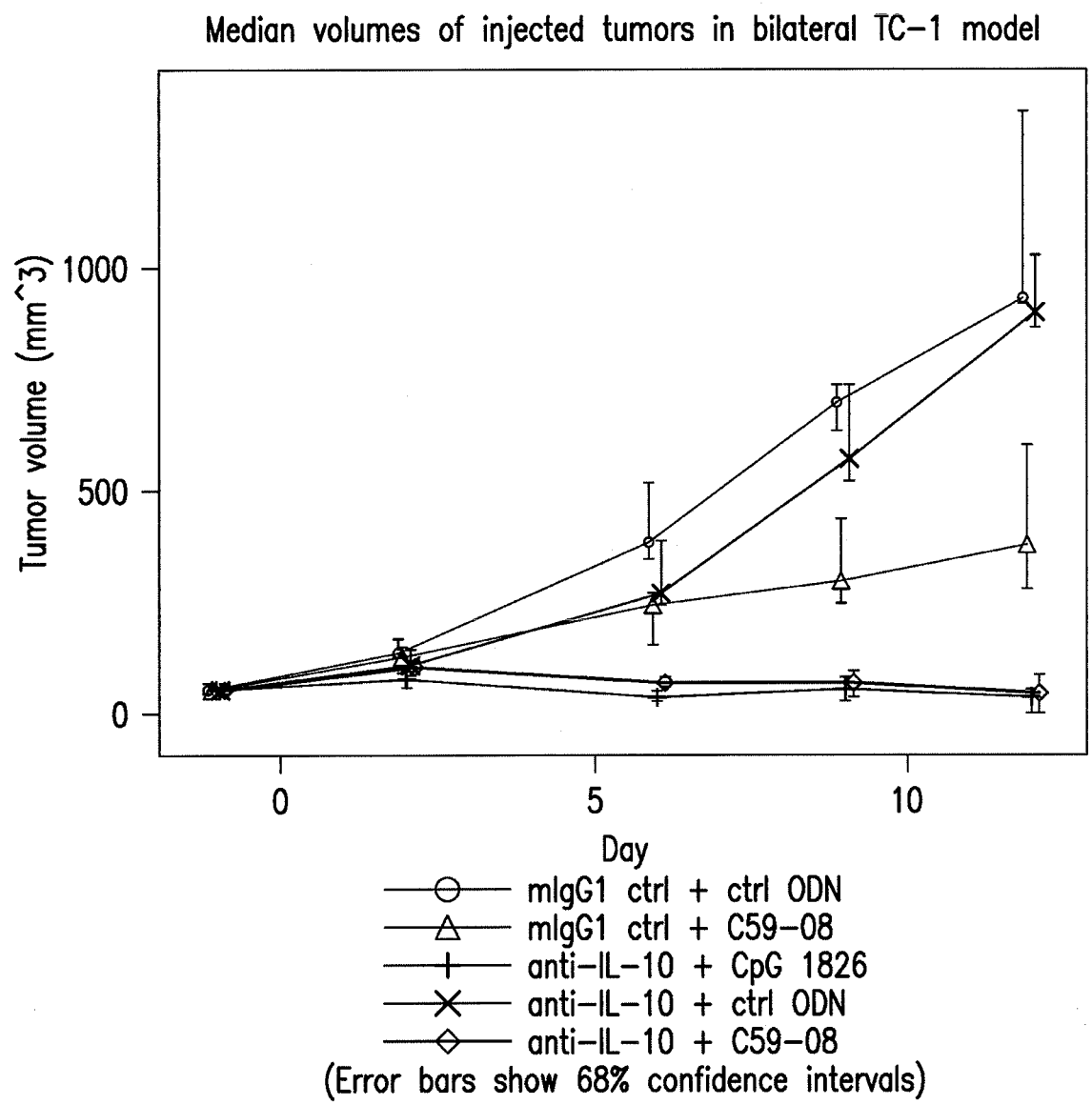
Figure 10C:
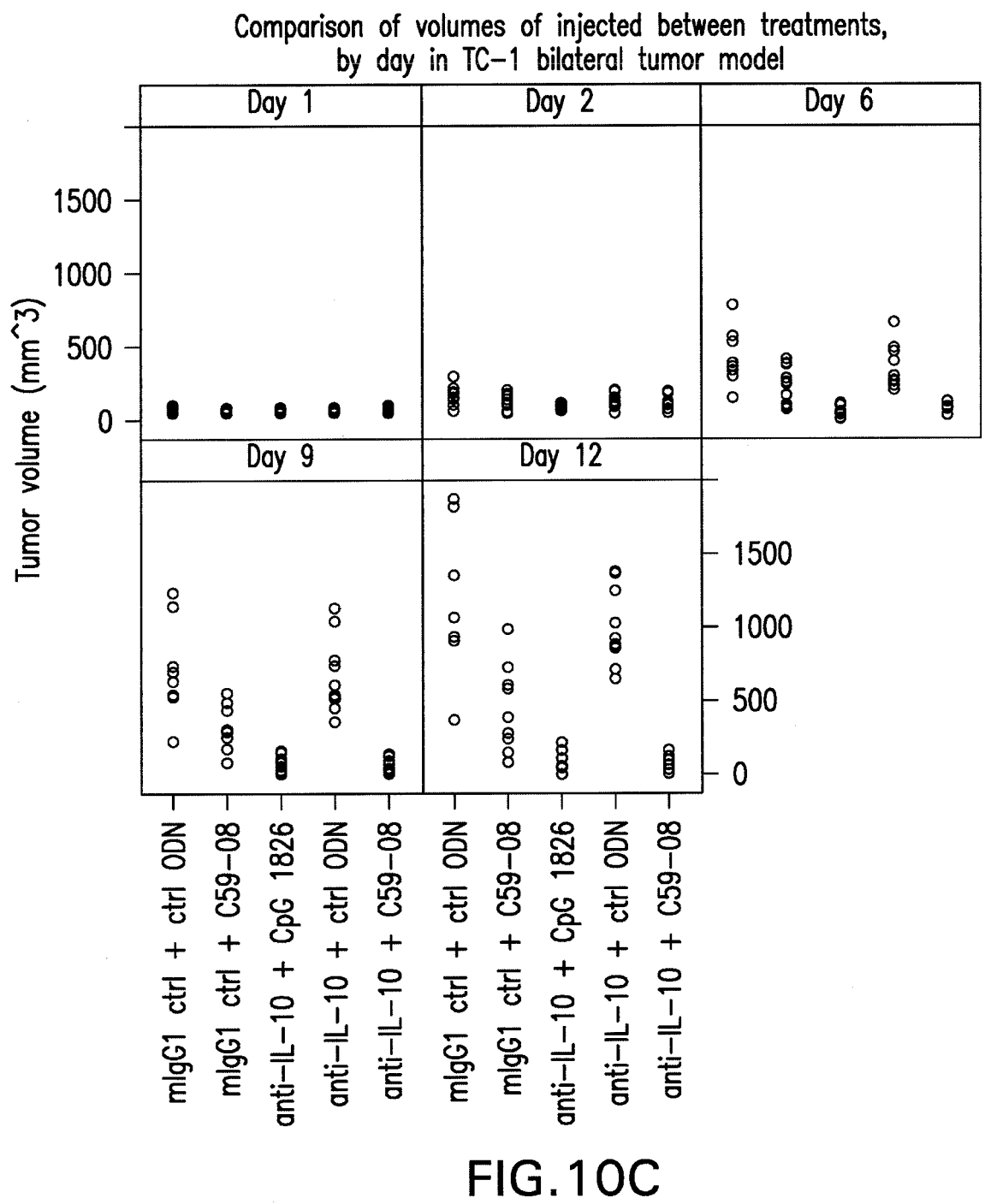
Figure 11A:
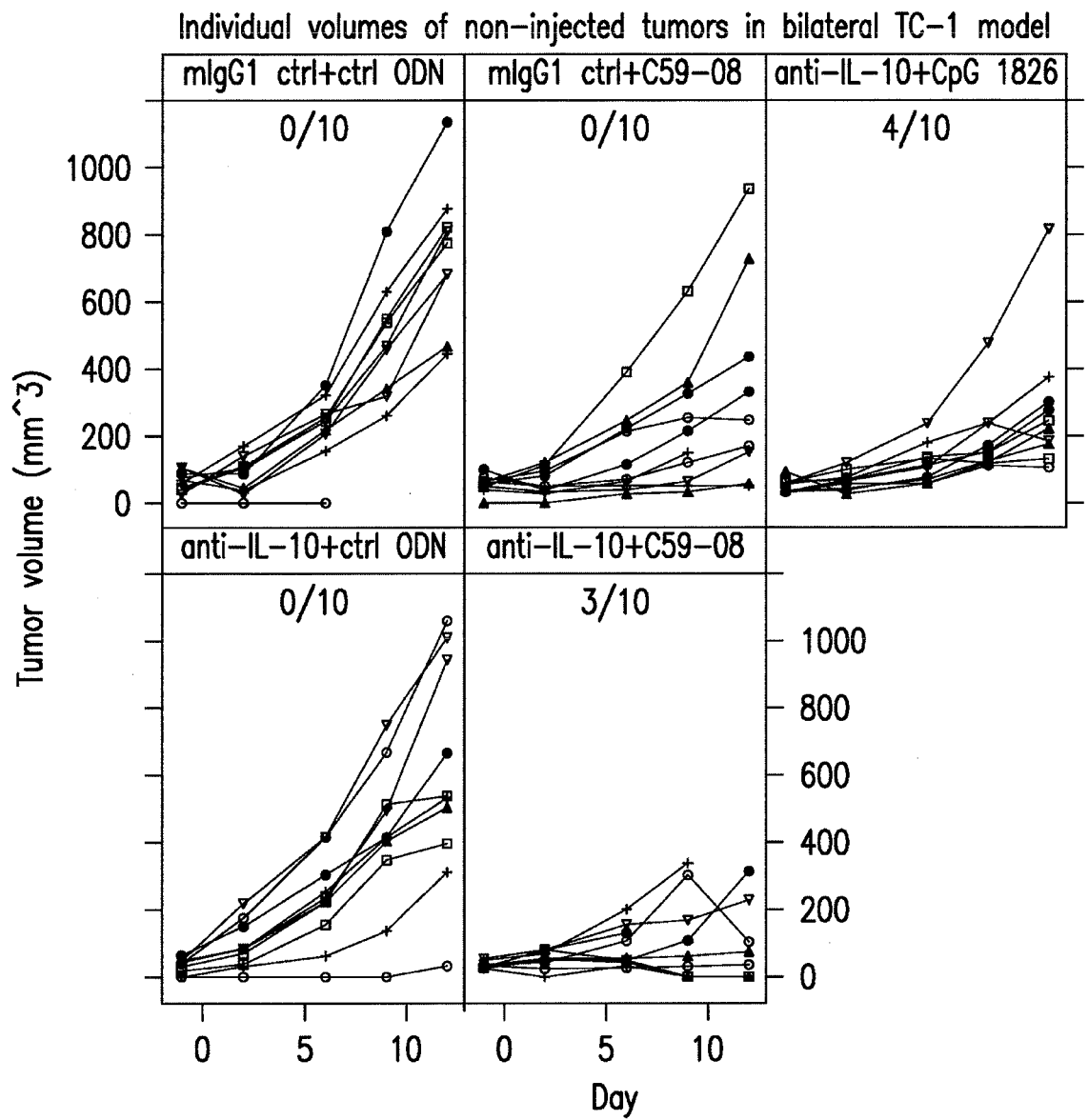
FIG. 11 shows tumor growth of non-injected tumors in mouse TC-1 bilateral tumor model. Panel A shows volume of non-injected tumors for individual animals and number of complete regressions (CRs) per group. Panel B shows median volume of non-injected tumors with error bar indicating 68% confidence interval. Panel C compares volumes of non-injected tumors between treatment groups by day. Panel D shows unadjusted and multiplicity-adjusted P-values for comparison of volumes of non-injected tumors between treatments. Unadjusted p value refers to two-sided p-values based on the Peto & Peto version of the Gehan-Breslow nonparametric test statistic for right-censored data. P-values were estimated from 20,000 random reassignments of animals between the two treatments being compared. Multiplicity adjusted p-values refers to p-values adjusted to control the familywise error rate across all time points for a given pair of treatments. Adjustment was by applying the maxT procedure of Westfall and Young to the permutation distributions.
Figure 11B:
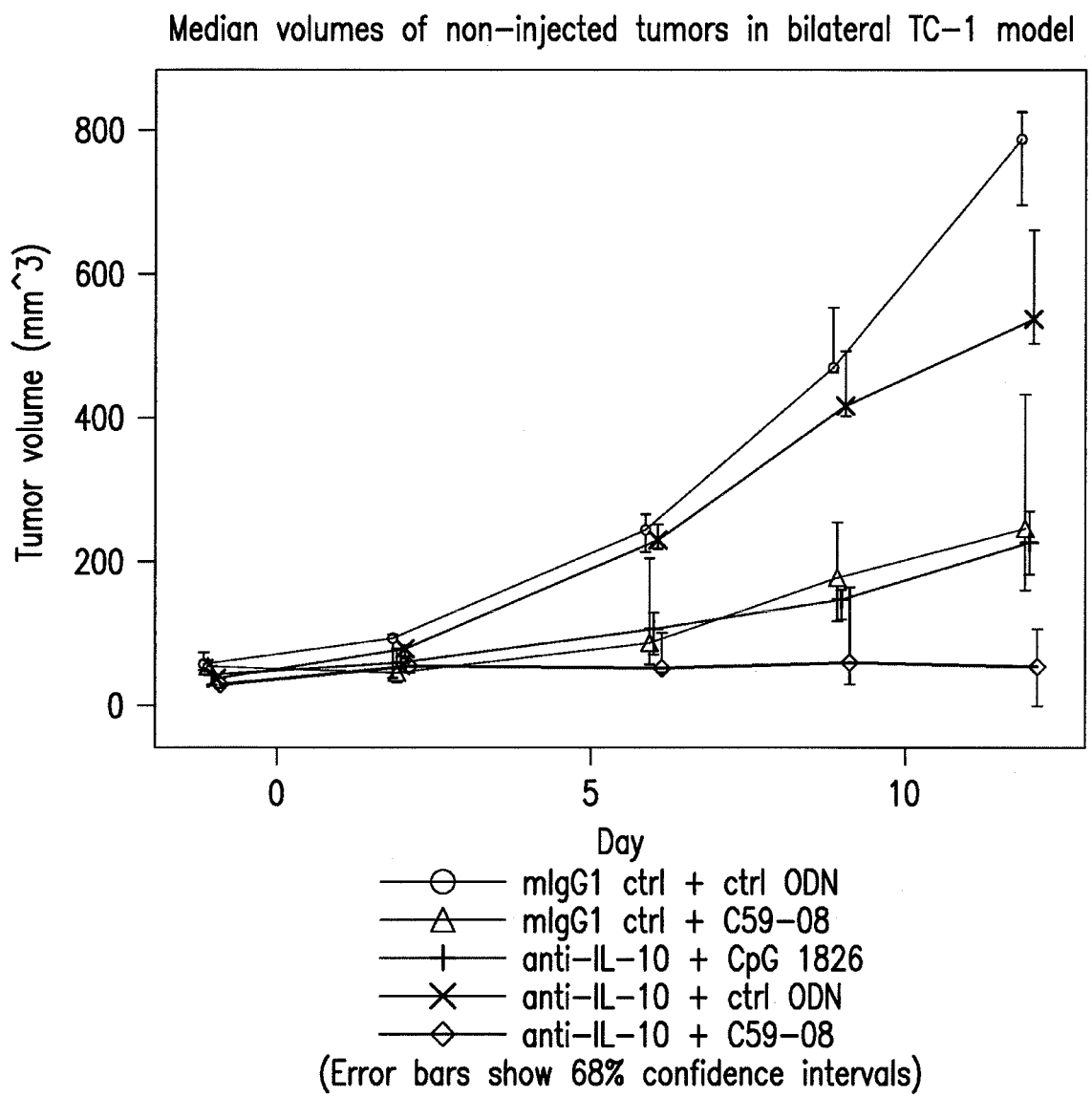
Figure 11C:
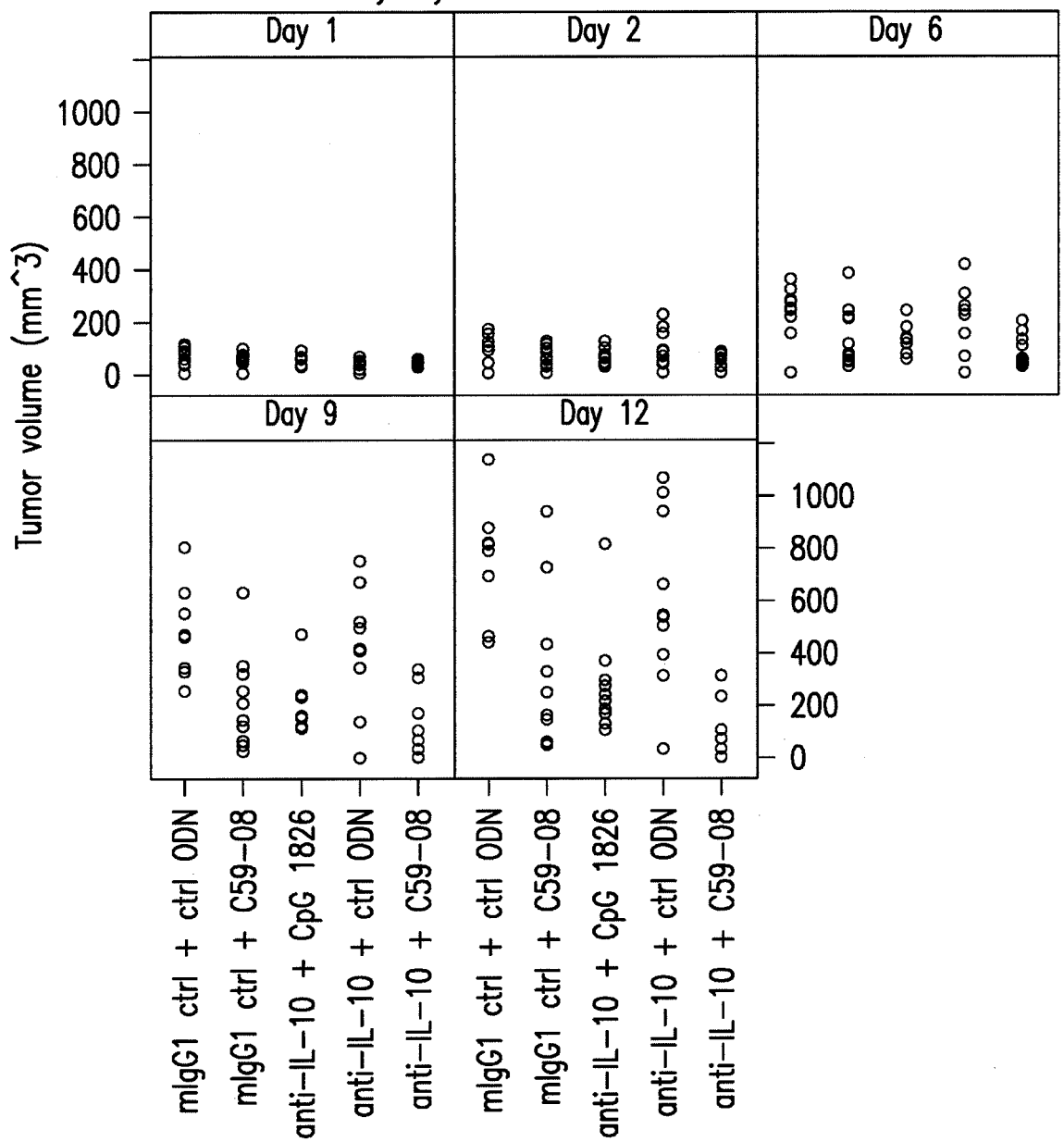

TC-1 tumor-bearing C57BL/6J mice were grouped into 5 treatment groups the day before the first dose when the mean volume of tumors on right flank reached approximately 60 mm$^3$ (39 mm$^3$-87 mm$^3$): (1) mIgG1 isotype control+control ODN; (2) mIgG1 isotype control+C59-08; (3) anti-IL-10+ CpG 1826; (4) anti-IL-10+control ODN; and (5) anti-IL-10+C59-08. The range of volumes of tumors on left was 0 mm$^3$-113 mm$^3$. Complete regression (CR) of a tumor was defined as the absence of a measurable tumor at the time the measurement was conducted, given that a tumor was measurable on the day that animals were grouped. The results are shown in FIGS. 10 and 11. Anti-IL-10 in combination with either intratumoral CpG 1826 (Group 3) or C59-08 (Group 5) resulted in CRs of injected tumors in at least 3 animals (FIG. 10A). However, only anti-IL-10 in combination with C59-08 (Group 5) resulted in CRs (three of ten animals) of non-injected tumors (FIG. 11A). Other treatments including C59-08 monotherapy (Group 2) did not result in CRs of either injected or non-injected tumors. Compared to control treatment, anti-IL-10 monotherapy, and C59-08 monotherapy, administration of anti-IL-10 in combination with C59-08 (IT) resulted in significantly reduced volumes of injected tumors for Days 6, 9, and 12 (p<0.05, multiplicity adjusted across time points) (FIG. 10B-D). Compared to control treatment and anti-IL-10 monotherapy, administration of anti-IL-10 in combination with C59-08 (IT) resulted in significantly reduced volumes of non-injected tumors for Days 6, 9, and 12 (p<0.05, multiplicity adjusted across time points) (FIG. 11B-D).

Example 4: Anti-Tumor Activity of a Combination of Systemic Anti-PD-1 Antibody and Intratumoral CpG-C Oligonucleotide Antibodies.

Two anti-PD-1 blocking antibodies were used: 29F.1A12 in initial studies and RMP1-14 in later studies. Each dose contained 250 μg antibody/injection. 29F.1A12 is a purified rat anti-mouse PD-1 antibody (Catalog No. 135202) obtained from BioLegend (San Diego, Calif.). The BioLegend anti-PD-1 antibody is rat IgG2a, kappa monoclonal antibody. Clone RMP1-14 is a purified rat anti-mouse PD-1 antibody (Catalog No. BE0146) obtained from BioXCell Inc. (West Lebanon, N.H.). The BioXCell anti-PD-1 antibody is a rat IgG2a monoclonal antibody.

Oligodeoxynucleotides.

The non-CpG, control oligodeoxynucleotide (CTRL-ODN), has the sequence 5'-TGA CTG TGA ACC TTA GAG ATG A-3' (SEQ ID NO:54) with a phosphorothioate backbone. Each dose contained 50 μg ODN/injection.

Animals and Cells.

Female BALB/c mice of 6 to 8 weeks of age were obtained from Harlan Laboratories (Indianapolis, Ind.). CT26 is a murine, fibroblast cell line (CT26.WT, Catalog No. CRL-2638™) obtained from American Type Culture Collection (ATCC, Manassas, Va.). CT26 is an N-nitroso-N-methylurethane-induced, undifferentiated colon carcinoma cell line that is frequently used as a model to test immunotherapy regimens (Wang et al., J Immunol, 154: 4685-4692, 1995).

Monotherapy Dosing Regimen.

About 8×10$^4$ CT26 cells were injected subcutaneously (SC) into the flank of BALB/c mice (n=5 to 6/group) on Day 0, using a previously published method (Brattain et al., Cancer Res, 40:2142-2146, 1980). Anti-PD-1 blocking antibody was injected intraperitoneally (IP) on Days 5, 8, 11, 14 and 18.

Combination Therapy Dosing Regimen.

About 8×10$^4$ CT26 cells were injected subcutaneously (SC) into the flank of BALB/c mice (n=5 to 6/group) on Day −7 (Brattain et al., supra, 1980). Treatment regimens started on study Day 0 (7 days after tumor cell implantation; average tumor length 5 mm). Mice were left untreated or injected intraperitoneally (IP) with 200 mcg of a mouse anti-PD-1 blocking antibody in a volume of 200 μL (neat formulation as provided by the manufacturer). Anti-PD-1 injections were administered on Days 0, 3, 7, 10, 14, 18, 21 and 25. After several anti-PD-1 injections (Day 12), mice were injected intratumorally (IT) with 50 mcg of C59-08 or CTRL-ODN in a volume of 150 μL PBS. C59-08 and CTRL-ODN injections were administered on Days 12, 14, 18, 21, 25, and 28. In both groups, anti-PD-1 treatment was continued as described above. A separate group of mice with similar-sized tumors (tumor cells were injected on study Day 0) were injected with C59-08 alone on Days 12, 14, 18, 21, 25, and 28, in the absence of anti-PD-1 pre-treatment.

Combination Therapy Dosing and T Cell Depletion Regimen.

About 8×10$^4$ CT-26 tumor cells were injected SC in the flank of mice on Day 0 (Brattain et al., supra, 1980). Mice were left untreated, or treated with anti-PD-1 by IP injection on Days 5, 9, 12, 15, 19, 22, 26 and 29. After several anti-PD-1 injections (Day 15), mice were treated with C59-08 by IT injection on Days 15, 19, 22, 26 and 29, or were left untreated. Anti-CD8 or anti-CD4 depleting antibodies were administered by IP injection on Days 14, 15, 16, 19, 22, 26 and 29 to mice in the anti-PD1/C59-08 treated group. The anti-PD-1 treated mice received 250 μg/injection of the BioXCell RMP1-14 antibody. The mice also received 50 μg/injection of C59-08. For depletions, mice received 250 μg/injection of either an anti-CD8 Ab (YTS 169.4) or an anti-CD4 Ab (GK1.5), both obtained from BioXCell.

Combination Therapy Dosing Contralateral Tumor Rejection Regimen.

About 8×10$^4$ CT-26 cells were injected SC in the left flank on Day 0 and on the right flank on Day 2. Mice were either left untreated (n=18), or injected with anti-PD-1 Ab, IP (n=19) on Days 5, 7, 11, 14, 21, 23 and 26. After several anti-PD-1 Ab injections (Day 14), anti-PD-1-treated mice were injected with C59-08 in the left tumor on Days 14, 19, 21, 23 and 26. The anti-PD-1 Ab treated mice received 250 μg/injection of the BioXCell RMP1-14 antibody, and 50 μg/injection of C59-08.

Tumor Processing for Extraction of Tumor Infiltrating Leukocytes.

Tumors were placed in a petri dish using forceps, and 5 mL of 5% FCS in RPMI media was added. The tumors were cut into small pieces using scissors, and minced using the bottom of a 3 mL syringe plunger until tumor tissue could be pipetted with a 50 mL pipet. The tumor tissue suspension was transferred into a 50 mL tube, and the petri dish was rinsed using 5 mL of 5% FCS in RPMI media twice. The tissue suspension was digested in a 100× tumor digestion enzyme mix containing 50 mg/mL collagenase 4 (Sigma-Aldrich C5138-100MG collagenase from *Clostridium histolyticum*) and 2 mg/mL DNase I (Sigma-Aldrich DN25-100MG deoxyribonuclease I from bovine pancreas). Tubes were incubated at 37° C. for 20 minutes with gentle shaking every 3 min. Samples were filtered through a 70 μm filter, and the filter was subsequently washed with 5% FCS in RPMI. Samples were centrifuged at 1400 rpm for 7 minutes at room temperature. Cells were re-suspended in 1 to 5 volumes of 5% FCS in RPMI depending on tumor size. Cells in the resulting suspension were counted using a hemocytometer.

RNA Extraction from Whole Tumors for Gene Expression Analysis.

Whole tumors were frozen in RNAlater (Catalog No. 76104) obtained from Qiagen (Venlo, NL). After thawing, total RNA was isolated from 30 mg of total homogenized whole tumor using the RNeasy Mini Kit (Catalog No. 74106) from Qiagen according to the manufacturer's instructions. Briefly, whole tumors stored in RNAlater RNA stabilization Reagent were thawed, weighed, and placed in a 2 mL PCRclean Safe-Lock eppendorf tube containing a 5 mm stainless steel bead and RLT buffer with BME (700 μL/30 mg tissue, up to 1 mL RLT per tube). Tubes were placed in the TissueLyser Adapter Set 2×24, which was operated twice for 2 min at 25 Hz. Lysates were centrifuged for 3 minutes at 13,500 rpm. The supernatant was subsequently transferred into a new 15 mL tube. RLT buffer was added as needed to meet the 700 μL/30 mg requirement. About 700 μL of lysate was used and the rest was stored at −80° C. One volume of 70% ethanol was added to the cleared lysate and 700 μL of sample was transferred to an RNeasy spin column in a 2 mL collection tube and centrifuged for 1 minute at 13,500 rpm. If the sample exceeded 700 μL, successive aliquots were processed in the same RNeasy spin column, and flow-through was discarded. 3504, of Buffer RW1 was added to the RNeasy spin column and samples were centrifuged. DNase I incubation mix (80 μL: 10 μL DNase I stock solution plus 70 μL Buffer RDD) was added directly to the RNeasy spin column and incubated at room temperature for 15 minutes. 350 μL of Buffer RW1 was added, tubes were centrifuged and the RNeasy spin column was transferred to a new tube. Two volumes of 500 μL Buffer RPE were added to the column and centrifuged for 1 minute to wash the column. The RNeasy spin column was transferred to a new 2 mL collection tube and centrifuged at full speed for 1 min. The RNeasy spin column was transferred into a new 1.5 mL collection tube and 45 μL of RNase-free water (Life Technologies) was added to the column and centrifuged for 1 min at 13,500 rpm to elute RNA.

Quantitative Real-Time Reverse Transcription-Polymerase Chain Reaction (TAQMAN)

Five (5) μg of eluted RNA was reverse transcribed by using 5× First Strand Buffer (Life Technologies), Bovine Serum Albumin (Life Technologies), Recombinant RNasin Ribonuclease Inhibitor (Promega, Madison, Wis.), Oligo (dT)15 (Promega), Random Primers (Promega), dNTP (Invitrogen, Carlsbad, Calif.), DTT (Life Technologies) and SuperScript III Reverse Transcriptase (Life Technologies) using a MyiQ Real-Time PCR Machine (Bio-Rad). Data were normalized to ubiquitin expression with cycling conditions of 15 min at 95° C., followed by 40 rounds of 15 sec at 95° C. and 1 min at 60° C. Quantification of mRNA was performed using Power SYBR Green PCR Master Mix (Life Technologies). All quantification and analysis was performed using an Applied Biosystems (Carlsbad, Calif.) StepOnePlus Real Time PCR system using StepOne v2.1 software. Relative gene expression levels were calculated using the following formula: $1.8^{(Avg\ Ct\ Ubi - Ct\ Gene)} * 100,000$.

Tumor Cell Separation with Lympholyte®-Mammal Cell Separation Media.

This procedure was used to separate tumor infiltrating leukocytes (TIL) from tumor cells. The cell suspension obtained from the tumors was brought to 7 mL by addition of 5% FCS in RPMI as needed. 7 mL Lympholyte®-Mammal Cell Separation Media (Cedarlane, Catalog No: CL5120) was added to a 15 mL conical, centrifuge tube and then 7 mL of the cell suspension was carefully layered on top. Cells were spun down at 800×g for 20 min at room temperature without braking. The top layer that formed was transferred into a 50 mL tube and filled with 5% FCS in RPMI media to the 50 mL mark. Cells were pelleted at 1800 rpm for 7 min at room temperature, under maximum acceleration and maximum braking. The media was aspirated and the TIL-containing pellet was re-suspended in 1 mL 5% FCS in RPMI media. A fraction of the cells (150 μL) were placed in 96-well U-bottom plates, pelleted at 2000 rpm for 3 min, and then re-suspended with 2504, RLT buffer for gene expression assays. The remainder of the cells were used for FACS analysis, with about 100-1504, of the TIL sample used for each staining panel.

In Vitro Stimulation of Tumor Infiltrating Leukocytes for Cytokines Production.

About $1.5 \times 10^5$ TIL isolated with Lymopholyte® Mammal Cell Separation Media (Cedarlane, Catalog No: CL5120) were stimulated for 3 hours at 37° C. with a Leukocyte Activation Cocktail containing BD GolgiPlug (500×) obtained from BD Biosciences (Catalog No. 550583) with phorbol myristate acetate (PMA), ionomycin and brefeldin A (BFA), or BFA alone (3 μg/mL final concentration), in a final volume of 200 μL. Samples were analyzed for cytokine production by intracellular staining and flow cytometry.

Cell Staining and Fluorescence Activated Cell Sorting (FACS) Analysis

All reagents were kept at 4° C. All washes involved pipetting the plated cell suspensions up and down three times, followed by centrifuging at 1800 rpm for 3 min at 4° C., and discarding the supernatant. Cells were pelleted after stimulation for 3 hours and were resuspended in 80 μL/well FACS buffer (PBS, 10% FBS, 0.1% sodium azide) for each sample to create a cocktail including 2 μL Fc Blocker and 0.5 μg/mL of each antibody of interest per sample. Samples were incubated at 4° C. for 20 min before washing and resuspension in 200 μL/well FACS buffer. To fix the cells, 200 μL of 1% paraformaldehyde was added to each well, and the plate was incubated in the dark at 4° C. for 20 min for surface staining. The cells were then washed, pelleted and resuspended in 300 μl/well FACS buffer, and data were acquired immediately using a flow cytometer (LSRII from BD Bioscience).

For intracellular staining, samples stored overnight at 4° C. were pelleted and resuspended in 0.5% saponin buffer in PBS for 10 min at RT to permeabilize the cells. After an additional spin, cells were stained with 80 μL of staining mix plus 2 μL Fc Blocker and antibodies of interest in 0.5% saponin buffer in PBS for 30 min at 4° C.: 2.5 μL anti-mouse IFN-γ-PE (Tonbo Biosciences, Cat. 50-7311-U100), and 2.54, anti-mouse TNF-α-APC (Biolegend, Cat. 506308). Cells were pelleted and washed before resuspension in 300

µL of FACS buffer, and data were acquired immediately acquired using a flow cytometer (LSRII from BD bioscience).

Mice Bearing CT-26 Tumor Nodules Produce a Heterogeneous Response to Systemic PD-1 Blockade.

Figure 14A:
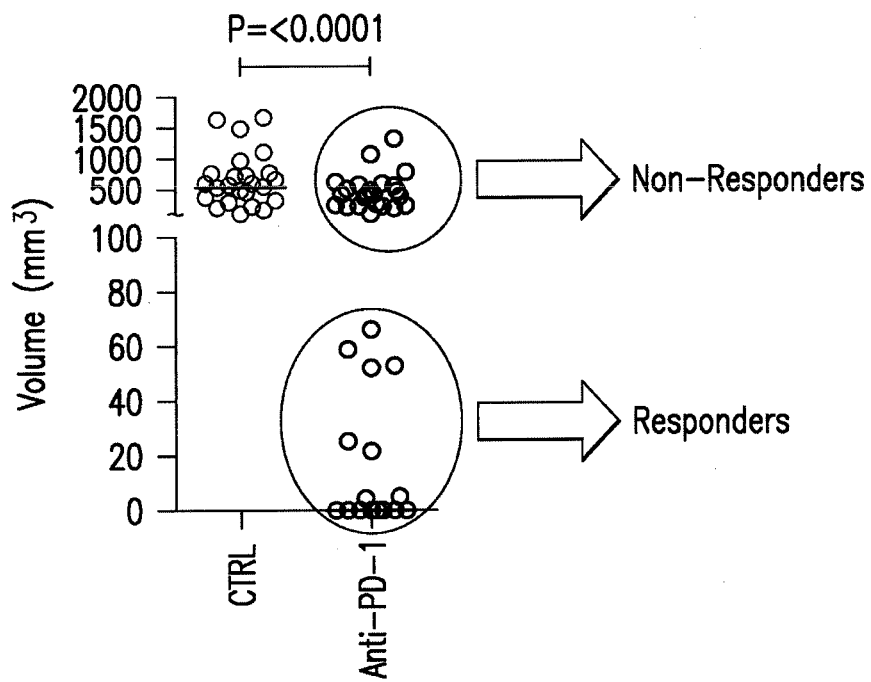
FIG. 14A shows the distribution of tumor nodule size in mice injected with CT-26 colon carcinoma cells.
Figure 14B:
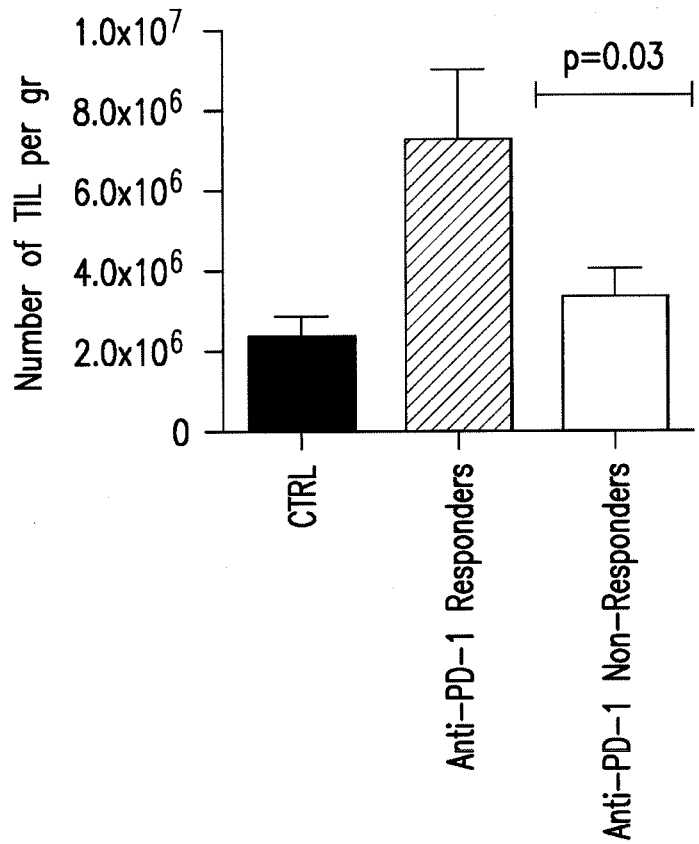
FIG. 14B shows the number of tumor infiltrating leukocytes (TILs) per gram of tumor tissue. Significance was calculated using an unpaired test using Prism GraphPad software.
Figure 14C:
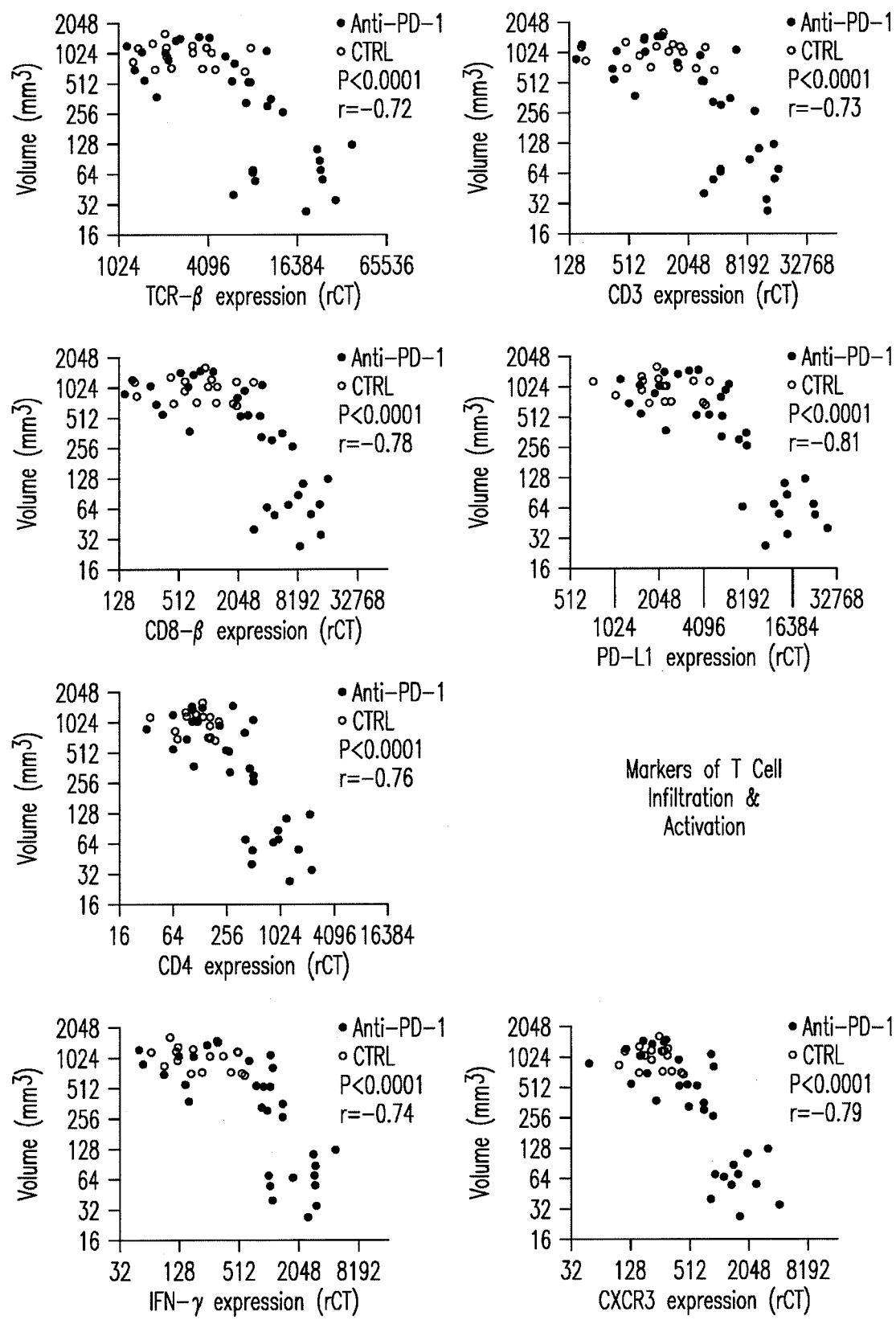
Figure 14D:
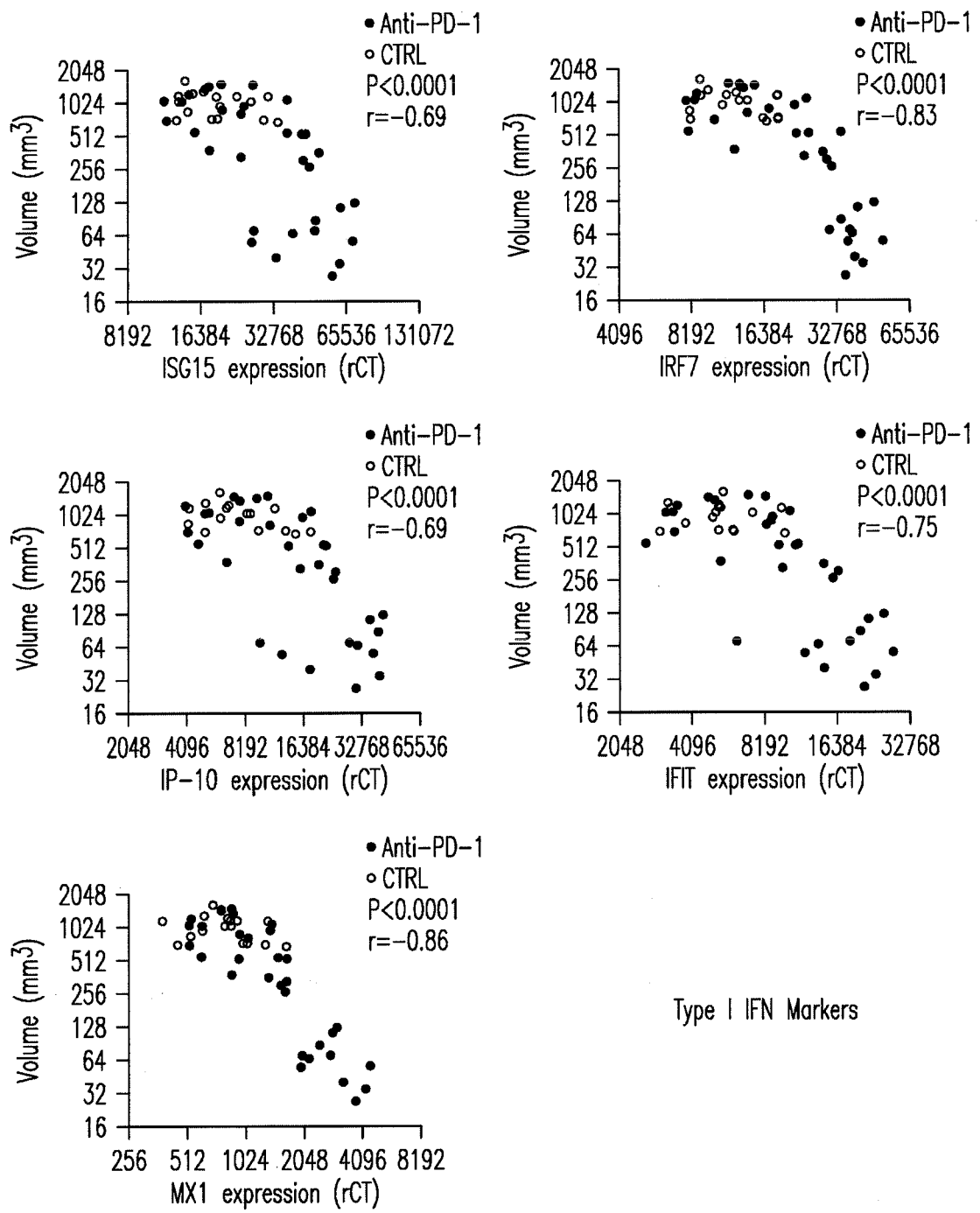
FIG. 14D shows the levels of gene expression of various type I interferon (IFN) responsive markers in tumor tissue, versus tumor size.

Tumor nodule sizes were measured 2 days after the last anti-PD-1 injection (day 21). FIG. 14A shows that 17 out of 43 (40%) tumors exhibited a response to anti-PD-1 treatment, with 8 of the 17 tumors (19%) having completely regressed. The remaining 26 out of 43 tumors exhibited a size distribution similar to that of control (CTRL) untreated mice. That is, 60% of tumors did respond to the PD-1 blockade. As shown in FIG. 14B, tumors that had a response to anti-PD-1 treatment have an increased number of tumor infiltrating leukocytes (TILs) as compared to untreated (CTRL) tumors or tumors that did not respond to anti-PD-1 treatment. Whole tumors, which were harvested 2-4 days after the last anti-PD-1 injection were processed for analysis of gene expression using a TAQMAN assay. The response to anti-PD-1 correlated with the level of expression of T cell infiltration and activation markers (FIG. 14C) and type I interferon responsive markers (FIG. 14D).

These data demonstrate that the CT-26 tumor model follows a clear bi-modal response: mice capable of producing an antitumor response demonstrate a significant control over tumor growth, whereas mice that are not able to respond to treatment proceed at the same rate of growth as untreated tumors. In addition, these data show a negative correlation between tumor volume and expression of T cell infiltration and activation, and type I interferon responsive genes.

Intratumoral C59-08 Reverses Tumor Escape from Anti-PD-1 Therapy and Leads to Long-Term, Immune-Mediated Control of Tumor Growth.

Figure 15A:
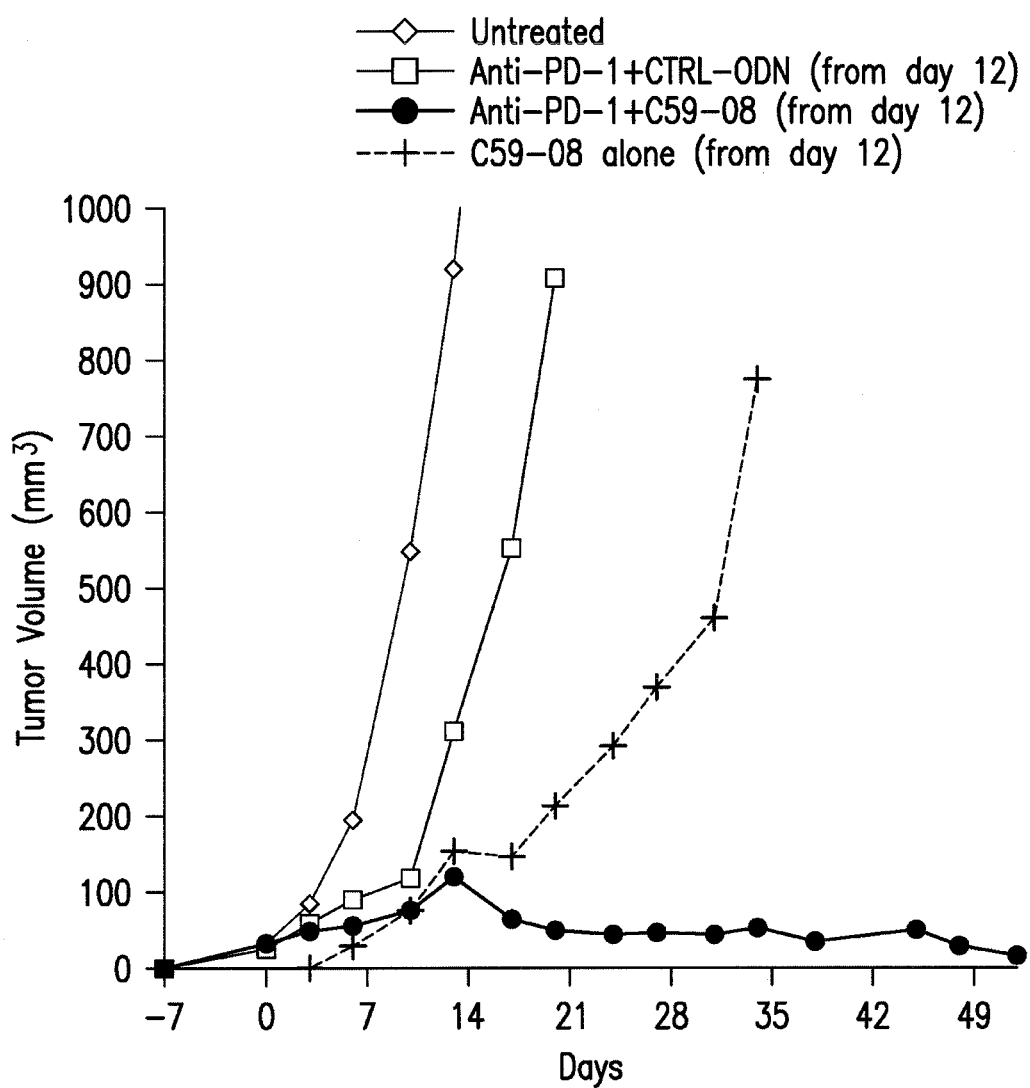
FIG. 15A shows the mean tumor size.
Figure 15B:
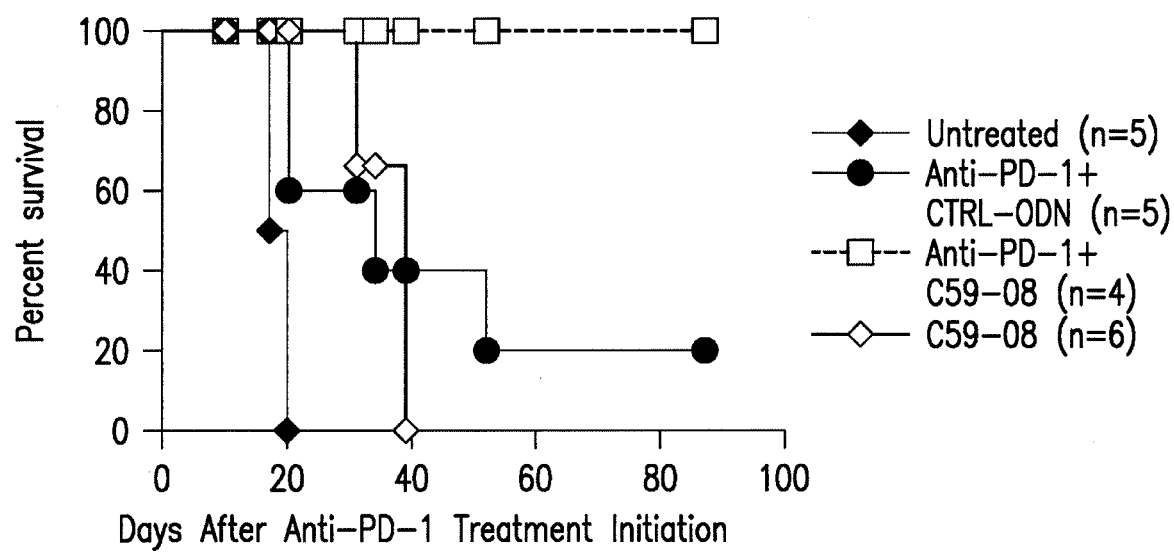
FIG. 15B shows the percent survival.
Figure 15C:
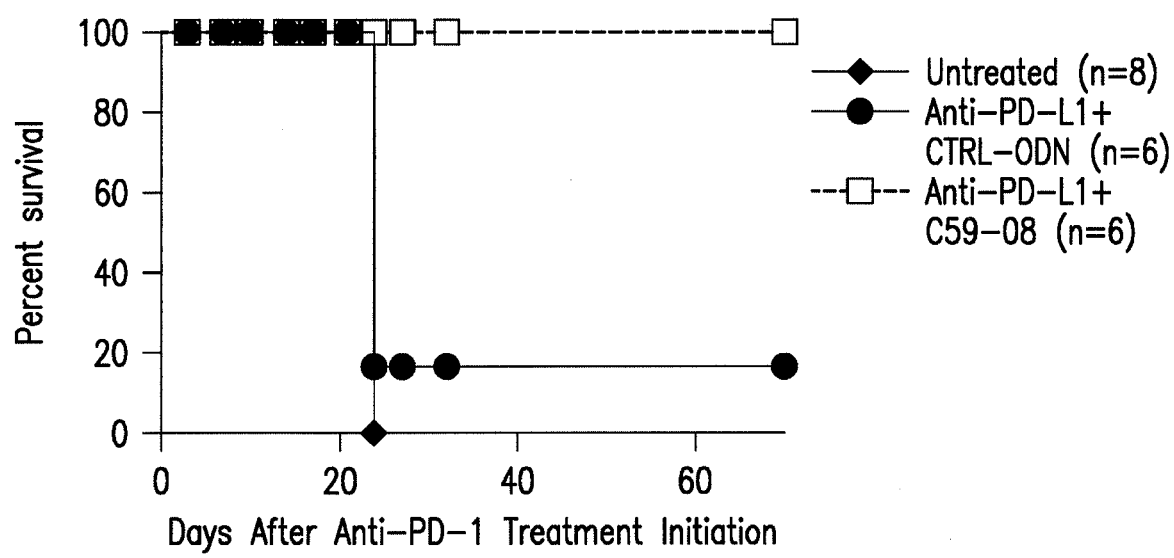
FIG. 15C shows the percent survival of various groups of treated and untreated mice, which were engrafted with CT-26 colon carcinoma cells.

FIG. 15A shows the mean tumor volume over time, while FIG. 15B-C shows the long term survival of mice of various treatment groups. Intratumoral C59-08 with continued anti-PD-1 treatment improves the survival rate as compared to C59-08 or anti-PD-1 monotherapy. This proof of concept study indicates that the combination of C59-08 with an anti-PD-1 antibody is able to convert non-responders into responders capable of complete tumor rejection.

CD8+ T Cells but not CD4+ T Cells are Required for the Efficacy of Anti-PD-1 Plus C59-08 Combination Treatment.

Figure 16:
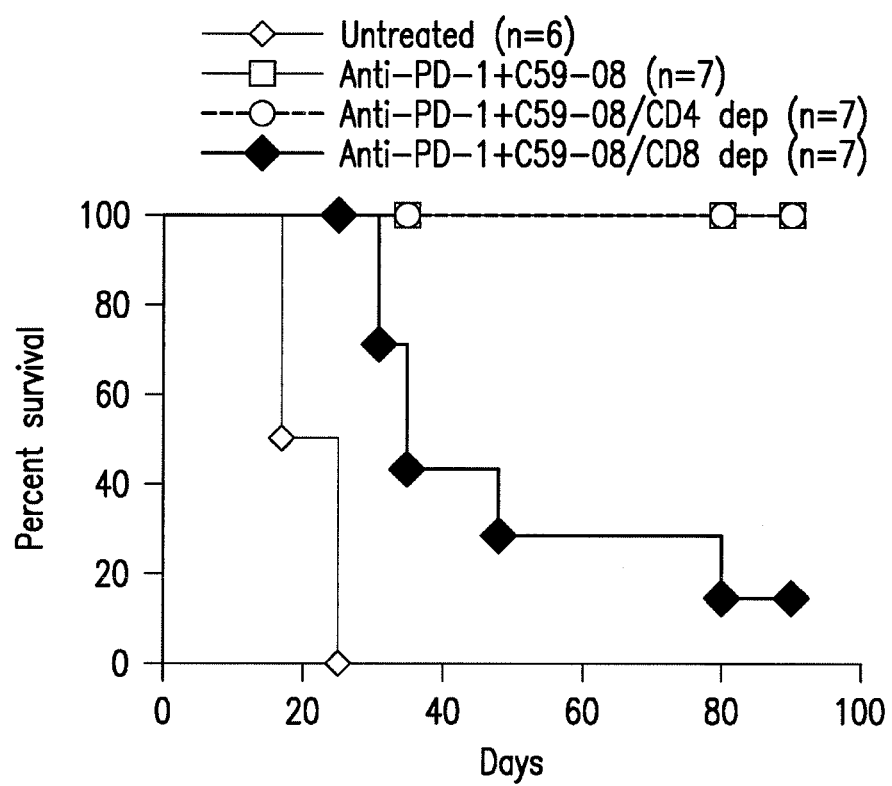
FIG. 16 shows the percent survival of mice engrafted with CT-26 colon carcinoma cells, which received either anti-PD-1 Ab systemically and C59-08 intratumorally, in the presence or absence of CD4 or CD8 cells, or were left untreated.

FIG. 16 shows that depletion of CD8+ T cells abolishes the efficacy of anti-PD-1 plus C59-08 combination treatment.

Anti-PD-1 Plus C59-08 Combination Therapy Allows for Rejection of Contralateral Tumors.

Figure 17:
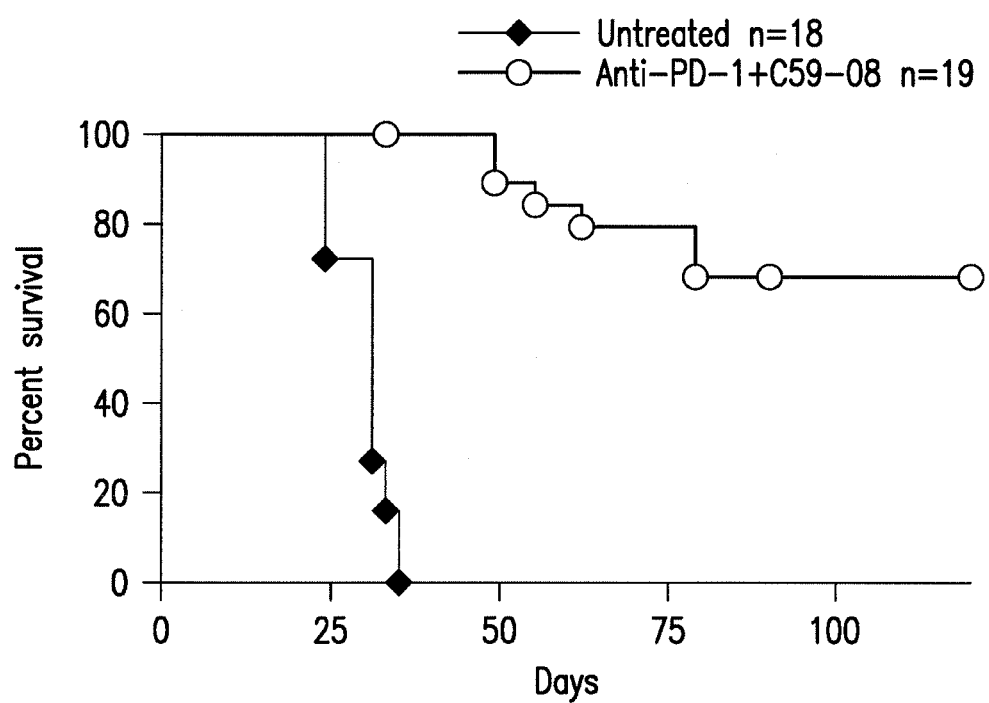
FIG. 17 shows the percent survival of mice engrafted bilaterally with CT-26 colon carcinoma cells, which received either anti-PD-1 Ab systemically and C59-08 intratumorally, or were left untreated.
Figure 18A:
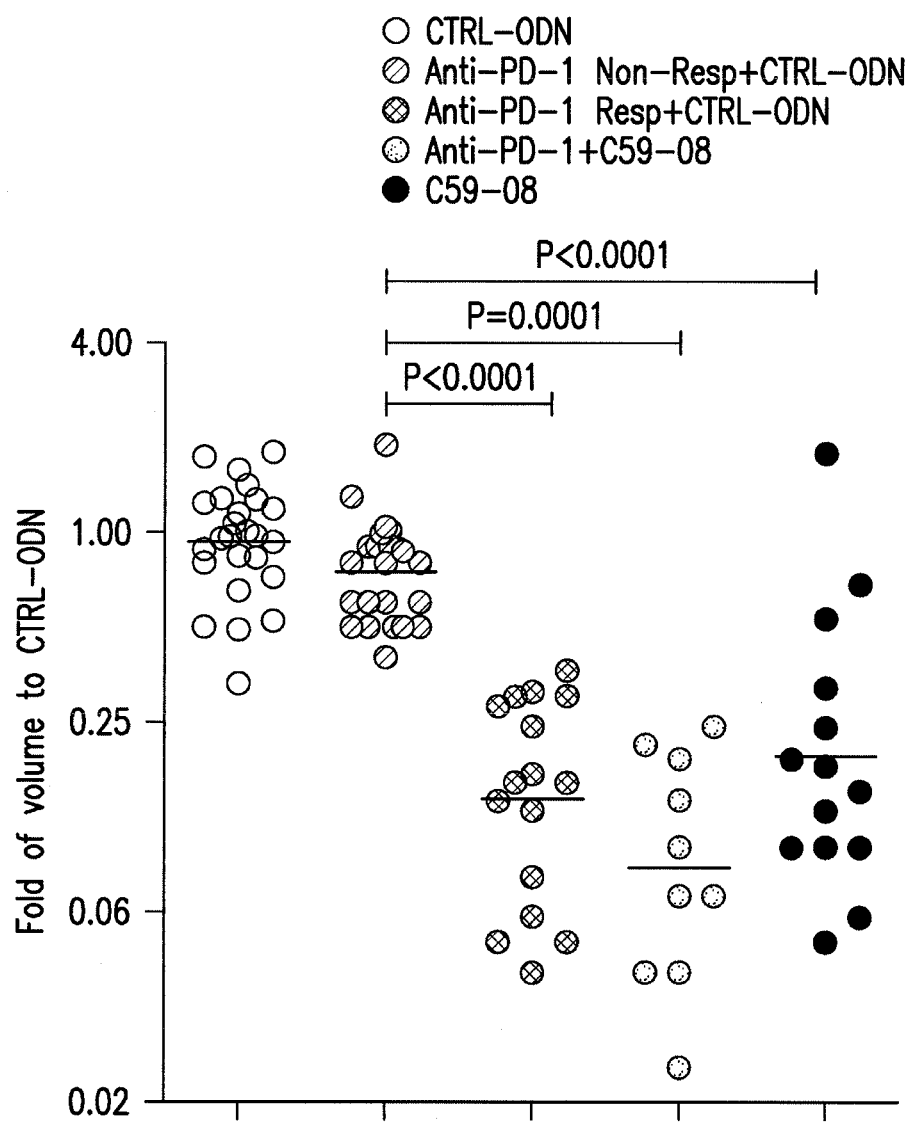
FIG. 18A shows the tumor volume of mice engrafted with CT-26 colon carcinoma cells, which received various treatments, relative to the mean tumor volume of control oligonucleotide-treated mice.
Figure 18B:
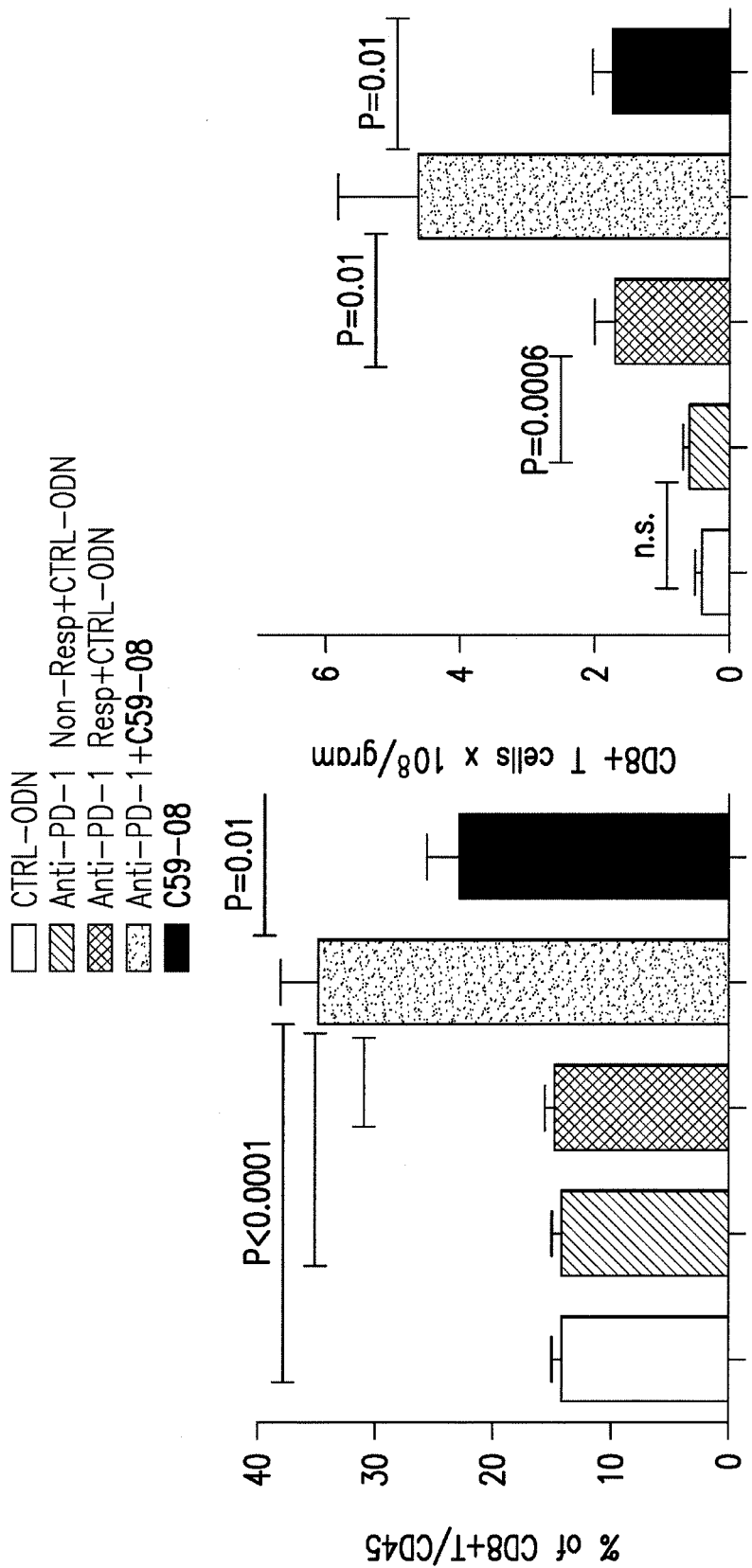
FIG. 18 B shows the percent CD8+ T cells among CD45+ tumor-infiltrating leukocytes, and the total number of CD8+ T cells per gram of tumor tissue.
FIG. 18C and FIG. 18D shows the levels of TNF-α and IFN-γ production by 150,000 tumor infiltrating leukocytes, as measured by intracellular staining and flow cytometry gated on CD8+ T cells, after being stimulated for 3 hours with PMA and ionomycin in the presence of BFA (scattered dash bars) or BFA alone (dense dashed bars). For FIG. 18C, the numbers labeled on the Y axis are $-10^3$, 0, $10^3$, $10^4$, $10^5$ from bottom to top, respectively, and the numbers labeled on the X axis are $-10^3$, 0, $10^3$, $10^4$, $10^5$ from left to right, respectively.
Figure 18C:
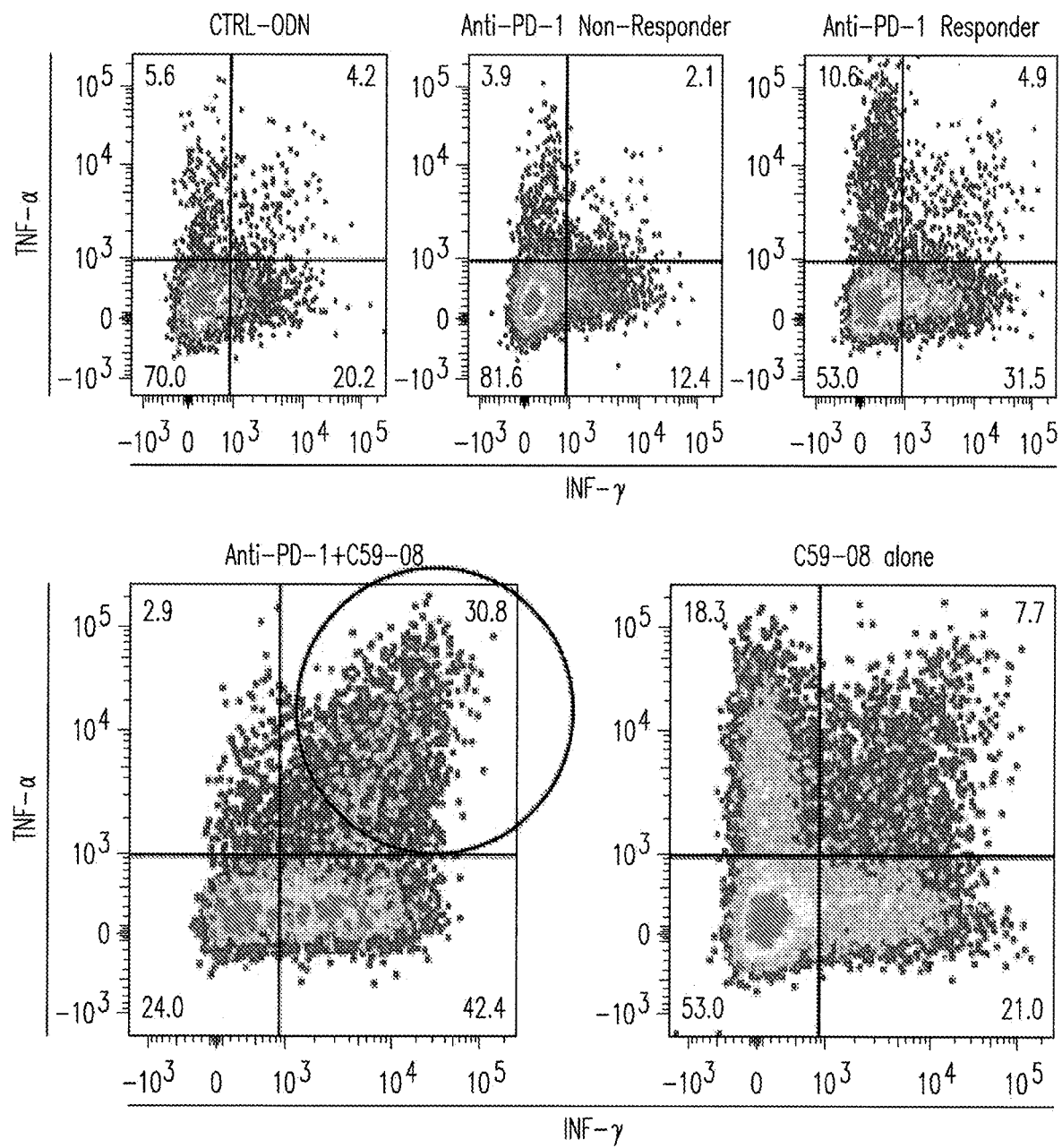
Figure 18D:
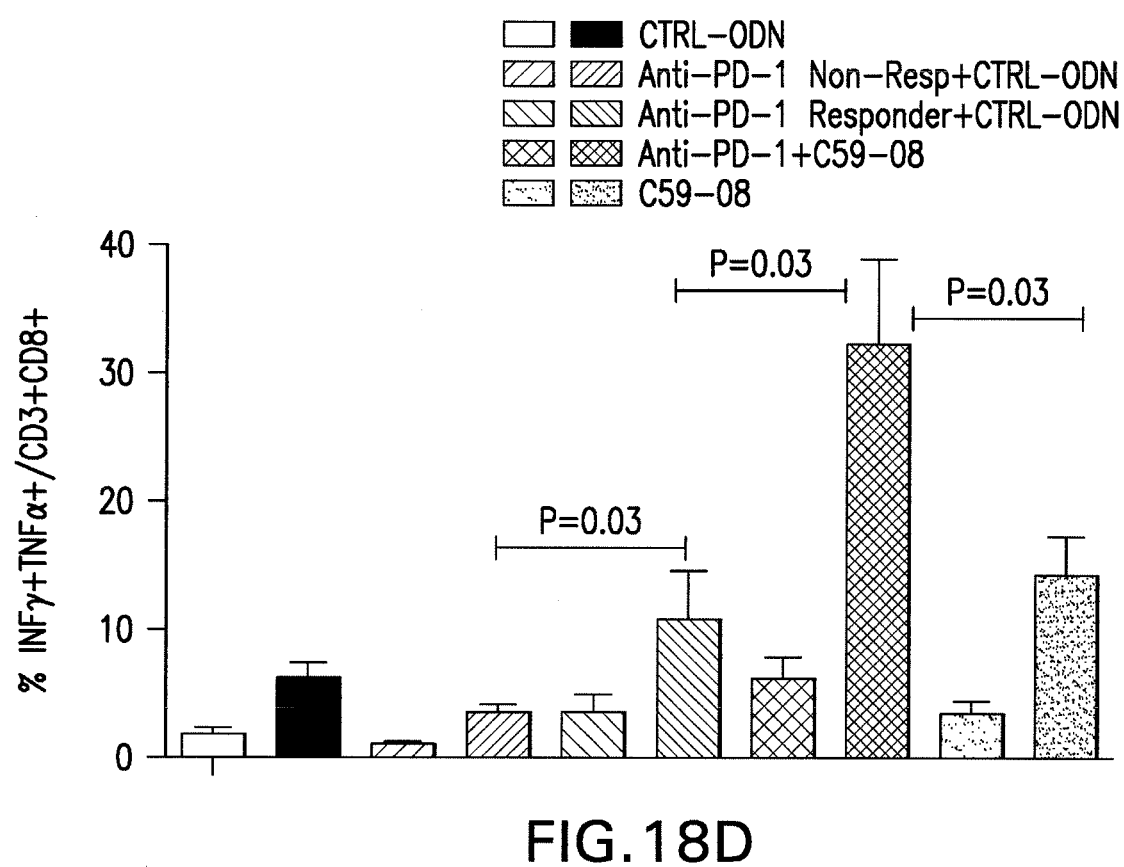

FIG. 17 shows that 13 out of 19 mice (68%) survived and rejected both C59-08-injected, as well as C59-08-uninjected tumor nodules in the anti-PD-1 plus C59-08 treated group. Untreated mice failed to demonstrate a reduction in tumor size or reject any tumors (0% survival). Thus, the anti-tumor response generated by C59-08 plus anti-PD-1 combination therapy is able to eliminate tumors at a site distant from the C59-08 injection.

C59-08 in Combination with a PD-1 Blockade Strongly Induces Infiltration and Activation of Polyfunctional CD8+ T Cells.

At the time of collection, tumors treated with anti-PD-1, were grouped based on the rate of response. Tumor Volume ($mm^3$) was calculated according to the formula: $(width)^2 \times length/2$. Tumors classified as non-responsive to anti-PD-1 demonstrated an average reduction in volume of about 20% as compared to control oligonucleotide treated tumors. In contrast, tumors classified as responsive to anti-PD-1 demonstrated an average reduction in volume of about 80% as compared to control oligonucleotide treated tumors.

As shown in FIG. 18A-D, C59-08 was shown to strongly synergize with anti-PD-1 to induce CD8 T cell infiltration and differentiation in polyfunctional cells able to concomitantly produce IFN-gamma and TNF-alpha. In brief, the increase in number and activation status of the CD8+ T cell infiltrate of combination treated tumors is even better than that of anti-PD-1-responsive tumors in the absence of C59-08. This indicates that C59-08 has the ability to improve anti-tumor responses in both anti-PD-1 responders, as well as anti-PD-1 nonresponders.

C59-08 Monotherapy is Effective in Reducing Tumor Volume and Inducing Expression of Interferon-Stimulated and Inflammatory Genes.

Mice bearing CT26 colon carcinomas were treated intratumorally (IT) with C59-08 or a control oligodeoxynucleotide. On Day 25 (3 days after the last treatment), the group injected with the CTRL-ODN was euthanized due to excessive enlarged tumors. On Day 35 (13 days after the last treatment), the group injected with C59-08 was euthanized. At day 35, two of six mice treated with C59-08 rejected the tumor, leaving no tissue available for harvest. In these instances, a value of zero was used for calculating the mean tumor volume. The remaining four of six tumors nodules were used to extract TILs.

Figure 19A:
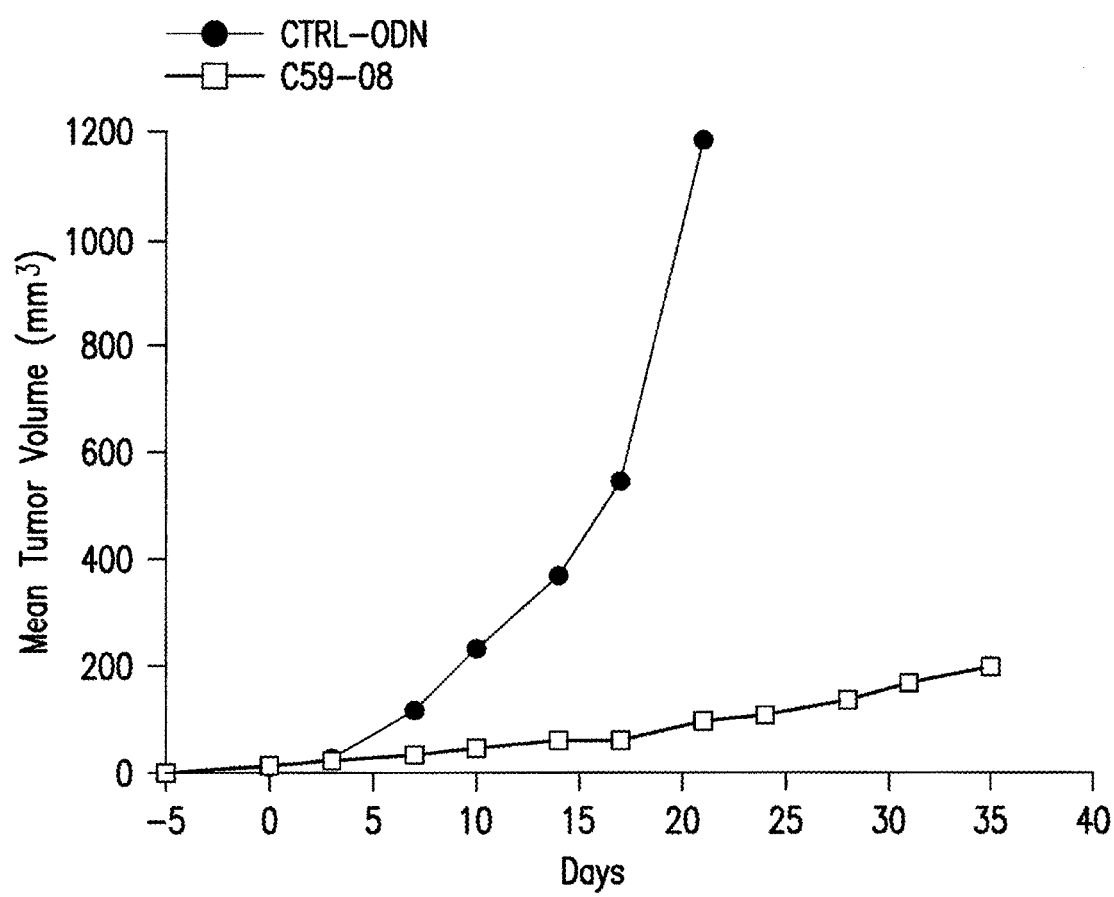
FIG. 19A shows the tumor growth curve of mice engrafted with CT-26 colon carcinoma cells, which received either C59-08 intratumorally, or a control oligonucleotide intratumorally.
Figure 19B:
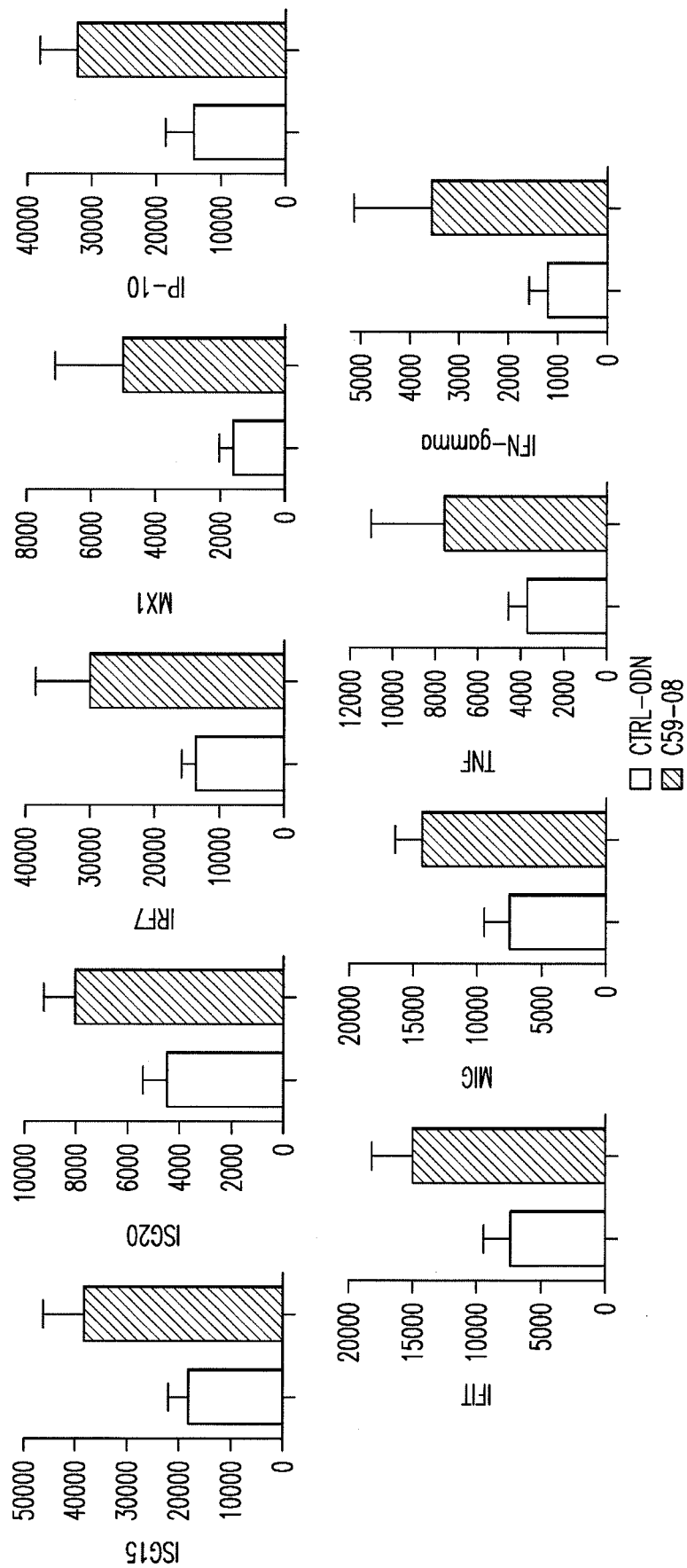
FIG. 19B shows the levels of expression of various type I interferon responsive genes by tumor infiltrating leukocytes of mice treated with either C59-08 or a control oligonucleotide. Data represented as relative threshold cycle (CT) of the gene of interest relative to the housekeeping gene, ubiquitin.

As shown in FIG. 19A-B, C59-08 was able to inhibit tumor growth and to induce the expression of IFN-stimulated (ISG15, ISG20, IRF7, MX1, IP-10, and IFIT) and inflammatory (MIG, TNF-alpha, and IFN-gamma) genes in leukocytes purified from the treated tumors. This indicates that C59-08 is able to induce a long lasting upregulation of a favorable gene expression pattern in TILs.

Summary

An antibody to the T cell surface PD-1 receptor acts to block the immune inhibitory pathway that is switched on by cancer cells (Wolchok and Chan, Nature, 515:496-498, 2014). Now as described herein, a CpG-C ODN termed C59-08 was shown to be efficacious when administered alone, or in combination with an antibody to PD-1, in inhibiting the growth of established tumors in the murine CT26 model of transplantable colon carcinoma. Specifically, C59-08 was able to inhibit tumor growth, increase the number of TILs, and induce a desirable gene expression pattern. Although, C59-08 given alone was unable to affect tumor rejection, C59-08 was shown to synergize with anti PD-1 treatment resulting in the rejection of established tumors, and an increase in the duration of relapse-free survival. Strikingly, addition of intratumoral C59-08 to established anti-PD-1 therapy resulted in the conspicuous infiltration of activated T cells that correlates to tumor rejection. Thus, the combination of an anti-PD1 antibody and a CpG-C ODN has been shown to be superior in inducing tumor rejection than either of single agent alone.

Example 5 Phase 1b/2 Trial of Intratumoral C59-08 in Combination with Pembrolizumab in Patients with Metastatic Melanoma Part 1 (Phase 1b Dose Escalation) evaluates 3 escalating dose levels of C59-08 in patients with metastatic melanoma, and Part 2 (Phase 2 Expansion) will consist of expansion cohorts to further evaluate efficacy and safety in specific melanoma populations. The patient populations include:
1) Metastatic melanoma patients who are anti-programmed death receptor-1/ligand-1 (anti-PD-1/L1) therapy naive;
2) Metastatic melanoma patients with confirmed progressive disease while receiving anti-PD-1 therapy.

In both Parts, patients are treated with 200 mg IV pembrolizumab every 3 weeks until progression or for up to 45 weeks after the first dose.

In Part 1, starting on Day 1, patients are treated with 4 weekly doses of C59-08 at 2, 4 or 8 mg followed by 1 dose every 3 weeks until progression or for up to 24 weeks after the first dose. C59-08 is injected intratumorally into Lesion A, the same site used throughout the trial. If at any point during treatment, Lesion A has completely regressed, remaining C59-08 injections are given by peritumoral injection into the site of Lesion A.

In Part 2 in the expansion cohorts, each patient is treated with pembrolizumab in combination with C59-08 using the dose selected from Part 1.

In Cohort 1 (anti-PD-1/L1 naïve), starting on Day 22, patients are treated with C59-08 once a week for 4 weeks followed by once every 3 weeks for 9 weeks.

In Cohort 2 (progressive disease on anti-PD-1 therapy), starting on Day 1, patients are treated with C59-08 once a week for 4 weeks followed by once every 3 weeks for nine weeks.

In Part 2, C59-08 is injected intratumorally into up to four lesions (Lesion A, Lesion B, Lesion C, Lesion D), and the same site(s) is used throughout the trial. If at any point during treatment the injected lesion(s) have completely regressed, C59-08 is administered by peritumoral injection into the site(s) of the injected lesions.

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk prognostic factors. *Neoplasia* (2006) 8: 190-198.
5. Hamanishi J et al. Programmed cell death 1 ligand 1 and tumor-infiltrating CD8+ T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother.* (2007) 56: 1173-1182.
13. Hino et al. Tumor cell expression of programmed cell death-1 is a prognostic factor for malignant melanoma. *Cancer* (2010): 00: 1-9.
14. Ghebeh H. Foxp3+ tregs and B7-H1+/PD-1+ T lymphocytes co-infiltrate the tumor tissues of high-risk breast cancer patients: implication for immunotherapy. *BMC Cancer.* 2008 Feb. 23; 8:57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.

All references cited herein are incorporated by reference to the same extent as if each individual publication, database entry (e.g. Genbank sequences or GeneID entries), patent application, or patent, was specifically and individually indicated to be incorporated by reference. U.S. Provisional Applications 62/169,309 and 62/168,449 are hereby incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. To the extent that the references provide a definition for a claimed term that conflicts with the definitions provided in the instant specification, the definitions provided in the instant specification shall be used to interpret the claimed invention.

The invention claimed is:

1. A method for treating cancer in an individual comprising administering to the individual a PD-1 antagonist and a TLR9 agonist, wherein the TLR9 agonist is a CpG-C type oligonucleotide having a sequence consisting of 5'-TCGAACGT-TCGAACGTTCGAACGTTCGAAT-3' (SEQ ID NO: 45), and wherein the PD-1 antagonist is:

(i) a monoclonal antibody, or antigen binding fragment thereof, which comprises light chain CDRs of SEQ ID NOs: 7, 8 and 9 and heavy chain CDRs of SEQ ID NOs: 10, 11 and 12, or (ii) an anti-PD-1 monoclonal antibody which comprises a heavy chain and a light chain, and wherein the heavy chain comprises SEQ ID NO: 21 and the light chain comprises SEQ ID NO: 22.

2. The method of treating cancer of claim 1, wherein the CpG-C type oligonucleotide is an oligodeoxynucleotide with a phosphorothioate backbone.

3. The method of treating cancer of claim 1, wherein the cancer is a bladder cancer, a breast cancer, a clear cell kidney cancer, a head/neck a squamous cell carcinoma, a lung squamous cell carcinoma, a malignant melanoma, a non-small-cell lung cancer (NSCLC), an ovarian cancer, a pancreatic cancer, a prostate cancer, a renal cell cancer, a small-cell lung cancer (SCLC), or a triple negative breast cancer.

4. The method of treating cancer of claim 1, wherein the cancer is advanced or metastatic melanoma.

5. The method of treating cancer of claim 1, wherein cancer tests positive for human PD-L1.

6. The method of treating cancer of claim 1, wherein the PD-1 antagonist is pembrolizumab.

7. The method of treating cancer of claim 6, wherein the pembrolizumab is administered at a dose of 200 mg once every three weeks and the oligonucleotide of SEQ ID NO: 45 is intratumorally administered at a dose of from 1 to 16 mg once a week.

8. The method of treating cancer of claim 6, wherein the pembrolizumab is administered at a dose of 200 mg once every three weeks and the oligonucleotide of SEQ ID NO: 45 is intratumorally administered at a dose of from 1 to 16 mg once every three weeks.

9. The method of treating cancer of claim 7, wherein the individual is confirmed progressive while receiving prior anti-PD-1 therapy.

10. The method of treating cancer of claim 8, wherein the individual is confirmed progressive while receiving prior anti-PD-1 therapy.

11. The method of treating cancer of claim 7, wherein the oligonucleotide is injected intratumorally at a dose of 2.0, 4.0, or 8.0 mg.

12. The method of treating cancer of claim 8, wherein the oligonucleotide is injected intratumorally at a dose of 2.0, 4.0, or 8.0 mg.

13. The method of treating cancer of claim 7, wherein the individual has not been previously treated for the cancer with an anti-PD-1 therapy or an anti-PD-L1 therapy.

14. The method of treating cancer of claim 8, wherein the individual has not been previously treated for the cancer with an anti-PD-1 therapy or an anti-PD-L1 therapy.

15. The method of treating cancer of claim 1, wherein the cancer is an advanced or metastatic melanoma, a renal cell carcinoma, a non-small cell lung cancer, a bladder cancer, or a colorectal cancer.

16. The method of treating cancer of claim 1, wherein the CpG-C type oligonucleotide is a sodium salt, and the oligonucleotide is an oligodeoxynucleotide with a phosphorothioate backbone.

17. The method of treating cancer of claim 2, wherein the CpG-C type oligonucleotide is a sodium salt.

18. The method of treating cancer of claim 3, wherein the CpG-C type oligonucleotide is a sodium salt, and the oligonucleotide is an oligodeoxynucleotide with a phosphorothioate backbone.

19. The method of treating cancer of claim 4, wherein the CpG-C type oligonucleotide is a sodium salt, and the oligonucleotide is an oligodeoxynucleotide with a phosphorothioate backbone.

20. The method of treating cancer of claim 5, wherein the CpG-C type oligonucleotide is a sodium salt, and the oligonucleotide is an oligodeoxynucleotide with a phosphorothioate backbone.

21. The method of treating cancer of claim 6, wherein the CpG-C type oligonucleotide is a sodium salt, and the oligonucleotide is an oligodeoxynucleotide with a phosphorothioate backbone.

22. The method of treating cancer of claim 7, wherein the CpG-C type oligonucleotide is a sodium salt, and the oligonucleotide is an oligodeoxynucleotide with a phosphorothioate backbone.

23. The method of treating cancer of claim 8, wherein the CpG-C type oligonucleotide is a sodium salt, and the oligonucleotide is an oligodeoxynucleotide with a phosphorothioate backbone.

24. The method of treating cancer of claim 9, wherein the CpG-C type oligonucleotide is a sodium salt, and the oligonucleotide is an oligodeoxynucleotide with a phosphorothioate backbone.

25. The method of treating cancer of claim 10, wherein the CpG-C type oligonucleotide is a sodium salt, and the oligonucleotide is an oligodeoxynucleotide with a phosphorothioate backbone.

26. The method of treating cancer of claim 11, wherein the CpG-C type oligonucleotide is a sodium salt, and the oligonucleotide is an oligodeoxynucleotide with a phosphorothioate backbone.

27. The method of treating cancer of claim 12, wherein the CpG-C type oligonucleotide is a sodium salt, and the oligonucleotide is an oligodeoxynucleotide with a phosphorothioate backbone.

28. The method of treating cancer of claim 13, wherein the CpG-C type oligonucleotide is a sodium salt, and the oligonucleotide is an oligodeoxynucleotide with a phosphorothioate backbone.

\* \* \* \* \*